(12) United States Patent
Dacosta et al.

(10) Patent No.: US 12,161,546 B2
(45) Date of Patent: Dec. 10, 2024

(54) LIGAMENT FIXATION SYSTEM, IMPLANTS, DEVICES, AND METHODS OF USE

(71) Applicant: Paragon 28, Inc., Englewood, CO (US)

(72) Inventors: Albert Dacosta, Lone Tree, CO (US); Sean Gill, Denver, CO (US); Richard David Hunt, Arvada, CO (US); Frank Bono, Castle Rock, CO (US); Thomas R. Williams, Bon Aqua, TN (US); Randy Allard, Golden, CO (US); Benjamin Majors, Englewood, CO (US)

(73) Assignee: Paragon 28, Inc., Englewood, CO (US)

( * ) Notice: Subject to any disclaimer, the term of this patent is extended or adjusted under 35 U.S.C. 154(b) by 0 days.

(21) Appl. No.: 18/295,545

(22) Filed: Apr. 4, 2023

(65) Prior Publication Data
US 2023/0240833 A1 Aug. 3, 2023

Related U.S. Application Data

(60) Continuation of application No. 17/249,205, filed on Feb. 23, 2021, now Pat. No. 11,617,642, which is a
(Continued)

(51) Int. Cl.
*A61F 2/08* (2006.01)
*A61B 17/04* (2006.01)
*A61B 17/86* (2006.01)

(52) U.S. Cl.
CPC ........ *A61F 2/0811* (2013.01); *A61B 17/0401* (2013.01); *A61B 17/8625* (2013.01);
(Continued)

(58) Field of Classification Search
CPC ............ A61F 2/0811; A61F 2002/0817; A61B 17/0401; A61B 17/8625; A61B 2017/044;
(Continued)

(56) References Cited

U.S. PATENT DOCUMENTS

| 3,268,965 A | 8/1966 | Arthur |
|---|---|---|
| 3,953,896 A | 5/1976 | Treace |

(Continued)

FOREIGN PATENT DOCUMENTS

| CN | 102670291 | 9/2012 |
|---|---|---|
| CN | 102920498 | 2/2013 |

(Continued)

OTHER PUBLICATIONS

Extended European Search Report for European Application No. 20863144.0, dated Aug. 25, 2023, 5 pages.
(Continued)

*Primary Examiner* — Phong Son H Dang
(74) *Attorney, Agent, or Firm* — Heslin Rothenberg Farley & Mesiti P.C.; Jacquelyn A. Graff, Esq.

(57) ABSTRACT

Devices, systems, implants and methods for achieving ligament fixation are disclosed. An implant includes a head member and an anchor member coupled to the head member. The implant includes tension member that couples the head member to the anchor member. The head member and the anchor member include a cannulation that receives the tension member therein. The implant may include a coupling member positioned between and coupling the head member and the anchor member, the coupling member including a cannulation that receives the tension member therethrough. Insertion instruments for inserting an implant for ligament fixation are also disclosed. Methods of using an implant for achieving ligament fixation are also disclosed.

17 Claims, 61 Drawing Sheets

Related U.S. Application Data division of application No. 16/517,295, filed on Jul. 19, 2019, now Pat. No. 10,945,830, which is a continuation of application No. PCT/US2018/055028, filed on Oct. 9, 2018.

(60) Provisional application No. 62/569,238, filed on Oct. 6, 2017.

(52) U.S. Cl.
CPC .  *A61B 2017/044* (2013.01); *A61B 2017/0448* (2013.01); *A61B 2017/0461* (2013.01); *A61F 2002/0817* (2013.01)

(58) Field of Classification Search
CPC .... A61B 2017/0448; A61B 2017/0461; A61B 17/8685
See application file for complete search history.

(56) References Cited

U.S. PATENT DOCUMENTS

| | | | |
|---|---|---|---|
| 4,955,910 | A | 9/1990 | Bolesky |
| 5,004,474 | A | 4/1991 | Fronk |
| 5,061,137 | A | 10/1991 | Gourd |
| 5,152,790 | A | 10/1992 | Rosenberg |
| 5,486,197 | A | 1/1996 | Le |
| 5,507,812 | A | 4/1996 | Moore |
| 5,702,397 | A | 12/1997 | Goble |
| 5,743,912 | A | 4/1998 | Lahille |
| 5,968,045 | A | 10/1999 | Frazier |
| 6,187,008 | B1 | 2/2001 | Hamman |
| 6,461,373 | B2 | 10/2002 | Wyman |
| 6,620,195 | B2 | 9/2003 | Goble |
| 6,652,592 | B1 | 11/2003 | Grooms |
| 6,921,402 | B2 | 7/2005 | Contiliano |
| 7,235,078 | B2 | 6/2007 | West, Jr. |
| 7,235,091 | B2 | 6/2007 | Thornes |
| 7,608,098 | B1 | 10/2009 | Stone |
| 7,625,395 | B2 | 12/2009 | Mückter |
| 7,727,278 | B2 | 6/2010 | Olsen |
| 7,955,388 | B2 | 6/2011 | Jensen |
| 8,128,696 | B2 | 3/2012 | Mayr |
| 8,202,295 | B2 | 6/2012 | Kaplan |
| 8,439,976 | B2 | 5/2013 | Albertorio |
| 8,529,611 | B2 | 9/2013 | Champagne |
| 8,597,337 | B2 | 12/2013 | Champagne |
| 8,668,419 | B2 | 3/2014 | Hardt |
| 8,696,716 | B2 | 4/2014 | Kartalian |
| 8,696,719 | B2 | 4/2014 | Lofthouse |
| 8,864,804 | B2 | 10/2014 | Champagne |
| 9,089,371 | B1 | 7/2015 | Faulhaber |
| 9,138,219 | B2 | 9/2015 | Horrell |
| 9,345,522 | B2 | 5/2016 | Songer |
| 9,687,256 | B2 | 6/2017 | Granberry |
| 9,877,760 | B2 | 1/2018 | Ehler |
| 10,070,896 | B2 | 9/2018 | Biedermann |
| 10,314,631 | B2 | 6/2019 | Gonzalez Blohm |
| 10,610,276 | B2 | 4/2020 | Lutz |
| 2002/0133156 | A1 | 9/2002 | Cole |
| 2002/0143333 | A1 | 10/2002 | von Hoffmann |
| 2004/0172032 | A1 | 9/2004 | Jackson |
| 2005/0059972 | A1 | 3/2005 | Biscup |
| 2007/0162124 | A1 | 7/2007 | Whittaker |
| 2007/0282342 | A1 | 12/2007 | Niederberger |
| 2008/0182227 | A1 | 7/2008 | Wolf |
| 2009/0198287 | A1 | 8/2009 | Chiu |
| 2009/0306777 | A1 | 12/2009 | Widmer |
| 2011/0040335 | A1 | 2/2011 | Stihl |
| 2011/0184471 | A1 | 7/2011 | Foley |
| 2011/0276099 | A1 | 11/2011 | Champagne |
| 2011/0282387 | A1 | 11/2011 | Suh |
| 2012/0029579 | A1 | 2/2012 | Bottlang |
| 2012/0041395 | A1 | 2/2012 | Sweeney |
| 2012/0123474 | A1 | 5/2012 | Zajac |
| 2012/0150237 | A1 | 6/2012 | Combrowski |
| 2012/0172936 | A1 | 7/2012 | Horrell |
| 2012/0209332 | A1 | 8/2012 | Janowski |
| 2012/0271416 | A1 | 10/2012 | Mackay |
| 2013/0030480 | A1 | 1/2013 | Donate |
| 2013/0090691 | A1 | 4/2013 | Zhang et al. |
| 2013/0131733 | A1 | 5/2013 | Chien |
| 2013/0178901 | A1 | 7/2013 | Arai |
| 2013/0184708 | A1 | 7/2013 | Robinson et al. |
| 2013/0317503 | A1 | 11/2013 | Songer |
| 2014/0025166 | A1 | 1/2014 | Bonutti |
| 2014/0121711 | A1 | 5/2014 | Worcel |
| 2014/0214095 | A1 | 7/2014 | Rosenwasser |
| 2014/0228866 | A1 | 8/2014 | Fallin et al. |
| 2014/0243977 | A1 | 8/2014 | Tepic |
| 2014/0276894 | A1 | 9/2014 | Ramsay et al. |
| 2014/0277444 | A1 | 9/2014 | Clifford et al. |
| 2015/0051601 | A1 | 2/2015 | Larsen et al. |
| 2015/0073475 | A1 | 3/2015 | Schaller |
| 2015/0081019 | A1 | 3/2015 | Whittaker |
| 2015/0272646 | A1 | 10/2015 | Russell |
| 2015/0289866 | A1 | 10/2015 | Bowen |
| 2015/0342656 | A1 | 12/2015 | Bertollo |
| 2016/0030035 | A1 | 2/2016 | Zajac et al. |
| 2016/0045636 | A1 | 2/2016 | Rizk et al. |
| 2016/0287301 | A1 | 10/2016 | Mehl et al. |
| 2016/0287302 | A1 | 10/2016 | Horrell et al. |
| 2016/0354183 | A1 | 12/2016 | Montero |
| 2016/0367303 | A1 | 12/2016 | Mahajan |
| 2016/0367341 | A1 | 12/2016 | Perez Yanini et al. |
| 2017/0079698 | A1 | 3/2017 | Fallin et al. |
| 2017/0079699 | A1 | 3/2017 | Fallin et al. |
| 2017/0112552 | A1 | 4/2017 | Sinnott et al. |
| 2017/0258572 | A1 | 9/2017 | Gordon |
| 2018/0078299 | A1 | 3/2018 | Rossney et al. |
| 2018/0092681 | A1 | 4/2018 | Lutz |
| 2018/0221072 | A1 | 8/2018 | P |
| 2018/0344374 | A1 | 12/2018 | Summitt |
| 2019/0083232 | A1 | 3/2019 | Dacosta et al. |
| 2019/0090926 | A1 | 3/2019 | Lutz et al. |
| 2019/0125420 | A1 | 5/2019 | Diaz et al. |
| 2019/0336190 | A1 | 11/2019 | Allard et al. |
| 2020/0323565 | A1 | 10/2020 | Childs |

FOREIGN PATENT DOCUMENTS

| | | |
|---|---|---|
| DE | 19943594 | 4/2001 |
| DE | 10015734 | 9/2001 |
| DE | 102010055433 | 6/2012 |
| GR | 20090100297 | 12/2010 |
| WO | 2006124987 | 11/2006 |
| WO | 2010121234 | 10/2010 |
| WO | 2013015754 | 1/2013 |
| WO | 2016133938 | 8/2016 |

OTHER PUBLICATIONS

Porucznik, "Screw vs. tightrope fixation for syndesmotic fractures," AAOS Now, http://www.aaos.org/news/aaosnow/may08/clinical4.asp, 3 pages, May 2008.

Xu et al., "Flexible fixation of syndesmotic diastasis using the assembled bolt-tightrope system," Scandinavian Journal of Trauma, Resuscitation and Emergency Medicine, vol. 21(71), 9 pages, Sep. 22, 2013.

"Interventional procedure overview of suture fixation of acute disruption of the distal tibiofibular syndesmosis," National Institute for Health and Care Excellence, www.nice.org.uk, 43 pages, Jul. 2014.

LIGAMENT FIXATION SYSTEM, IMPLANTS, DEVICES, AND METHODS OF USE

CROSS-REFERENCE TO RELATED APPLICATION

This is a continuation of U.S. application Ser. No. 17/249,205 filed on Feb. 23, 2021, which issues as U.S. Pat. No. 11,617,642 on Apr. 4, 2023, and which is a divisional of U.S. application Ser. No. 16/517,295 filed on Jul. 19, 2019, which issued as U.S. Pat. No. 10,945,830 on Mar. 16, 2021, and which is a continuation of PCT international patent application No. PCT/US2018/055028, filed Oct. 9, 2018, entitled Ligament Fixation System, Implants, Devices, and Methods of Use, which claims priority benefit of U.S. provisional application No. 62/569,238, filed Oct. 6, 2017, entitled Ligament Fixation System, Implants, Devices, and Methods of Use, which are hereby incorporated herein by reference in their entireties.

TECHNICAL FIELD

The present disclosure relates generally to general, podiatric, and orthopaedic surgery related to fixation of ligaments. More specifically, but not exclusively, the present disclosure relates to devices, systems, and methods for achieving dynamic ligament fixation.

BACKGROUND

Syndesmotic injuries are a result of trauma (not specific to sports injuries) and can occur as a purely ligamentous injury or in combination with an ankle fracture. These ligaments become disrupted, separated, or injured where semi-constrained approximation and fixation is needed to aide in healing without the need for a second surgery such as removal of a rigid fixation screw. The current standard of care for syndesmotic injuries involves either rigid fixation with a screw, or a tether-based constraint across the entire width of the ankle (TightRope, etc.).

The more rigid screw-based fixation is simple to implant and stabilizes the joint, but fails to allow any motion at all, as would normally exist physiologically. This limits the patient's range of motion, and unpredictable screw failure locations can result in damage to existing bone and patient pain.

Tethered constraints, such as the Arthrex Tightrope, do allow for motion of the joint, but by spanning the entire width of the ankle, fail to mimic the intact ligament structures of the syndesmosis in terms of attachment location and distance between the tibia and fibula. However, tethered constraints result in a necessary decrease in structural strength due to the surgical technique of the Tightrope and like devices involving drilling a hole through both the tibia and fibula which remains unfilled by structural material (e.g. a metal screw).

Thus, new and improved devices, systems, and methods for achieving ligament fixation are needed to overcome the above-noted drawbacks of the currently available solutions for addressing syndesmotic injuries.

SUMMARY

The present disclosure is directed toward devices and methods for use in ligament fixation. The devices, systems, and methods for achieving ligament fixation.

In one aspect of the present disclosure provided herein, is an implant. The implant including a head member and an anchor member coupled to the head member.

In another aspect of the present disclosure provided herein, is an insertion instrument. The insertion instrument, including a first shaft, a second shaft extending away from the first shaft, a first feature positioned at a first end of the second shaft; and a second feature positioned at the second end of the second shaft.

In yet another aspect of the present disclosure provided herein, is a system. The system including an implant with a head member and an anchor member coupled to the head member and an insertion instrument for coupling to the implant.

In a further aspect of the present disclosure provided herein, is a method for inserting an implant. The method including obtaining the implant. The implant including a head member and an anchor member coupled to the head member. The method also including engaging the implant with an insertion instrument and inserting the implant into a patient to position the head member in a first bone and the anchor member in a second bone.

In a further aspect of the present disclosure an implant is disclosed. The implant comprises a head member, an anchor member, and a tension member coupling the head member to the anchor member. The head member and the anchor member include a cannulation that receives the tension member therein.

In some embodiments, the head member directly engages the anchor member. In some embodiments, the implant further comprises a coupling member positioned between and coupling the head member and the anchor member. In some embodiments, the coupling member includes a cannulation that receives the tension member therethrough. In some embodiments, the head member comprises a first engagement protrusion, the anchor member comprises a second engagement protrusion, and the coupling member comprises a first engagement aperture that receives the first engagement protrusion of the head member and a second engagement aperture that receives the second engagement protrusion of the anchor member. In some embodiments, the first engagement protrusion, the second engagement protrusion, the first engagement aperture and the first engagement aperture define a non-circular cross-section. In some embodiments, the first engagement protrusion, the second engagement protrusion, the first engagement aperture and the first engagement aperture define a non-circular cross-section that includes a plurality of lobes with a recess extending between adjacent lobes.

In some embodiments, the cannulation of the head member extends through the first engagement protrusion, the cannulation of the anchor member extends through the second engagement protrusion, and the cannulation of the head member is in communication with the first and second engagement apertures. In some embodiments, the head member comprises a head portion and a shaft portion extending from the head portion, the head portion defining a free end of the implant. In some embodiments, the head portion includes a non-circular drive aperture and the shaft portion includes external threads. In some embodiments, the drive aperture is in communication with the cannulation of the head member.

In some embodiments, the cannulation of the head member includes a first enlarged portion positioned proximate to the head portion and a second narrow portion positioned distal to the head portion and proximate to the anchor member. In some embodiments, the implant further comprises a head post member positioned within the first enlarged portion of the cannulation of the head member, and the head post member is coupled to a first portion of the tension member. In some embodiments, the head post member comprises a cannulation, and the tension member extends at least partially through the cannulation of the head post member. In some embodiments, the head post member is coupled to the first portion of the tension member via at least one pin extending at least partially through the head post member and the tension member.

In some embodiments, the head post member is externally threaded, the cannulation of the head post member comprises an internally-threaded portion, and the head post member and the internally-threaded portion are threadably engaged. In some such embodiments, the first enlarged portion comprises the internally-threaded portion.

In some embodiments, the implant farther comprises at least one elastic member positioned within the first enlarged portion of the cannulation of the head member between the head post member and the second narrow portion of the cannulation of the head member. In some embodiments, the at least one elastic member comprises at least one disc spring, coil spring or elastic tube. In some embodiments, the at least one elastic member comprises a plurality of disc springs. In some embodiments, the plurality of disc springs include a plurality of adjacent disc springs oriented in the same axial direction and a plurality of adjacent disc springs oriented in opposing axial directions. In some embodiments, the plurality of adjacent disc springs oriented in opposing axial directions are elastically deformed and provide an assembly tension to the tension member that maintains head member and anchor member in engagement. In some embodiments, the plurality of adjacent disc springs oriented in the same axial direction and are elastically deformed after implantation of the implant to dissipate diastatic motion and/or pressure spikes. In some embodiments, the at least one elastic member is embedded in a bioresorbable material.

In some embodiments, the at least one elastic member comprises an elastic bumper member. In some such embodiments, the elastic bumper member defines a tube, and the tension member passes through an aperture of the tube. In some embodiments, the elastic bumper member is formed of thermoplastic urethane, polycarbonate urethane or a combination thereof.

In some embodiments, the anchor member comprises an externally threaded portion and a non-threaded crimp portion, the non-threaded crimp portion defining a free end of the implant. In some embodiments, the implant further comprises a tip post member positioned within the cannulation of the anchor member, the tip post member coupled to a second portion of the tension member. In some embodiments, the tip post member comprises a cannulation, and the tension member extends at least partially through the cannulation of the tip post member. In some embodiments, the tip post member is coupled to the second portion of the tension member via at least one pin extending at least partially through the tip post member and the tension member. In some embodiments, the tip post member comprises a hook slot extending from an end of the tip post member positioned proximate to the free end of the implant defined by the crimp portion. In some embodiments, the tip post member comprises a recess in an outer surface thereof, the recess configured to accept a deformed portion of the crimp portion of the anchor member therein to axially fix the tip post within the cannulation of the anchor member.

In some embodiments, the tension member is a suture. In some embodiments, the suture includes a loop. In some embodiments, the suture is a bifurcated suture that forms a loop portion positioned between first and second non-bifurcated end portions. In some embodiments, the first non-bifurcated end portion of the suture is coupled to the head member and the second non-bifurcated end portion of the suture is coupled to the anchor member. In some embodiments, the tension member is made of a bioresorbable material. In some embodiments, the implant further comprises a coupling positioned between the head member and the anchor member, the tension member engaging channels in the spacer. In some embodiments, the coupling is made of a bioresorbable material.

In a further aspect of the present disclosure, a method of inserting an implant is provided. The method comprises obtaining an implant, the implant comprises an implant provided herein. The method also comprises engaging the implant with an insertion instrument, and inserting the implant into a patient to position the head member in a first bone and the anchor member in a second bone.

In some embodiments, the first bone is a fibula and the second bone is a tibia. In some embodiments, the implant is inserted as a one-piece construct. In some embodiments, the implant allows for motion between the first bone and the second bone.

In a further aspect of the present disclosure, an insertion instrument is provided. The instrument comprises a first shaft, a second shaft extending away from the first shaft, a first feature positioned at a first end of the second shaft, and a second feature positioned at the second end of the second shaft.

In a further aspect of the present disclosure, a system is provided. The system comprises an implant comprising an implant and an insertion instrument for coupling to the implant, the implant comprises an implant provided herein.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

DETAILED DESCRIPTION

Generally stated, disclosed herein are devices and systems for achieving ligament fixation. Further, methods for using the devices and systems to achieve ligament fixation are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation and methods are described herein with reference to use with the bones of the ankle, the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the implants, devices, instrumentation and methods, and the aspects, components, features and the like thereof, described herein with respect to the right leg may be mirrored so that they likewise function with the left leg. Further, the implants, devices, instrumentation and methods, and the aspects, components, features and the like thereof, disclosed herein are described with respect to the leg for brevity purposes, but it should be understood that the implants, devices, instrumentation and methods may be used with other bones of the body having similar structures.

Figure 1:
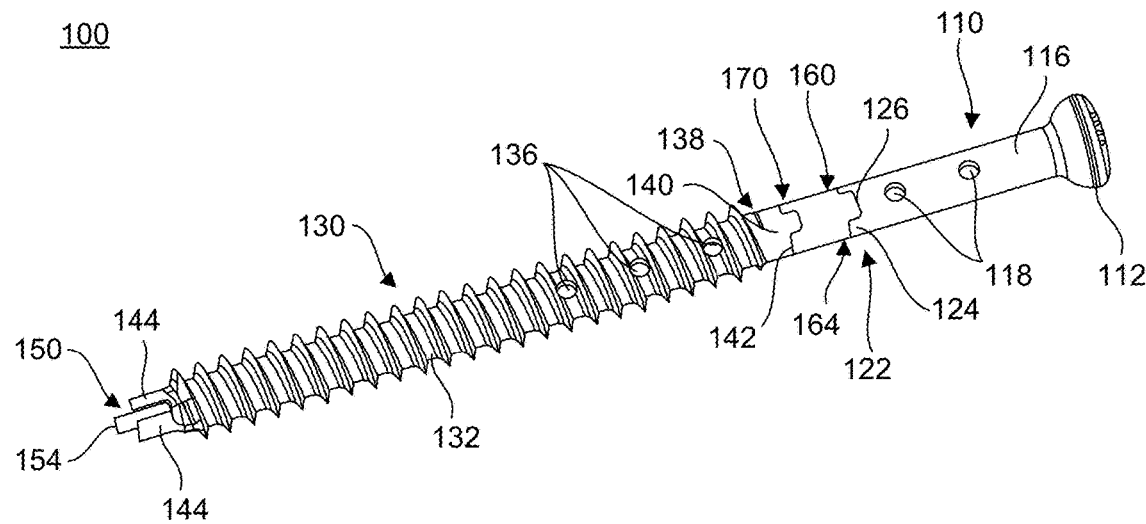
FIG. 1 is a side perspective view of one embodiment of an implant, in accordance with an aspect of the present disclosure.
Figure 2:
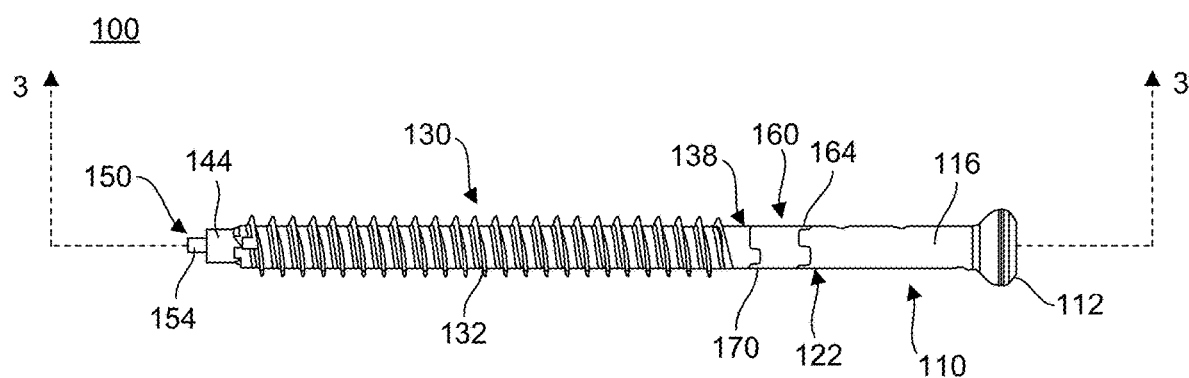
FIG. 2 is a side view of the implant of FIG. 1, in accordance with an aspect of the present disclosure.
Figure 87:
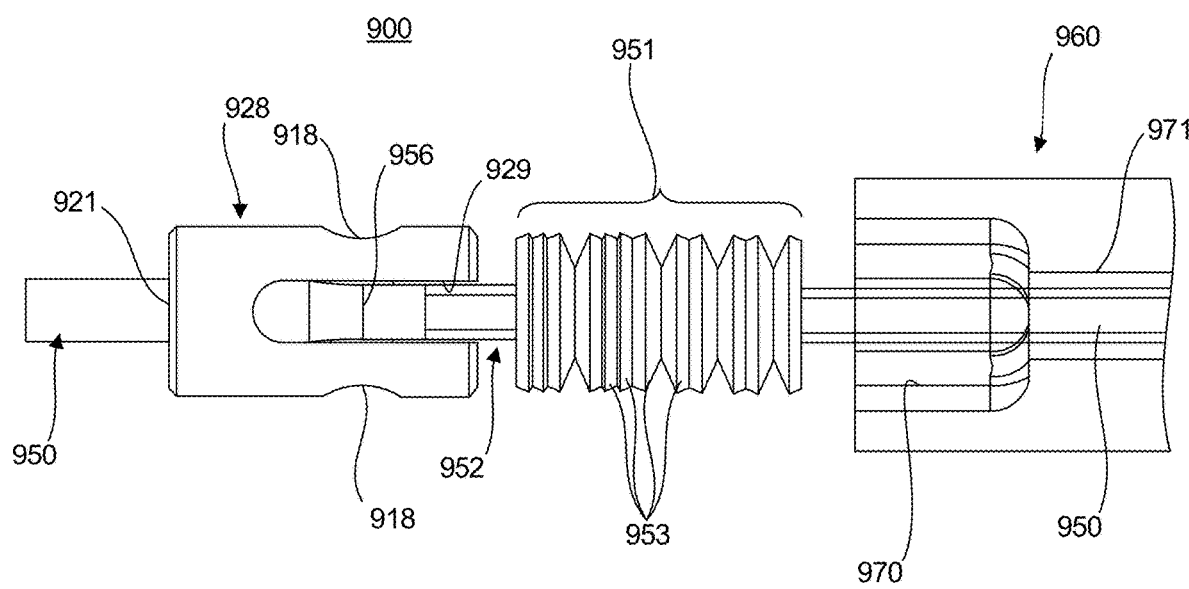
FIG. 87 is a side view of the implant of FIG. 62, illustrating the tension member, head post, resilient member and coupling in a partially-assembled configuration, in accordance with an aspect of the present disclosure.
Figure 88:
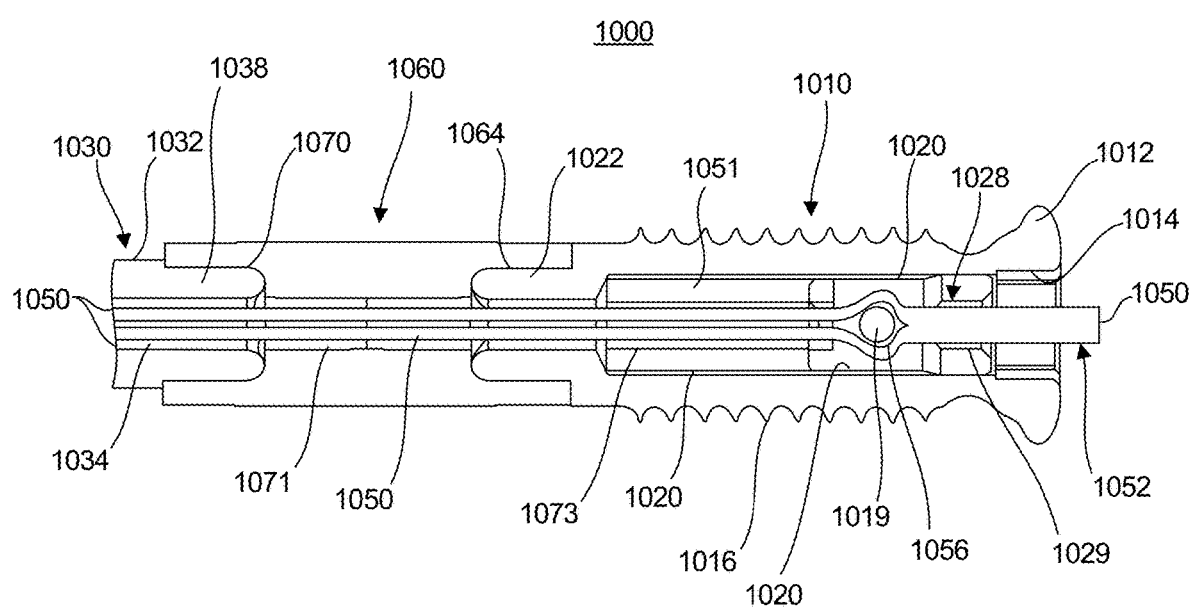
FIG. 88 is a side cross-sectional view of a portion of another implant, in accordance with an aspect of the present disclosure.
Figure 89:
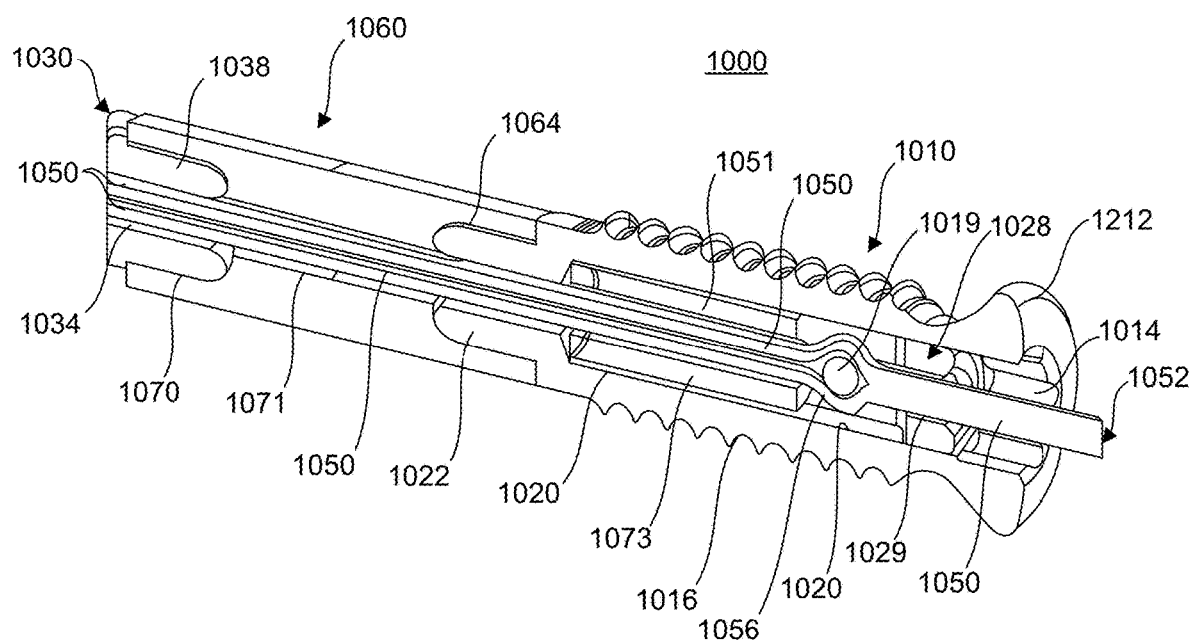
FIG. 89 is a side cross-sectional perspective view of a portion of the implant of FIG. 88, in accordance with an aspect of the present disclosure.
Figure 90:
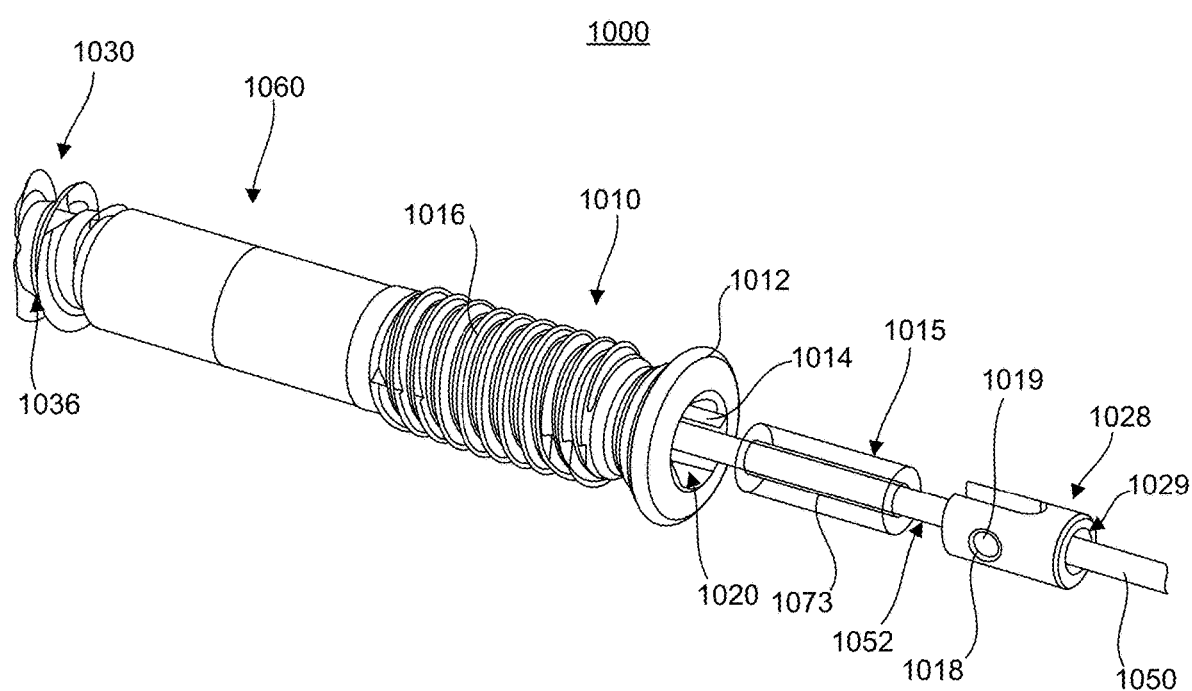
FIG. 90 is a side perspective view of a portion of the implant of FIG. 88 illustrating an elastic member, a head post and a tension member thereof in an exploded arrangement, in accordance with an aspect of the present disclosure.
Figure 91:
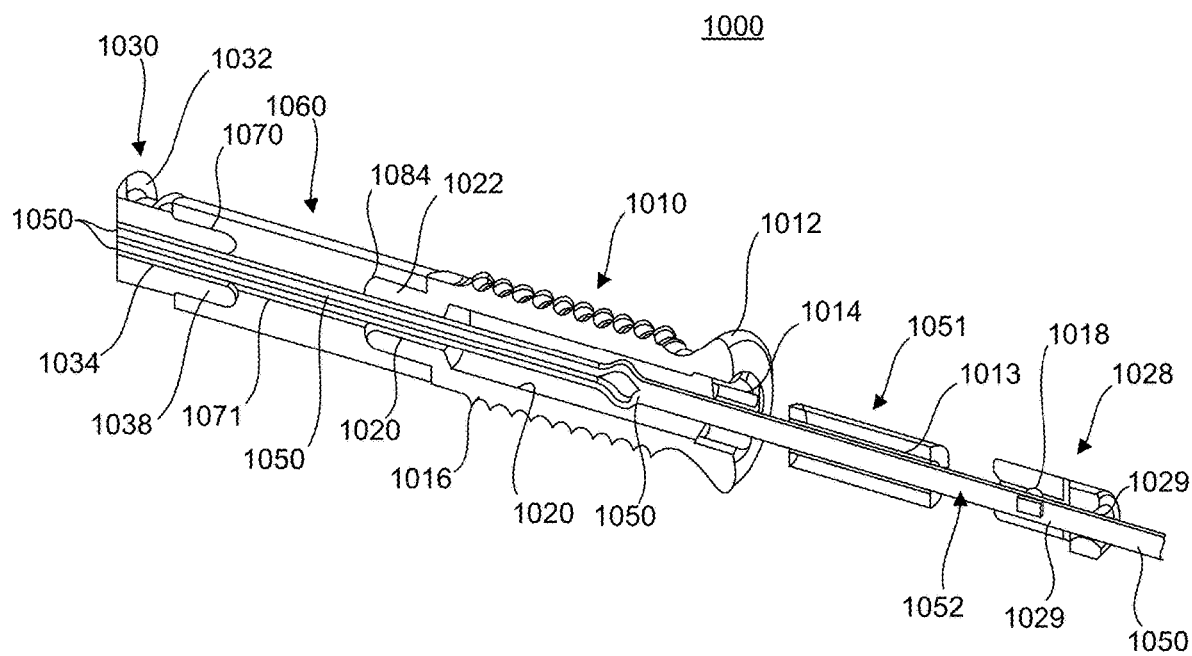
FIG. 91 is a side cross-sectional perspective view of a portion of the implant of FIG. 88 illustrating the elastic member, the head post and the tension member thereof in an exploded arrangement, in accordance with an aspect of the present disclosure.

Referring to the drawings, wherein like reference numerals are used to indicate like or analogous components throughout the several views, and with particular reference to FIGS. 1-87, there is illustrated implants 100, 300, 400, 500, 600, 700 and 900. The implants 100, 300, 400, 500, 600, 700 and 900 may be, for example, supportive enough to heal syndesmotic ligaments post-operatively. The implants 100, 300, 400, 500, 600, 700 and 900 may also, for example, selectively constrain motion in all directions to allow for the ligaments to heal. After the syndesmotic ligaments heal, the implants 100, 300, 400, 500, 600, 700 and 900 allow for physiologic motion. In addition, the implants 100, 300, 400, 500, 600, 700 and 900 re-create pressure in the lateral gutter. The components of the implants 100, 300, 400, 500, 600, 700 and 900 may be made of, for example, titanium, stainless steel, polymers, polyester or UHMWPE suture, resorbable suture, co-braids thereof, thermoplastic urethane bumper, and resorbable time release materials or polymers.

The implants 100, 300, 700 and 900 also allow for screw-like implantation and temporary rigid fixation, then, after insertion, the implants 100, 300, 700 and 900 transition to semi-constrained motion. The implants 400, 500, 600 allow for screw-like implantation, and allow semi-constrained motion without a period of rigid fixation. The temporary rigid fixation of the implants 100, 300, 700 and 900 gives the fixed joint time to stabilize through healing and then allows physiologic motion. The area of allowed motion in implants 100, 300, 400, 500, 600, 700 and 900 is set in the space or gap between the fibula and tibia, where the subsequent risk of damage to native bone is lower. The tension member or tether 150, 310, 410, 550, 640, 800, 850 mimics the interosseous ligament in both location and length. In addition, the components in the tibia and fibula protect native bone from abrasion from the tension members 150, 310, 410, 550, 640, 800, 850, 950 and vice versa. The surgical method includes drilling a hole through both the tibia and fibula and then inserting an implant 100, 300, 400, 500, 600, 700 or 900 sized to fill the bone holes or cavities to provide a stronger post-op construct.

Referring now to FIGS. 1-11, the implant 100 is illustrated. The implant 100 includes a head member or fibula member 110, an anchor member or tibia member 130, a tension member 150, and a coupling 160. The coupling 160 may be positioned between the head member 110 and the anchor member 130 and allow for the anchor member 130 to be secured into the bones 180, 182 when the head member 110 is rotated. The tension member 150 may extend through a center of at least a portion of the aligned head member 110, the coupling 160, and at least a portion of the anchor member 130. The implant 100 may have a length of, for example, approximately 40 mm to 70 mm. In one embodiment, the lengths of the head member 110 and the coupling 160 may remain constant, while the length of the anchor member 130 may be variable to correspond to the varying size of a patient's bones 180, 182. Alternatively, in another embodiment, the head member 110 may, for example, be available in multiple lengths to correspond to the varying sizes of patient bones 180, 182 and the lengths of the anchor member 130 and the coupling 160 may remain constant. In yet another embodiment, both the head member 110 and the anchor member 130 may be available in multiple lengths to allow for selection based on the size of the patient's bones 180, 182 and the coupling 160 may remain constant. Therefore, the head member 110 may have a length of, for example, between approximately 10 mm and 20 mm, the anchor member 130 may have a length of, for example, between approximately 20 mm and 60 mm, and the coupling 160 may have a length of, for example, approximately 3 mm.

Figure 5:
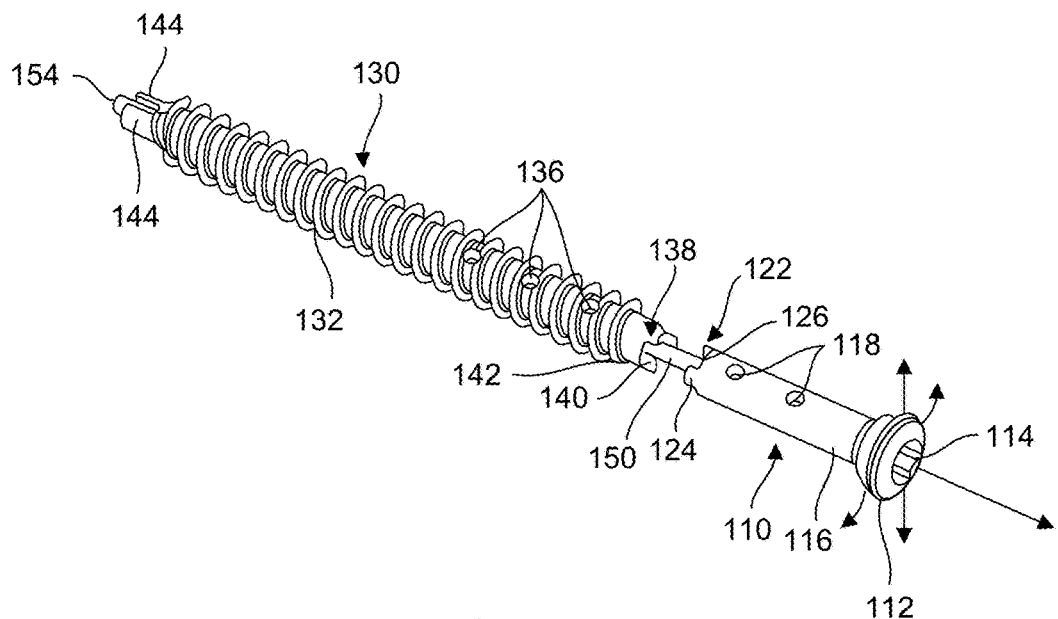
FIG. 5 is a perspective view of the implant of FIG. 1 after the bioresorbable drive coupling of the implant is absorbed, in accordance with an aspect of the present disclosure.
Figure 6:
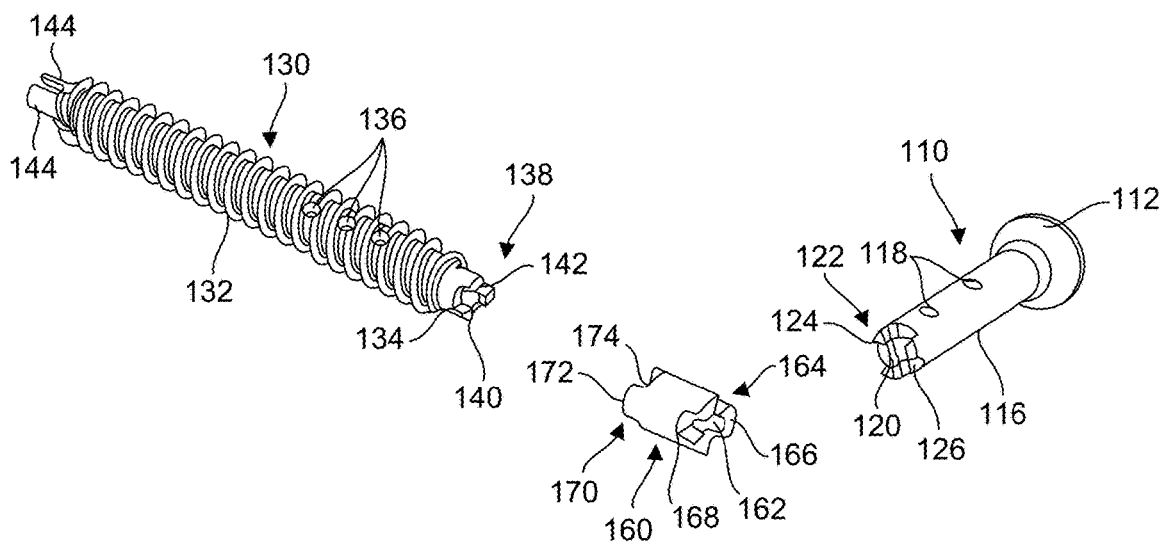
FIG. 6 is an exploded side view of the head member, the anchor member, and the drive coupling of the implant of FIG. 1, in accordance with an aspect of the present disclosure.

As shown in at least FIGS. 5 and 6, the head member 110 includes a shaft member 116 with a head or button 112 at a first end and an engagement end or mating jaw 122 at the second end. The head 112 may include a tool engagement opening 114 positioned opposite the shaft member 116. The tool engagement opening 114 may have, for example, a multi-lobed shape as shown in FIG. 5, although other polygonal shapes are also contemplated, including a hexagonal shape or a hexalobular drive feature. The shaft member 116 may include at least one transverse opening 118 and a through hole or cannulated opening 120. The cannulated opening 120 may extend through the entire head member 110 along the longitudinal axis of the head member 110. The at least one opening 118 may extend perpendicular to the cannulated opening 120 and may extend from an exterior surface of the head member 110 at least into the cannulated opening 120.

Figure 3:
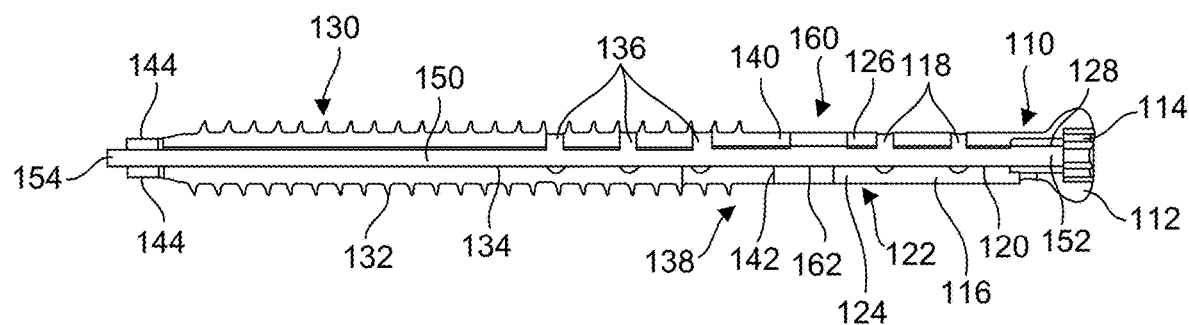
FIG. 3 is a first cross-sectional view of the implant of FIG. 1 taken along line 3-3 in FIG. 2, in accordance with an aspect of the present disclosure.
Figure 4:
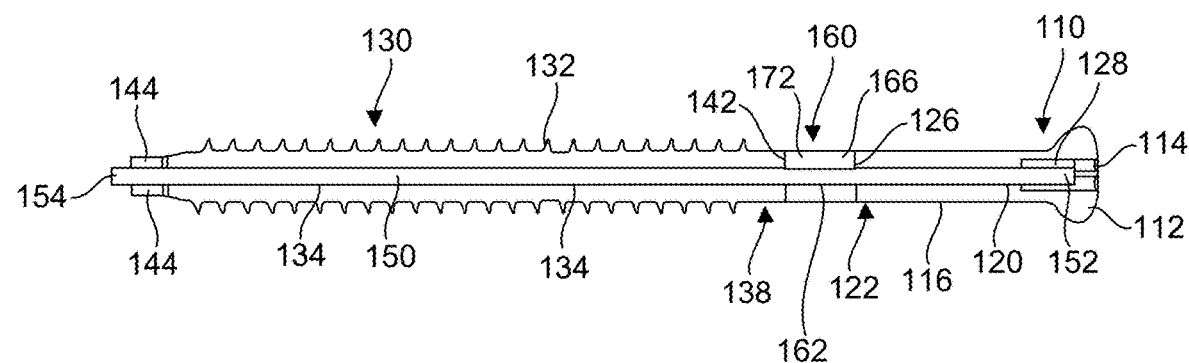
FIG. 4 is a second cross-sectional view of the implant of FIG. 1 taken along a longitudinal line perpendicular to line 3-3 in FIG. 2, in accordance with an aspect of the present disclosure.

The engagement end 122 may include at least one protrusion or tooth 124 and at least one groove or recess 126, as shown in FIG. 6. For example, in the depicted embodiment, the engagement end 122 includes three protrusions 124 alternating with three recesses 126. The head member 110 may also include an internal crimping feature 128, for example, a crimp ferrule positioned within the through hole 120 near the head 112, as shown in FIGS. 3 and 4. The crimping feature 128 may secure a first end 152 of the tension member 150 to the head member 110. Alternatively, the head member 110 may include slots, windows, recesses, apertures (not shown) inset into the interior diameter of the opening 120 and positioned opposite the openings 118. The slots (not shown) may be sized and shaped to receive a pin or engagement member (not shown). The pin (not shown) may be inserted through the openings 118 to engage the tension member 150 and push a portion of the tension member 150 into the opposing slots (not shown) securing the tension member 150 to the head member 110. The slots (not shown) may be, for example, slightly offset from the openings 118 to provide additional securement of the tension member 150 to the head member 110. The pins (not shown) may also be coupled to the head member 110 by, for example, laser welding to prevent a pin from disengaging the head member 110 after insertion into a patient. The head member 110 may be made of, for example, titanium, stainless steel, polymer, or another like material as would be known by one of ordinary skill in the art. Although not shown, the head member 110 may, for example, also optionally be threaded on at least a portion of the exterior surface between the head 112 and the engagement end 122.

With continued reference to FIGS. 5 and 6, the anchor member 130 may include a threaded shaft 132 with an engagement end or mating jaw 138 at a first end and at least one crimp member 144 at a second end. The threaded shaft 132 may be, for example, threaded along the entire length of the shaft or only along a portion of the shaft. The threaded shaft 132 may also include a through hole or cannulated opening 134 extending from the first end to the second end along the longitudinal axis of the anchor member 130. The threaded shaft 132 may also include at least one transverse opening 136 extending from an exterior surface of the threaded shaft 132 into the through hole 134. The engagement end or mating jaw 138 may include at least one protrusion or tooth 140 and at least one groove or recess 142, as shown in FIG. 6. For example, in the depicted embodiment, the engagement end 138 includes three protrusions 140 alternating with three recesses 142. Although not shown, it is also contemplated that the second end of the anchor member 130 may include at least one cutting element, for example, at least one cutting flute, such as the cutting flutes on the insertion end 536, as shown in FIGS. 24-32. The at least one cutting element may be, for example, four cutting flutes. It is also contemplated that the cutting flutes at the insertion end may be used as a removal feature if a medial approach is used to remove at least the anchor member 130.

The at least one crimp member 144 may be, for example, two crimp members 144 spaced apart and surrounding the cannulated opening 134 of the anchor member 130, as shown in FIGS. 1, 5 and 6. The at least one crimp member 144 may engage the tension member 150 to secure the tension member 150 to the anchor member 130. Alternatively, the anchor member 130 may include slots, windows, recesses, apertures (not shown) inset into the interior diameter of the opening 134 and positioned opposite the openings 136. The slots (not shown) may be sized and shaped to receive a pin or engagement member (not shown). The pin (not shown) may be inserted through the openings 136 to engage the tension member 150 and push a portion of the tension member 150 into the opposing slots (not shown) securing the tension member 150 to the anchor member 130. The slots (not shown) may be, for example, slightly offset from the openings 136 to provide additional securement of the tension member 150 to the anchor member 130. The pins (not shown) may also be coupled to the anchor member 130 by, for example, laser welding to prevent a pin from disengaging the anchor member 130 after insertion into a patient. The anchor member 130 may be made of, for example, titanium, stainless steel, polymer, and like materials as known by one of ordinary skill in the art.

Referring now to FIGS. 3-5, the tension member 150 may include a first end 152 and a second end 154. The first end 152 may be, for example, positioned within the cannulated opening 120 of the head member 110. The first end 152 may be secured to the head member 110 by, for example, an internal crimping feature or crimp ferrule 128 or, alternatively, pins (not shown) inserted through the at least one opening 118 to engage the tension member 150 and optionally an opposing slot (not shown) as described in greater detail above. The second end 154 may, for example, extend through the anchor member 130 and be positioned between the at least one crimp member 144. The second end 154 may be secured to the anchor member 130 by, for example, the crimp members 144 or, alternatively, by at least one pin (not shown) inserted through the at least one opening 136 to engage the tension member 150 and optionally at least one opposing slot (not shown) as described in greater detail above. The tension member 150 may be, for example, a braided suture, such as a size #5-#9 braided suture. The tension member 150 may be, for example, a single cross-section strand of suture or multiple loops.

As shown in FIG. 6, the coupling 160 may include a first engagement end or first mating jaw 164 at a first end and a second engagement end or second mating jaw 170 at a second end. The coupling 160 may also include a through hole or cannulated opening 162 extending through the coupling 160 along a longitudinal axis of the coupling 160. The first engagement end 164 may include at least one protrusion or tooth 166 and at least one groove or recess 168, as shown in FIG. 6. For example, in the depicted embodiment, the first engagement end 164 includes three protrusions 166 alternating with three recesses 168. The second engagement end 170 may include at least one protrusion or tooth 172 and at least one groove or recess 174, as shown in FIG. 6. For example, in the depicted embodiment, the second engagement end 170 includes three protrusions 172 alternating with three recesses 174. The protrusions 172 may be spaced, for example, 3 mm apart. The coupling 160 may be made of, for example, a bioresorbable material, such as, PLLA, PGA, PLDA, PL-DLA, copolymers of each, resorbable calcium composites, and like materials as known by one of ordinary skill in the art.

As shown in FIGS. 1-4 and 6, the anchor member 130 is linked dynamically to the head member 110 by a tension member 150 and a coupling 160. The implant 100 may be assembled by inserting the engagement end 122 of the head member 110 with the first engagement end 164 of the coupling 160 and the engagement end 138 of the anchor member 130 with the second engagement end 170 of the coupling 160. The coupling 160 will be positioned between the head member 110 and the anchor member 130. With the cannulated openings 120, 134, 162 of the head member 110, anchor member 130 and coupling 160 aligned, the tension member 150 may be inserted into the cannulated openings 120, 134, 162. The tension member 150 may be secured to the head member 110 by securing or tightening the crimping feature 128 around the tension member 150 and/or inserting pins (not shown) through at least one opening 118 in the head member 110 to engage and secure the tension member 150. The tension member 150 may also be secured to the anchor member 130 by securing or tightening the crimp members 144 around the tension member 150 and/or by inserting pins (not shown) through the at least one opening 136 in the anchor member 130 to engage and secure the tension member 150.

Figure 7:
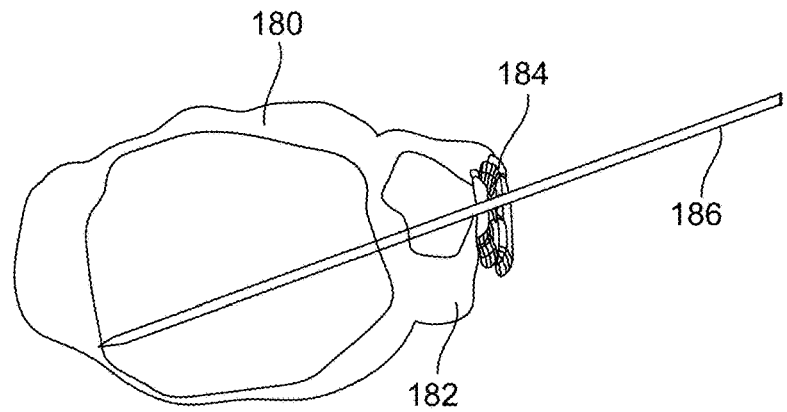
FIG. 7 is a distal, transverse planar view of a fibula and tibia with a k-wire inserted through a plate, the fibula and into the tibia, in accordance with an aspect of the present disclosure.
Figure 8:
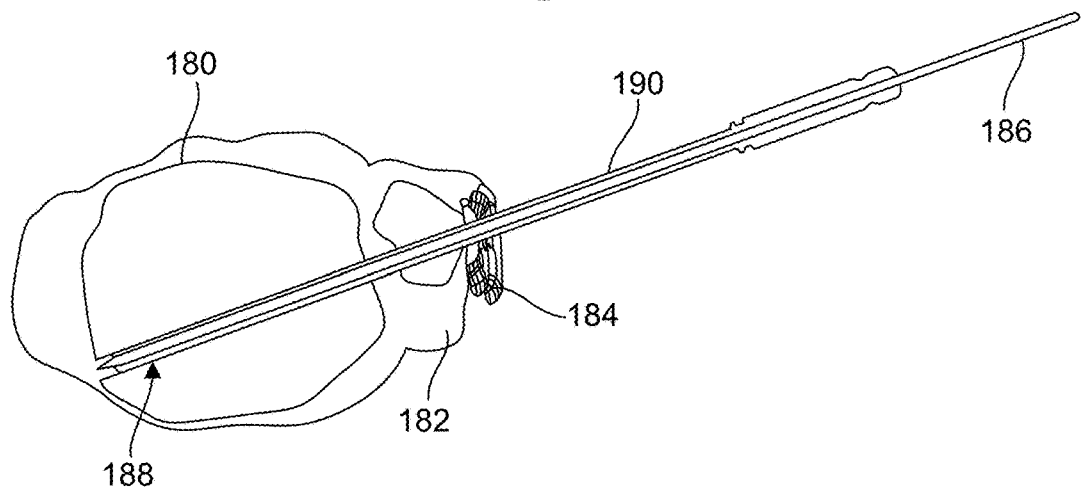
FIG. 8 is a distal, transverse planar view of the bones of FIG. 7 with a drill inserted over the k-wire of FIG. 7 through the plate, fibula and into the tibia, in accordance with an aspect of the present disclosure.
Figure 9:
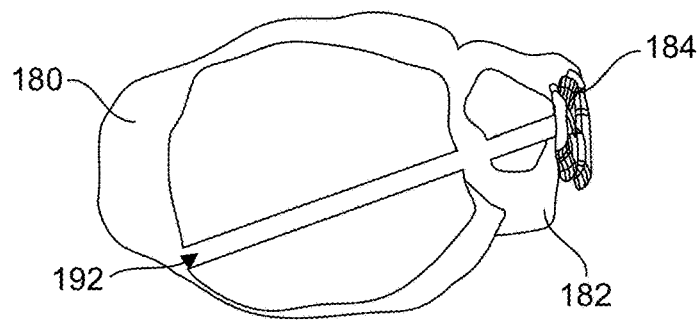
FIG. 9 is a distal, transverse planar view of the bones of FIG. 7 after the drill and k-wire are removed, in accordance with an aspect of the present disclosure.
Figure 10:
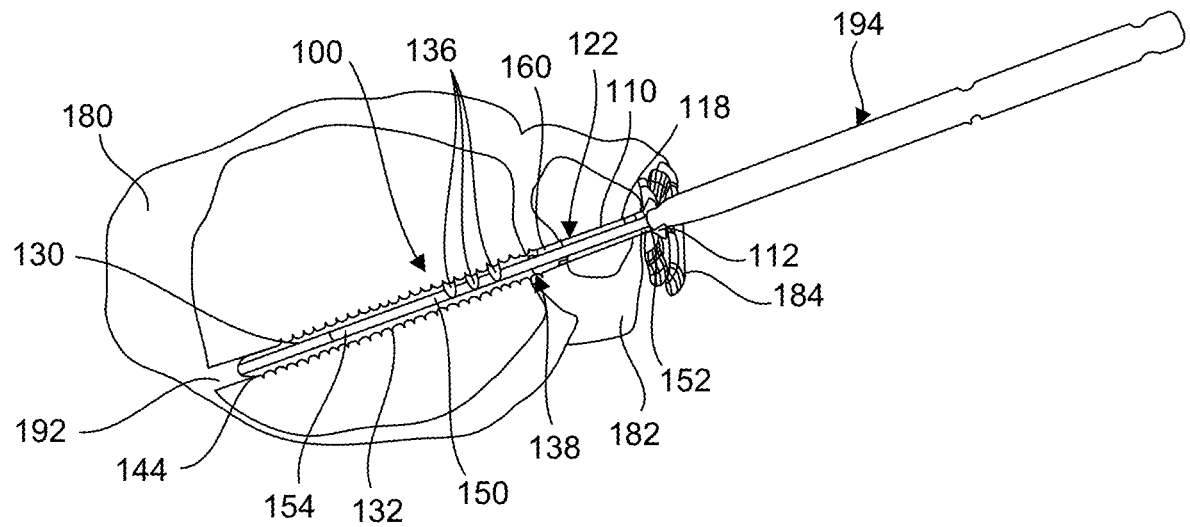
FIG. 10 is a distal, transverse planar view of the bones of FIG. 7 with the implant of FIG. 1 inserted into the drilled opening with a driver instrument, in accordance with an aspect of the present disclosure.
Figure 11:
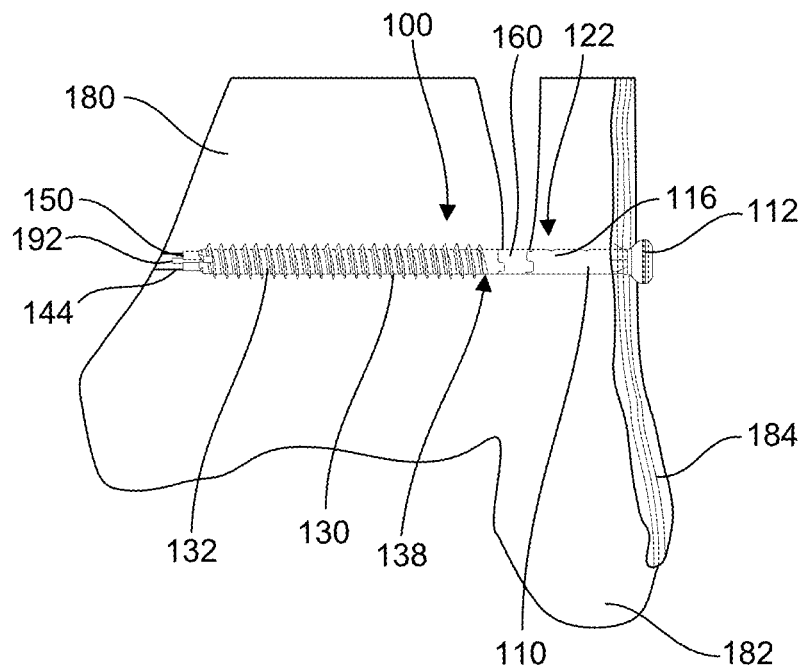
FIG. 11 is a posterior view of the bones of FIG. 7 with the implant of FIG. 1 inserted through the plate, fibula and into the tibia, in accordance with an aspect of the present disclosure.
Figure 12:
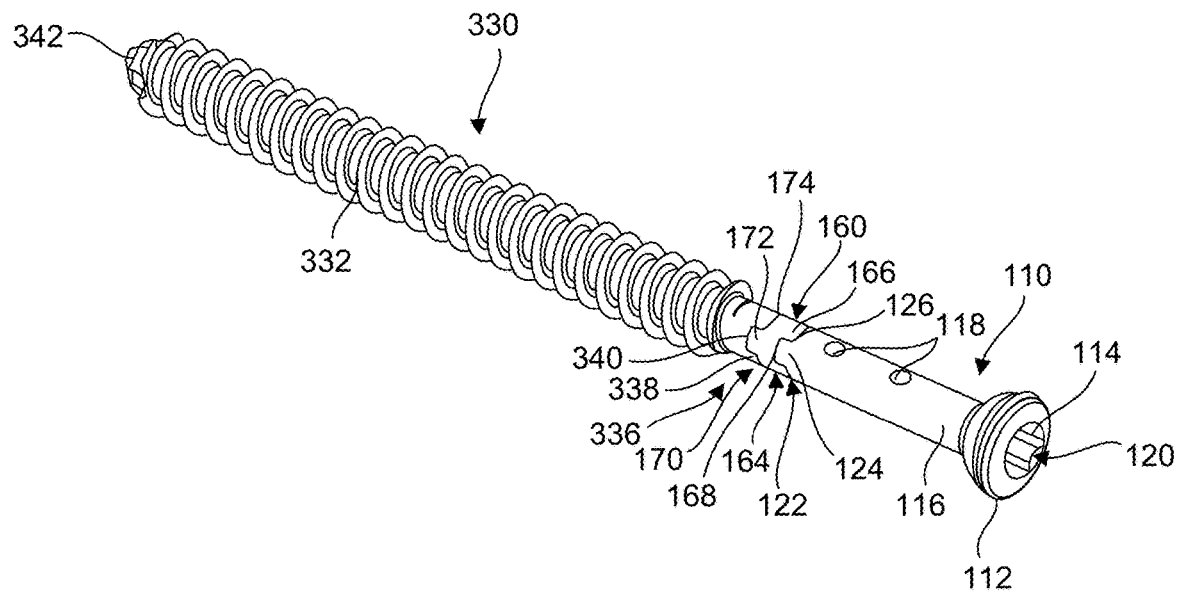
FIG. 12 is a perspective side view of yet another implant, in accordance with an aspect of the present disclosure.
Figure 13:
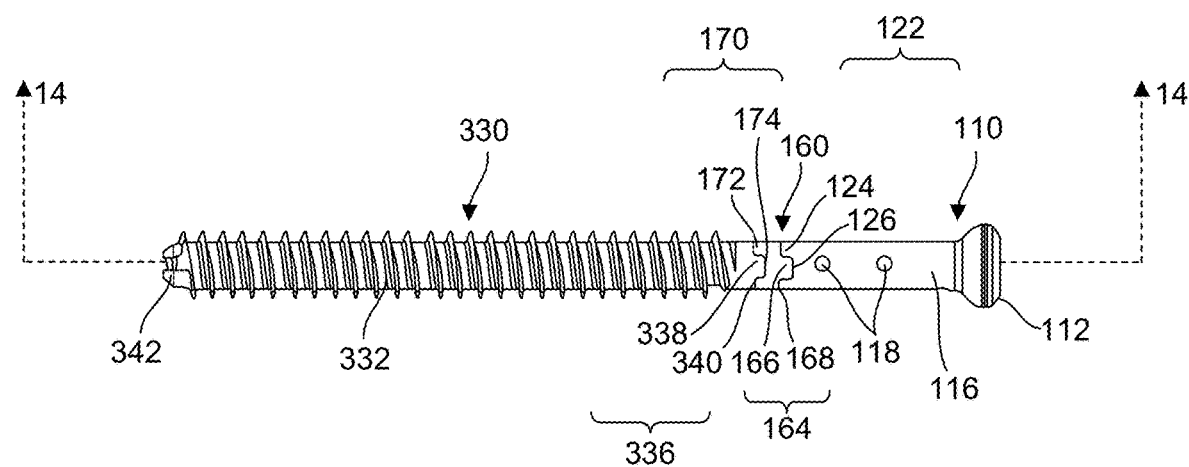
FIG. 13 is a side view of the implant of FIG. 12, in accordance with an aspect of the present disclosure.

Referring now to FIGS. 7-11, a method of inserting the implant 100 is shown. The method may optionally include positioning a plate 184 on a bone 182, for example, a fibula. The method may also include driving a k-wire or guide wire 186 through two bones 180, 182, for example, a fibula 182 and tibia 180, as shown in FIG. 7. Next, as shown in FIG. 8, a drill 188 may be inserted over the k-wire 186 by aligning a cannulated opening 190 in the drill 188 with the k-wire 186. The drill 188 may be used to drill an opening 192 through the bones 180, 182. The opening 192 may have a diameter, for example, that corresponds to the minor diameter of the anchor member 130. After the opening 192 is drilled, the drill 188 and optionally the k-wire 186 may be removed from the bones 180, 182, as shown in FIG. 9. Optionally, after removing the drill 188 and prior to removing the k-wire 186, measurements of the depth of the opening 192 may be taken using a cannulated depth gauge (not shown) inserted over the k-wire 186. Once the measurements are taken, the k-wire 186 may then be removed. Alternatively, the k-wire 186 may be removed from the bones 180, 182 and a standard depth gauge (not shown) may be used to take the measurements. For example, an overall or first depth measurement of the opening or drill hole 192, such as a measurement to the far cortex of the tibia, may be taken using a cannulated depth gauge, standard depth gauge or other like instrument. The surgeon may also take a second depth measurement of the portion of the opening 192 in the fibula using, for example, a standard depth gauge or like instrument, to determine the size of the head member 110. Then, an instrument 194 may be used to insert the implant 100 into the opening 192 in the bones 180, 182, as shown in FIG. 10. The implant 100 may be inserted to position the anchor member 130 in the tibia 180, the head member 110 in the fibula 182, and the coupling 160 in a tibiofibular clear space or gap, as shown in FIG. 11. The torsional force applied to the head member 110 for inserting the implant 100 may be transmitted to the anchor member 130 through the coupling 160. Next, the instrument 194 may be removed from head member 110 of the implant 100, as shown in FIG. 11, and the surgical procedure may be completed.

After inserting the implant 100, the coupling 160 will eventually fail leaving the head member 110 coupled to the anchor member 130 by only the tension member 150, as shown in FIG. 5. The coupling 160 may fail, for example, after at least a portion of the coupling 160 is resorbed into the patient. Failure of the coupling 160 will allow for semi-constrained motion between the tibia 180 and fibula 182 via the tension member 150. The flexibility of the tension member 150 may allow for diastatic motion of the implant 100. Thus, the implant 100 allows for the patient's physiologic motion to be restored in an anterior-posterior direction, a superior-inferior direction, as well as allowing for fibular rotation, at the joint based on the strength of the tension member 150 and the resorbable coupling 160.

Referring now to FIGS. 56-61, the implant 200 is illustrated. The implant 200 includes a head member or fibula member 210, an anchor member or tibia member 230, a tension member 250, and a coupling 260. The coupling 260 may be positioned between the head member 210 and the anchor member 230 and allow for the anchor member 230 to be secured into the bones 180, 182 when the head member 210 is rotated. The tension member 250 may extend through a center of at least a portion of the aligned head member 210, the coupling 260, and at least a portion of the anchor member 230. The implant 200 may have a length of, for example, approximately 40 mm to 70 mm. In one embodiment, the lengths of the head member 210 and the coupling 260 may remain constant, while the length of the anchor member 230 may be variable to correspond to the varying size of a patient's bones 180, 182. Alternatively, in another embodiment, the head member 210 may, for example, be available in multiple lengths to correspond to the varying sizes of patient bones 180, 182 and the lengths of the anchor member 230 and the coupling 260 may remain constant. In yet another embodiment, both the head member 210 and the anchor member 230 may be available in multiple lengths to allow for selection based on the size of the patient's bones 180, 182 and the coupling 260 may remain constant. Therefore, the head member 210 may have a length of, for example, between approximately 10 mm and 20 mm, the anchor member 230 may have a length of, for example, between approximately 20 mm and 60 mm, and the coupling 260 may have a length of, for example, approximately 3 mm.

As shown in at least FIGS. 56-60, the head member 210 includes a threaded shaft member 216 with a head or button 212 at a first end and an engagement end or mating jaw 222 at the second end. The head 212 may include a tool engagement opening 214 positioned opposite the shaft member 216. The tool engagement opening 214 may have, for example, a multi-lobed shape or other polygonal shape, including a hexagonal shape or a hexalobular drive feature. The shaft member 216 may include at least one transverse opening 218 and a through hole or cannulated opening 220. The cannulated opening 220 may extend through the entire head member 210 along the longitudinal axis of the head member 210. The at least one opening 218 may extend perpendicular to the cannulated opening 220 and may extend from an exterior surface of the head member 210 at least into the cannulated opening 220.

Figure 59:
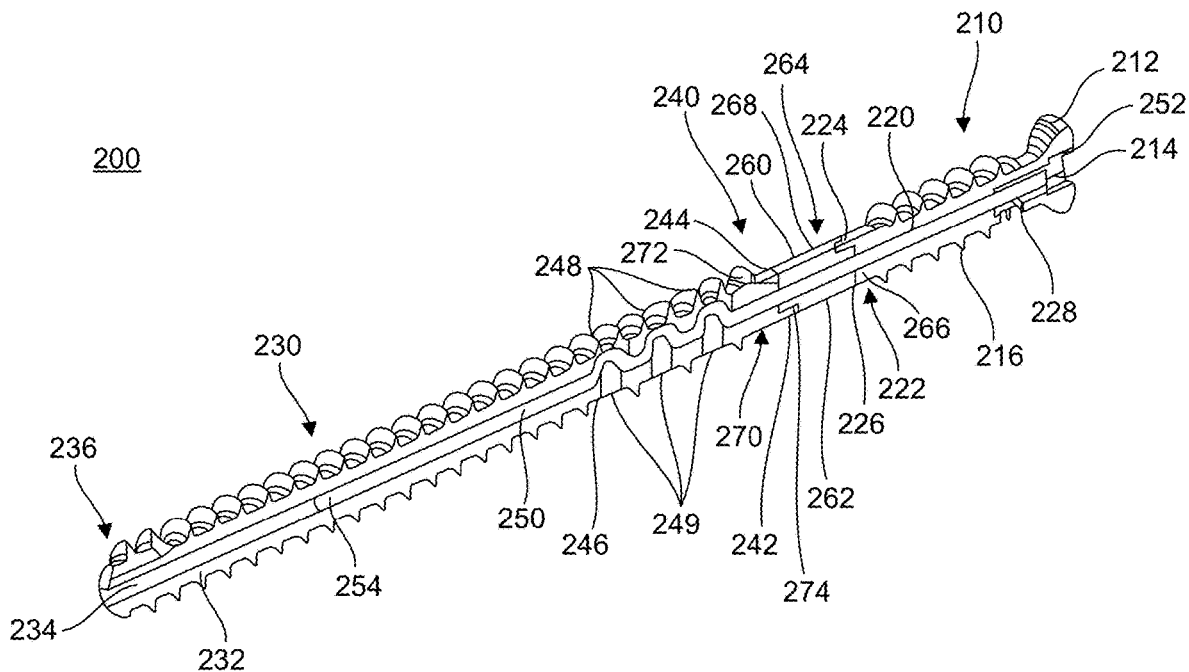
FIG. 59 is a perspective, cross-sectional view of the implant of FIG. 56 taken along line 59-59 in FIG. 57, in accordance with an aspect of the present disclosure.
Figure 60:
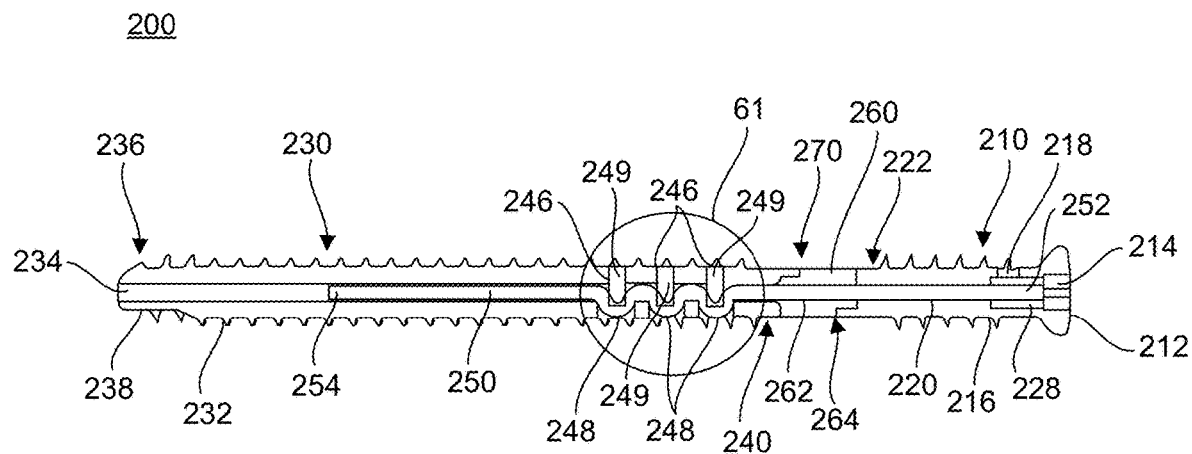
FIG. 60 is a side, cross-sectional view of the implant of FIG. 56 taken along line 59-59 in FIG. 57, in accordance with an aspect of the present disclosure.
Figure 61:
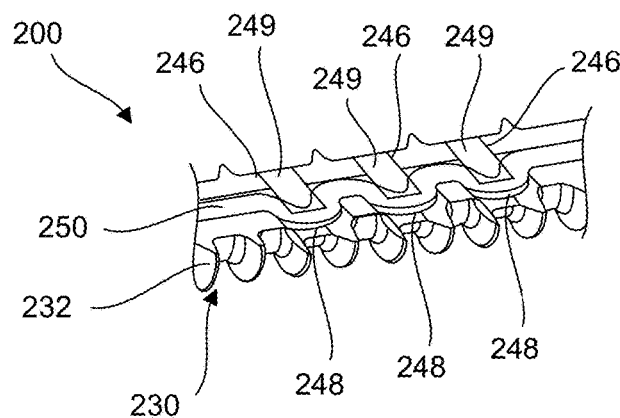
FIG. 61 is a perspective view of a portion of the implant of FIG. 60, in accordance with an aspect of the present disclosure.

The engagement end 222 may include at least one protrusion or tooth 224 and at least one groove or recess 226, as shown in FIGS. 56-60. For example, the engagement end 222 may include three protrusions 224 alternating with three recesses 226. The head member 210 may also include an internal crimping feature 228, for example, a crimp ferrule positioned within the through hole 220 near the head 212, as shown in FIGS. 59 and 60. The crimping feature 228 may secure a first end 252 of the tension member 250 to the head member 210. Alternatively, the head member 210 may include slots, windows, recesses, apertures (not shown) inset into the interior diameter of the opening 220 and positioned opposite the openings 218. The slots (not shown) may be sized and shaped to receive a pin or engagement member (not shown). The pin (not shown) may be inserted through the openings 218 to engage the tension member 250 and push a portion of the tension member 250 into the opposing slots (not shown) securing the tension member 250 to the head member 210. The slots (not shown) may be, for example, slightly offset from the openings 218 to provide additional securement of the tension member 250 to the head member 210. The pins (not shown) may also be coupled to the head member 210 by, for example, laser welding to prevent a pin from disengaging the head member 210 after insertion into a patient. The head member 210 may be made of, for example, titanium, stainless steel, polymer, or another like material as would be known by one of ordinary skill in the art. Although not shown, the head member 210 may, for example, also optionally be threaded on at least a portion of the exterior surface between the head 212 and the engagement end 222.

With continued reference to FIGS. 56-61, the anchor member 230 may include a threaded shaft 232 with an engagement end or mating jaw 240 at a first end and an insertion end 236 at a second end. The insertion end 236 may also include at least one cutting element 238, for example, at least one cutting flute, as shown in at least FIGS. 56-58. The at least one cutting element may be, for example, four cutting flutes. It is also contemplated that the cutting flutes at the insertion end may be used as a removal feature if a medial approach is used to remove at least the anchor member 230. The threaded shaft 232 may be, for example, threaded along the entire length of the shaft or only along a portion of the shaft. The threaded shaft 232 may also include a through hole or cannulated opening 234 extending from the first end to the second end along the longitudinal axis of the anchor member 230. The engagement end or mating jaw 240 may include at least one protrusion or tooth 242 and at least one groove or recess 244, as shown in FIGS. 56-60. For example, the engagement end 240 may include three protrusions 242 alternating with three recesses 244.

The threaded shaft 232 may also include at least one transverse opening 246 extending from an exterior surface of the threaded shaft 232 into the through hole 234. The anchor member 230 may include slots, windows, recesses, apertures 248 inset into the interior diameter of the opening 234 or extending from an exterior surface of the threaded shaft 232 into the through hole 234. The slots 248 may be positioned, for example, opposite the openings 246. The slots 248 may be sized and shaped to receive a pin or engagement member 249. The pin 249 may be inserted through the openings 246 to engage the tension member 250 and push a portion of the tension member 250 into the opposing slots 248 securing the tension member 250 to the anchor member 230, as shown in FIGS. 59 and 60. Although not shown, the slots 248 may be, for example, slightly offset from the openings 246 to provide additional securement of the tension member 250 to the anchor member 230. The pins 249 may also be coupled to the anchor member 230 by, for example, laser welding to prevent a pin from disengaging the anchor member 230 after insertion into a patient. The anchor member 230 may be made of, for example, titanium, stainless steel, polymer, and like materials as known by one of ordinary skill in the art.

Referring now to FIGS. 59 and 60, the tension member 250 may include a first end 252 and a second end 254. The first end 252 may be, for example, positioned within the cannulated opening 220 of the head member 210. The first end 252 may be secured to the head member 210 by, for example, an internal crimp ferrule 228 or, alternatively, pins (not shown) inserted through the at least one opening 218 to engage the tension member 250 and optionally an opposing slot (not shown) as described in greater detail above. The second end 254 may, for example, extend through a portion of the anchor member 230. The second end 254 may be secured to the anchor member 230 by, for example, at least one pin 249 inserted through the at least one opening 246 to engage the tension member 250 and at least one opposing slot 248 as described in greater detail above. The tension member 250 may be, for example, a braided suture, such as a size #5-#9 braided suture. The tension member 250 may be, for example, a single cross-section strand of suture or multiple loops.

As shown in FIGS. 56-60, the coupling 260 may include a first engagement end or first mating jaw 264 at a first end and a second engagement end or second mating jaw 270 at a second end. The coupling 260 may also include a through hole or cannulated opening 262 extending through the coupling 260 along a longitudinal axis of the coupling 260. The first engagement end 264 may include at least one protrusion or tooth 266 and at least one groove or recess 268, as shown in FIG. 56-59. For example, the first engagement end 264 may include three protrusions 266 alternating with three recesses 268. The second engagement end 270 may include at least one protrusion or tooth 272 and at least one groove or recess 274, as shown in FIGS. 56-59. For example, the second engagement end 270 may include three protrusions 272 alternating with three recesses 274. The protrusions 272 may be spaced, for example, 3 mm apart. The coupling 260 may be made of, for example, a bioresorbable material, such as, PLLA, PGA, PLDA, PL-DLA, copolymers of each, resorbable calcium composites, and like materials as known by one of ordinary skill in the art.

As shown in FIGS. 56-61, the anchor member 230 is linked dynamically to the head member 210 by a tension member 250 and a coupling 260. The implant 200 may be assembled by inserting the engagement end 222 of the head member 210 with the first engagement end 264 of the coupling 260 and the engagement end 240 of the anchor member 230 with the second engagement end 270 of the coupling 260. The coupling 260 will be positioned between the head member 210 and the anchor member 230. With the cannulated openings 220, 234, 262 of the head member 210, anchor member 230 and coupling 260, respectively, aligned, the tension member 250 may be inserted into the cannulated openings 220, 234, 262. The tension member 250 may be secured to the head member 210 by securing or tightening the crimp ferrule 228 around the tension member 250 and/or inserting pins (not shown) through at least one opening 218 in the head member 210 to engage and secure the tension member 250. The tension member 250 may also be secured to the anchor member 230 by inserting pins 249 through the at least one opening 246 in the anchor member 230 to engage and secure the tension member 250 and/or by securing or tightening crimp members (not shown) around the tension member 250 at the second end.

A method of inserting the implant 200 may optionally include positioning a plate 184 on a bone 182, for example, a fibula. The method may also include driving a k-wire or guide wire 186 through two bones 180, 182, for example, a fibula 182 and tibia 180, as shown in FIG. 7. Next, as shown in FIG. 8, a drill 188 may be inserted over the k-wire 186 by aligning a cannulated opening 190 in the drill 188 with the k-wire 186. The drill 188 may be used to drill an opening 192 through the bones 180, 182. The opening 192 may have a diameter, for example, that corresponds to the minor diameter of the anchor member 130. After the opening 192 is drilled, the drill 188 and optionally the k-wire 186 may be removed from the bones 180, 182, as shown in FIG. 9. Optionally, after removing the drill 188 and prior to removing the k-wire 186, measurements of the depth of the opening 192 may be taken using a cannulated depth gauge (not shown) inserted over the k-wire 186. Once the measurements are taken, the k-wire 186 may then be removed. Alternatively, the k-wire 186 may be removed from the bones 180, 182 and a standard depth gauge (not shown) may be used to take the measurements. For example, an overall or first depth measurement of the opening or drill hole 192, such as a measurement to the far cortex of the tibia, may be taken using a cannulated depth gauge, standard depth gauge or other like instrument. The surgeon may also take a second depth measurement of the portion of the opening 192 in the fibula using, for example, a standard depth gauge or like instrument, to determine the size of the head member 210. Then, an instrument may be used to insert the implant 200 into the opening 192 in the bones 180, 182. The implant 200 may be inserted to position the anchor member 230 in the tibia 180, the head member 210 in the fibula 182, and the coupling 260 in a tibiofibular clear space or gap. The torsional force applied to the head member 210 for inserting the implant 200 may be transmitted to the anchor member 230 through the coupling 260. Next, the instrument may be removed from head member 210 of the implant 200 and the surgical procedure may be completed.

After inserting the implant 200, the coupling 260 will eventually fail leaving the head member 210 coupled to the anchor member 230 by only the tension member 250. The coupling 260 may fail, for example, after at least a portion of the coupling 260 is resorbed into the patient. Failure of the coupling 260 will allow for semi-constrained motion between the tibia 180 and fibula 182 via the tension member 250. The flexibility of the tension member 250 may allow for diastatic motion of the implant 200. Thus, the implant 200 allows for the patient's physiologic motion to be restored in an anterior-posterior direction, a superior-inferior direction, as well as allowing for fibular rotation, at the joint based on the strength of the tension member 250 and the resorbable coupling 260.

Figure 14:
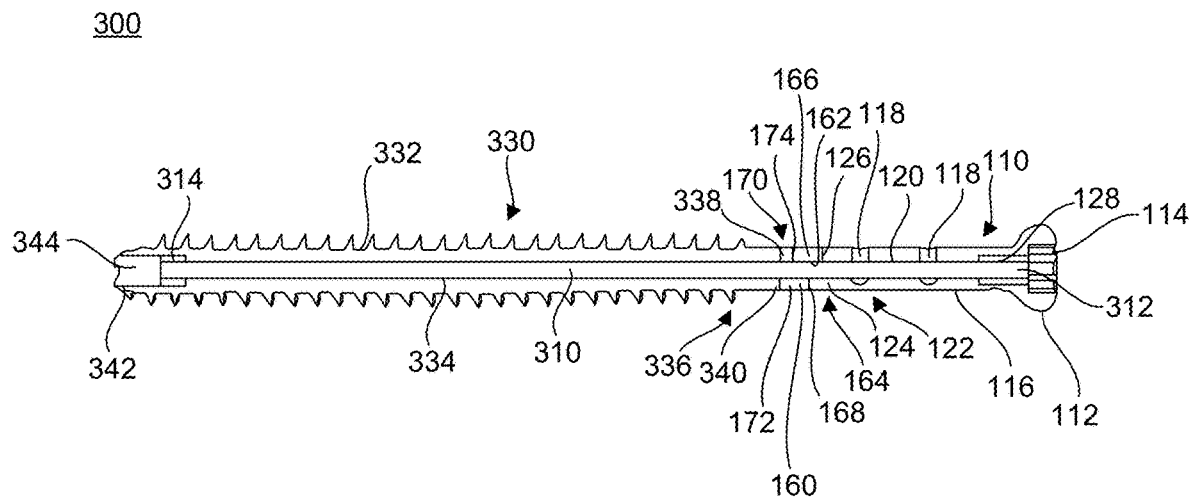
FIG. 14 is a first cross-sectional view of the implant of FIG. 12 taken along line 14-14 in FIG. 13, in accordance with an aspect of the present disclosure.
Figure 15:
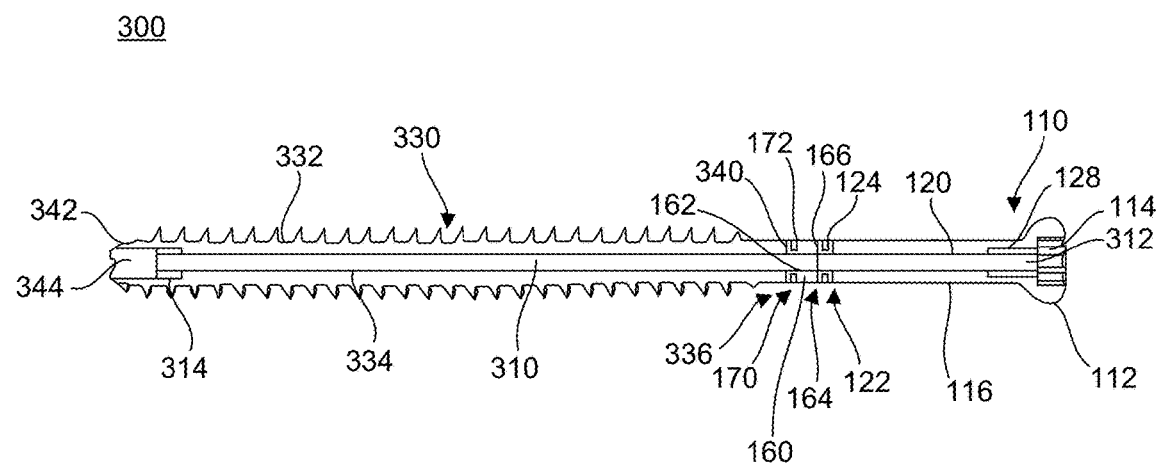
FIG. 15 is a second cross-sectional view of the implant of FIG. 12 taken along a longitudinal line perpendicular to line 14-14 in FIG. 13, in accordance with an aspect of the present disclosure.
Figure 16:
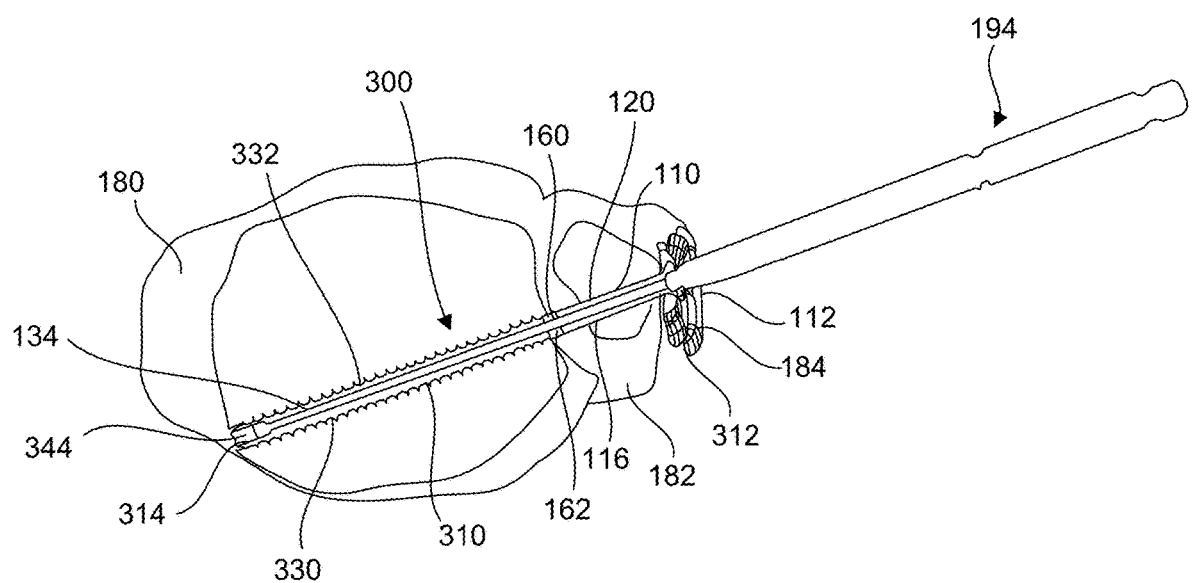
FIG. 16 is a distal, transverse planar view of the bones of FIG. 7 with the implant of FIG. 12 inserted into the drilled opening with a driver instrument, in accordance with an aspect of the present disclosure.

Referring now to FIGS. 12-16, another implant 300 is shown. The implant 300 includes the head member 110 and the anchor member 330. The implant 300 also includes the coupling 160 positioned between the head member 110 and the anchor member 330 for insertion of the implant 300. The head member 110 and drive coupling 160 are described above in greater detail with respect to implant 100 and will not be described again here for brevity sake. Finally, the implant 300 includes a tension member 310 positioned in a cannulated opening extending through the implant 300, as shown in FIGS. 14-16.

The tension member 310, as shown in FIGS. 14-16, includes a first end 312 and a second end, crimp ferrule, or stop member 314. The stop member 314 may be, for example, integral, monolithic or removable from the tension member 310. The diameter of the first end 312 may be, for example, smaller than the diameter of the second end 314. The tension member 310 may be, for example, a stranded cerclage cable or similar construct. The tension member 310 may also be made of, for example, titanium, stainless steel, polymers, polyester or UHMWPE suture, resorbable suture, co-braids thereof, or a like material, as known by one of ordinary skill in the art. The first end 312 of the tension member 310 may be, for example, positioned within the cannulated opening 120 of the head member 110. The first end 312 may be secured to the head member 110 by a crimping feature 128 and/or by pins (not shown). If pins (not shown) are used, the head member 110 may include slots, windows, recesses, apertures (not shown) inset into the interior diameter of the opening 120 and positioned opposite the openings 118. The slots (not shown) may be sized and shaped to receive a pin or engagement member (not shown). The pin (not shown) may be inserted through the openings 118 to engage the tension member 310 and push a portion of the tension member 310 into the opposing slots (not shown) securing the tension member 310 to the head member 110. The slots (not shown) may be, for example, slightly offset from the openings 118 to provide additional securement of the tension member 310 to the head member 110. The pins (not shown) may also be coupled to the head member 110 by, for example, laser welding to prevent a pin from disengaging the head member 110 after insertion into a patient.

Referring now to FIGS. 12-16, the anchor member or tibia member 330 is shown. The anchor member 330 may include a threaded shaft 332 with a cannulated opening or through hole 334 extending through the entire anchor member 330 along a longitudinal axis. The threaded shaft 332 may be, for example, threaded along the entire length of the shaft or only along a portion of the shaft. The anchor member 330 may also include an engagement end or mating jaw 336 at a first end and a cutting end or teeth 342 at a second end. The engagement end 336 may include at least one protrusion or tooth 338 and at least one groove or recess 340, as shown in FIGS. 12-15. For example, the engagement end 336 may include three protrusions 338 alternating with three recesses 340. The second end of the anchor member 330 may also include a bore 344 extending into the anchor member 330 from the second end and engaging the cannulated opening 334. The bore 344 may be, for example, larger than the cannulated opening 334. The bore 344 and cannulated opening 334 may have, for example, a round or circular cross-section and the diameter of the bore 344 may be larger than the diameter of the cannulated opening 334. The size and shape of the bore 344 may correspond to the size and shape of the second end 314 of the tension member 310 to allow the second end 314 to translate within the bore 344 of the anchor member 330. Although not shown, it is also contemplated that the second end or cutting end 342 of the anchor member 330 may include at least one cutting element, for example, at least one cutting flute, such as the cutting flutes on the insertion end 536, as shown in FIGS. 24-32. The at least one cutting element may be, for example, four cutting flutes. It is also contemplated that the cutting flutes at the insertion end may be used as a removal feature if a medial approach is used to remove at least the anchor member 330.

With continued reference to FIGS. 14-16, the first end 312 of the tension member 310 may be inserted through the second end 314 of the anchor member 130 and through the cannulated opening 334. Next, the first end 312 of the tension member 310 may be inserted through the through hole 162 in the coupling 160 and into the head member 110 through the second end until the first end 312 reaches a position before the tool engagement opening 114. The tension member 310 may then be secured to the head member 110 using the crimping feature 128 or, alternatively, by inserting at least one pin (not shown) through the openings 118 in the head member 110. Once assembled, the tension member 310 is rigidly coupled to the head member 110 and once at least a portion of the bioresorbable coupling 160 resorbs into the patient, the anchor member 330 may translate along the tension member 310. The anchor member 330 may translate between contacting the engagement end 122 of the head member 110 at a first end and contacting the second end or stop member 314 of the tension member 310 at the second end. In a fully extended position, the stop member 314 may be fully inserted into the bore 344 of the anchor member 330, as shown in FIGS. 14-16. In an insertion position, the engagement end 436 of the anchor member 430 engages a first end of the coupling 160 and the engagement end 122 of the head member 110 engages a second end of the coupling 160 to allow for the torsional force of the insertion instrument to be translated to the anchor member 330.

Referring now to FIGS. 7-9 and 16, a method of inserting the implant 300 is shown. The method may include forming the opening 192, as shown in FIGS. 7-9 and described in greater detail above with reference to implant 100, which will not be described again here for brevity sake. Next, as shown in FIG. 16, an instrument 194, for example, a driver instrument may be used to insert the implant 300 into the opening 192 in the bones 180, 182. The torsional force applied to the head member 110 for inserting the implant 300 may be transmitted to the anchor member 330 through the coupling 160. Next, the instrument 194 may be removed from head member 110 of the implant 300 and the surgical procedure may be completed. After inserting the implant 300, the coupling 160 will eventually fail leaving the head member 110 coupled to the anchor member 330 by only the tension member 310. The coupling 160 may fail, for example, after at least a portion of the coupling 160 is resorbed into the patient. Failure of the coupling 160 allows for semi-constrained motion between the tibia 180 and fibula 182 via the tension member 310. The flexibility of the tension member 310 may allow for diastatic motion of the implant 300. Thus, the implant 300 allows for the patient's physiologic motion to be restored in an anterior-posterior direction, superior-inferior direction, as well as allowing for fibular rotation, at the joint based on the strength of the tension member 310 and the resorbable coupling 160.

Referring now to FIGS. 17-23, another implant 400 is shown. The implant 400 includes a head member 110, an anchor member 430, and a tension member 410 that couples the head member 110 and the anchor member 430, as shown in FIGS. 19-23. The head member 110 is described above in greater detail with respect to implant 100 and will not be described again here for brevity sake. The tension member 410 may extend through a center of at least a portion of the aligned head member 110 and at least a portion of the anchor member 430. The implant 400 may have a length of, for example, approximately 40 mm to 70 mm. In one embodiment, the length of the head member 110 may remain constant, while the length of the anchor member 430 may be variable to correspond to the varying size of a patient's bones 180, 182. Alternatively, in another embodiment, the head member 110 may, for example, be available in multiple lengths to correspond to the varying sizes of the patient's bones 180, 182 and the length of the anchor member 430 may remain constant. In yet another embodiment, both the head member 110 and the anchor member 430 may be available in multiple lengths to allow for selection based on the size of the patient's bones 180, 182. The tension member 410 may provide a gap of, for example, 3 mm when the head member 110 and anchor member 430 are fully extended.

As shown in FIGS. 19-23, the tension member 410 may include a first end 412 and a second end, crimp ferrule, or stop member 414. The diameter of the first end 412 may be, for example smaller than the diameter of the second end 414. The tension member 410 may be a stranded cerclage cable or similar construct. The tension member 410 may also be made of, for example, titanium, stainless steel, polymers, polyester or UHMWPE suture, resorbable suture, co-braids thereof, or a like material as known by one of ordinary skill in the art.

Figure 17:
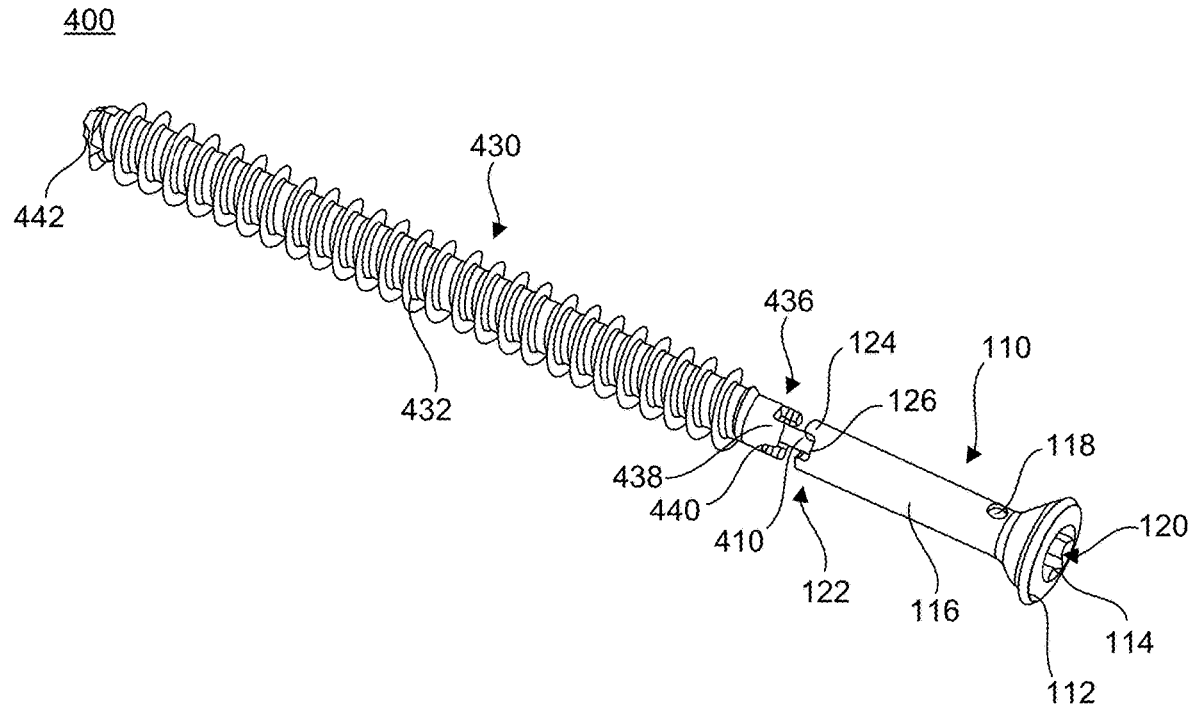
FIG. 17 is a perspective side view of another implant, in accordance with an aspect of the present disclosure.
Figure 18:
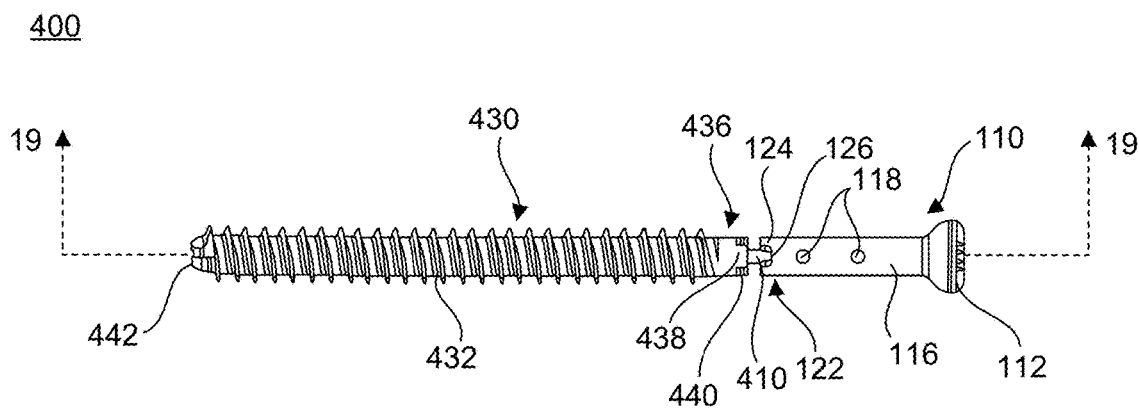
FIG. 18 is a side view of the implant of FIG. 17, in accordance with an aspect of the present disclosure.
Figure 19:
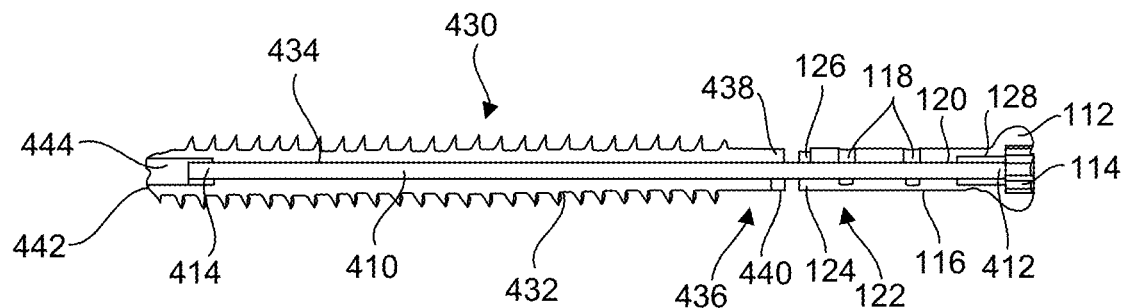
FIG. 19 is a first cross-sectional view of the implant of FIG. 17 taken along line 19-19 in FIG. 18, in accordance with an aspect of the present disclosure.
Figure 20:
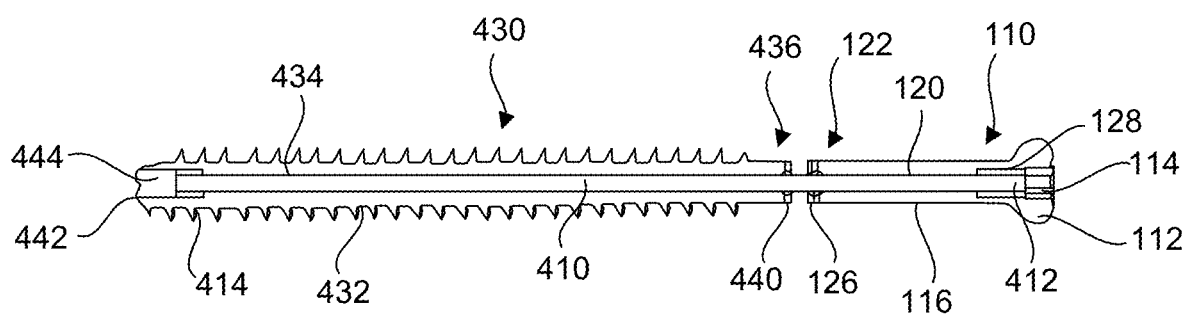
FIG. 20 is a second cross-sectional view of the implant of FIG. 17 taken along a longitudinal line perpendicular to line 19-19 in FIG. 18, in accordance with an aspect of the present disclosure.

Referring now to FIGS. 17-23, the anchor member or tibia member 430 is shown. The anchor member 430 may include a threaded shaft 432 with a cannulated opening or through hole 434 extending through the entire anchor member 430 along a longitudinal axis. The threaded shaft 432 may be, for example, threaded along the entire length of the shaft or only along a portion of the shaft. The anchor member 430 may also include an engagement end or mating jaw 436 at a first end and a cutting end or teeth 442 at a second end. The engagement end 436 may include at least one protrusion or tooth 438 and at least one groove or recess 440, as shown in FIGS. 17-20. For example, as shown in FIG. 17, the engagement end 436 includes three protrusions 438 alternating with three recesses 440. The second end of the anchor member 430 may also include a bore 444 extending into the anchor member 430 from the second end and engaging the cannulated opening 434. The bore 444 may be, for example, larger than the cannulated opening 434. The bore 444 and cannulated opening 434 may have, for example, a round or circular cross-section and the diameter of the bore 444 may be larger than the diameter of the cannulated opening 434. The size and shape of the bore 444 may correspond to the size and shape of the second end 414 of the tension member 410 to allow the second end 414 to translate within the bore 444 of the anchor member 430. Although not shown, it is also contemplated that the second end or cutting end 442 of the anchor member 430 may include at least one cutting element, for example, at least one cutting flute, such as the cutting flutes on the insertion end 536, as shown in FIGS. 24-32. The at least one cutting element may be, for example, four cutting flutes. It is also contemplated that the cutting flutes at the insertion end may be used as a removal feature if a medial approach is used to remove at least the anchor member 430.

The implant 400 may be assembled, for example, by inserting the first end 412 of the tension member 410 through the second end of the anchor member 430 and through the cannulated opening 434. Next, the first end 412 of the tension member 410 may be inserted into the head member 110 through the second end until the first end 412 reaches a position before the tool engagement opening 114. The tension member 410 may then be secured to the head member 110 by inserting at least one pin (not shown) through the openings 118 in the head member 110. Once assembled, the tension member 410 is rigidly coupled to the head member 110 and the anchor member 430 may translate along the tension member 410. The anchor member 430 may translate between contacting the engagement end 122 of the head member 110 at a first end and contacting the second end or stop member 414 of the tension member 410 at the second end. In a fully extended position, the stop member 414 may be fully inserted into the bore 444 of the anchor member 430, as shown in FIGS. 19, 20, 22 and 23. In an insertion position, as shown in FIG. 21, the engagement end 436 of the anchor member 430 engages the engagement end 122 of the head member 110 to allow for the torsional force of the insertion instrument to be translated to the anchor member 430.

Figure 21:
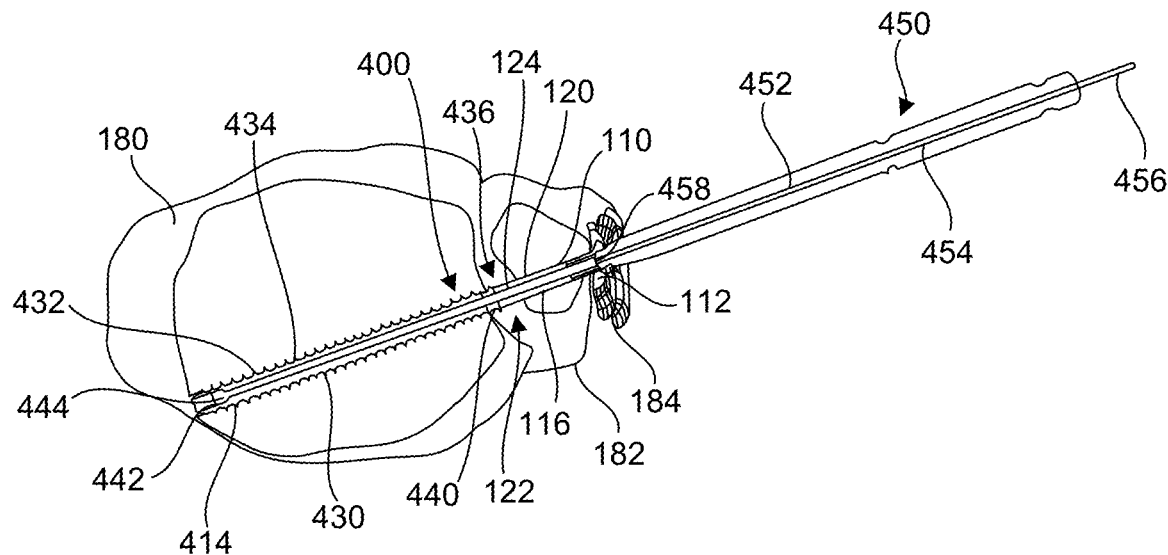
FIG. 21 is a distal, transverse planar view of the bones of FIG. 7 with the implant of FIG. 17 inserted into the drilled opening with a driver instrument, in accordance with an aspect of the present disclosure.
Figure 22:
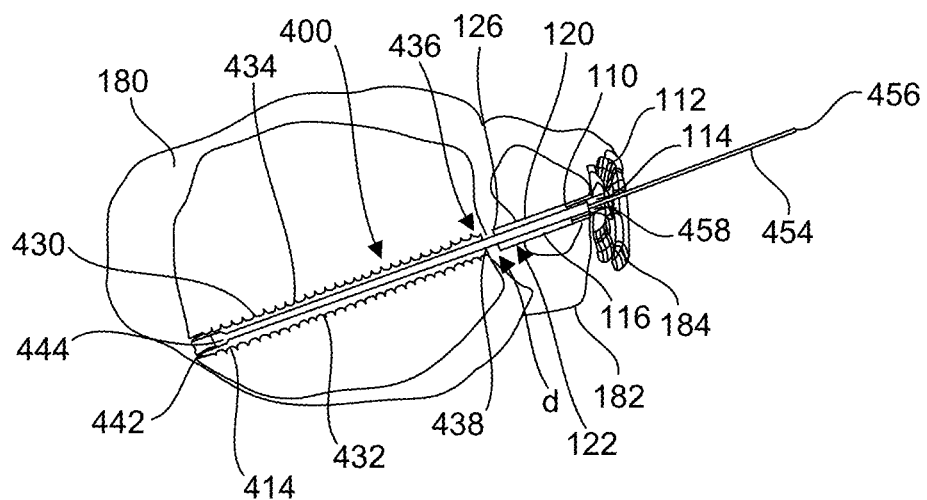
FIG. 22 is a distal, transverse planar view of the bones of FIG. 7 after the driver instrument is removed from the implant of FIG. 17 and the remaining disengagement suture is pulled to release the direct drive coupling, in accordance with an aspect of the present disclosure.
Figure 23:
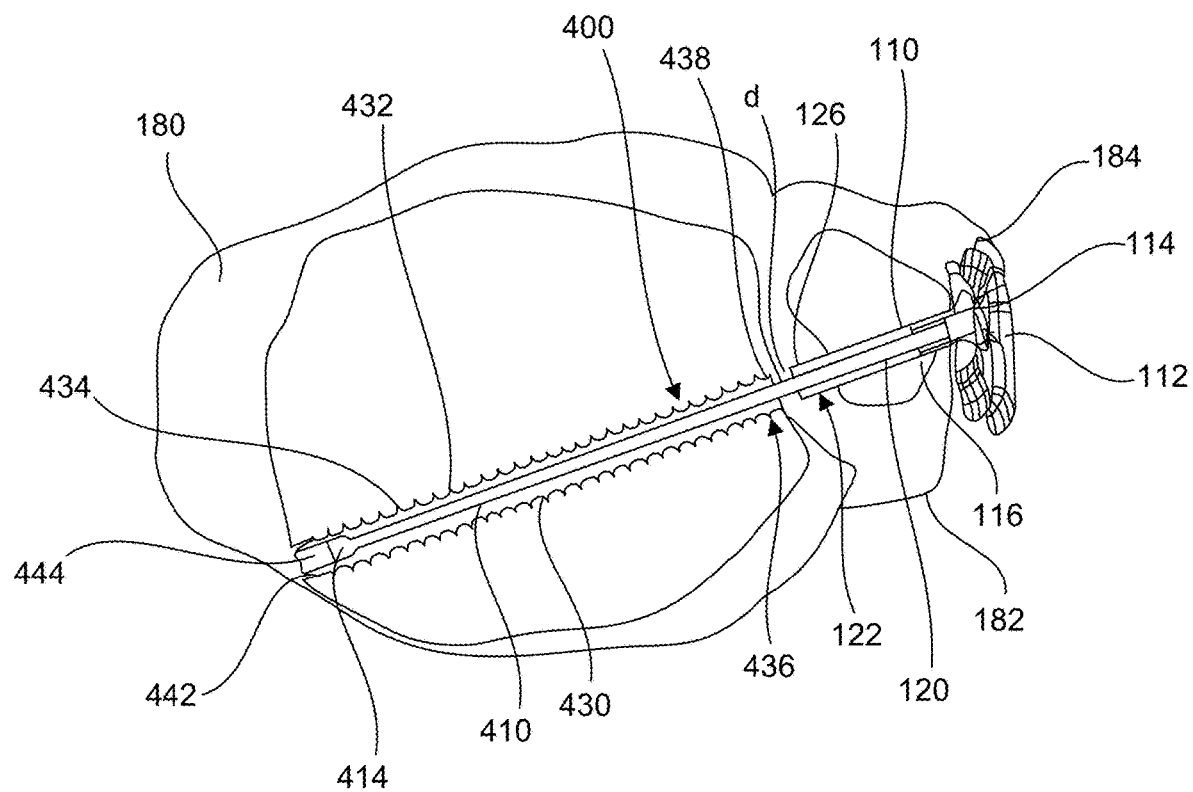
FIG. 23 is a distal, transverse planar view of the bones of FIG. 7 after cutting the disengagement suture of FIG. 22, in accordance with an aspect of the present disclosure.
Figure 24:
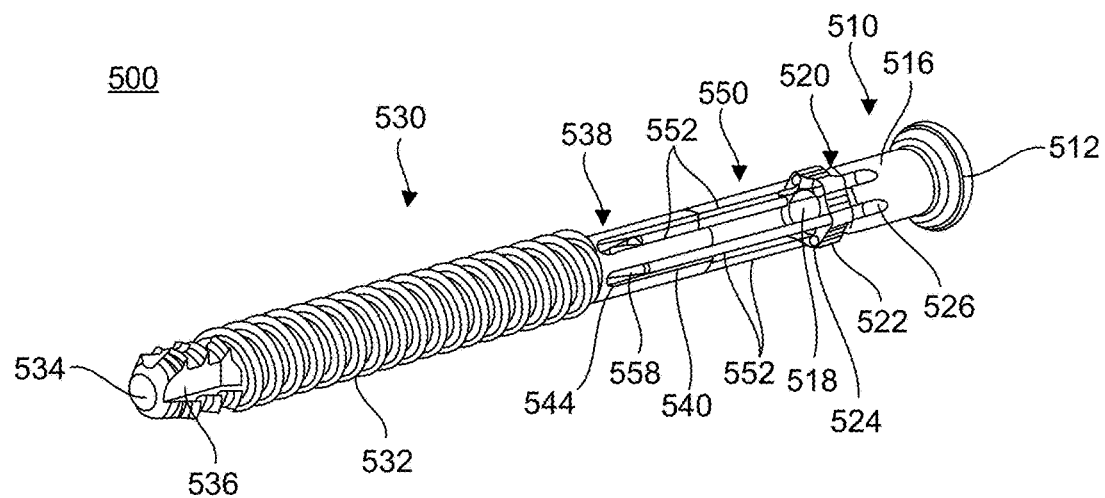
FIG. 24 is a first end, perspective view of another implant, in accordance with an aspect of the present disclosure.

Referring now to FIGS. 7-9 and 21-23, a method of using the implant 400 is shown. The method may include forming the opening 192, as shown in FIGS. 7-9 and described in greater detail above with reference to implant 100, which will not be described again here for brevity sake. Next, as shown in FIG. 21, an instrument or screw driver 450 may be used to insert the implant 400 into the opening 192 in the bones 180, 182. Thus instrument or screw driver 450 may include a through hole or cannulated opening 452 to receive a disengagement suture 454 during insertion of the implant 100. The torsional force applied to the head member 110 for inserting the implant 400 may be transmitted to the anchor member 430 through the engagement of the mating jaw 122 of the head member 110 with the mating jaw 436 of the anchor member 430. Next, the instrument 450 may be removed from the head member 110 of the implant 400 by sliding the instrument 450 off of the disengagement suture 454, as shown in FIG. 22. After the instrument 450 is removed, the first end 456 of the disengagement suture 454 may be pulled. As the first end 456 is pulled, the second end 458 of the disengagement suture 454, which is coupled to the implant 400, is also pulled and disengages the mating jaw 122 of the head member 110 from the mating jaw 436 of the anchor member 430. Once the disengagement suture is pulled, the anchor member 430 may translate to seat the stop member 414 into the bore 444 to fully extend or expand the implant 400 and provide the tibiofibular clear space or gap d between the tibia 180 and fibula 182, as shown in FIG. 22. When the implant 400 is in an expanded position, the flexibility of the tension member 410 may allow for restoration of physiologic motion of the joint as the tension member 410 flexes. Next, the disengagement suture 454 may be cut, as shown in FIG. 23, and the surgical procedure may be completed.

Referring now to FIGS. 24-36, another implant 500 is shown. The implant 500 includes a head member 510, an anchor member 530, a tension member 550, and an elastic member 560 (see FIGS. 27-33). The tension member 550 couples the head member 510 to the anchor member 530. The tension member 550 may create, for example, a dynamic link between the head member 510 and anchor member 530. The elastic member 560 allows for motion between the head member 510 and the anchor member 530. In addition, the elastic member 560 provides support for the tension member 550. The implant 500 may have a length of, for example, approximately 40 mm to 70 mm. The tension member 550 may form a gap between the head member 510 and the anchor member 530 with the length of the gap being, for example, approximately 8 mm. The head member 510 and gap created by the tension member 550 may, for example, remain constant and the length of the anchor member 530 may, for example, vary based on the anatomy of the patient. Alternatively, the length of the head member 510 may also vary based on the anatomy of the patient, while the length of the anchor member 530 and gap remain constant. In a further embodiment, the length of the head member 510 and the anchor member 530 may vary based on the patient's anatomy and the gap may remain constant.

Figure 25:
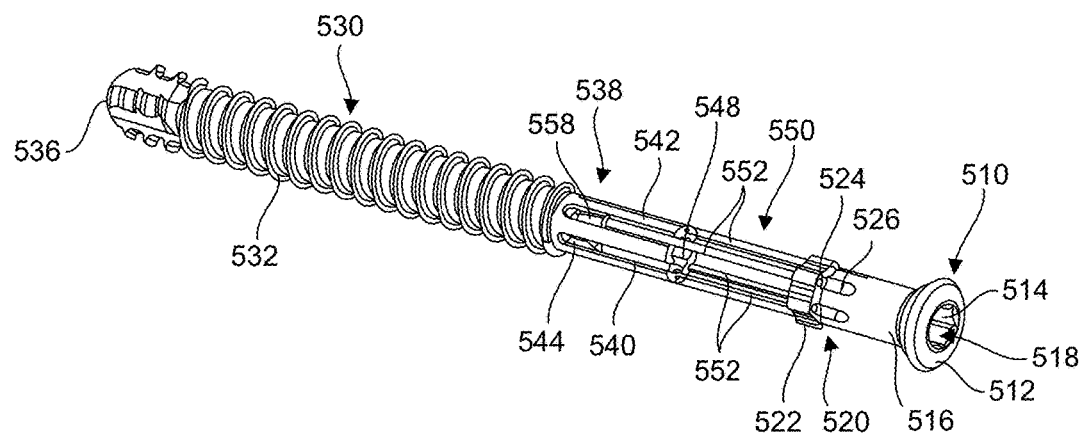
FIG. 25 is a second end, perspective view of the implant of FIG. 24, in accordance with an aspect of the present disclosure.
Figure 26:
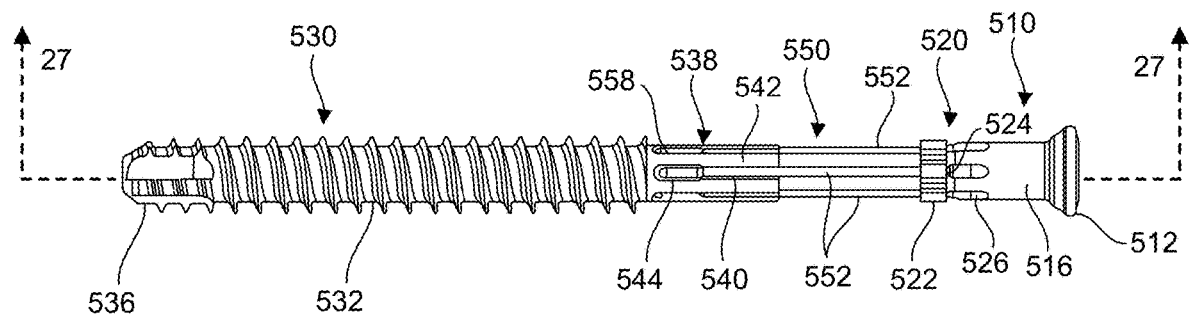
FIG. 26 is a side view of the implant of FIG. 24, in accordance with an aspect of the present disclosure.
Figure 30:
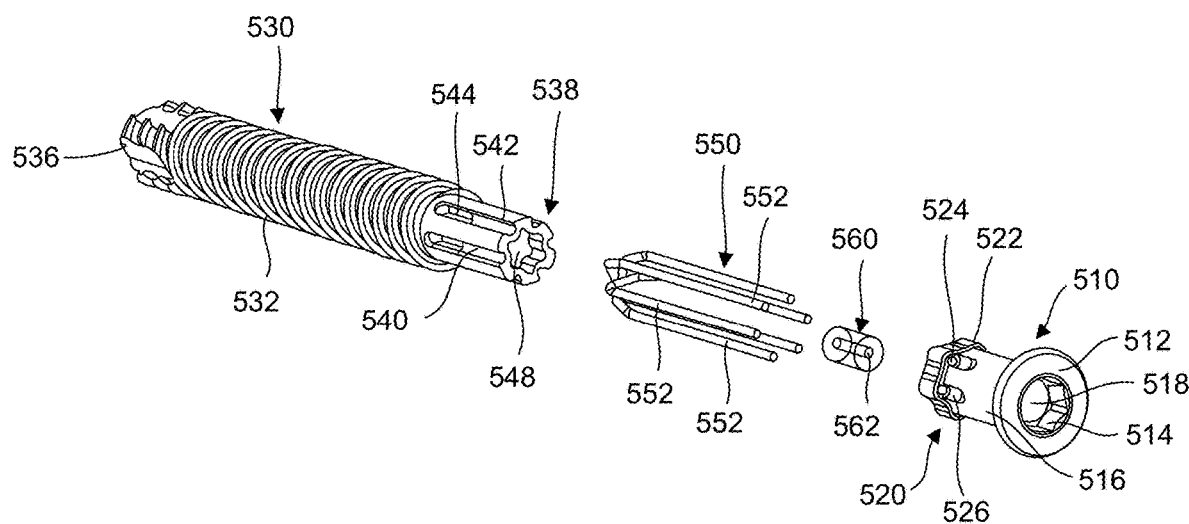
FIG. 30 is a partially exploded, second end perspective view of the implant of FIG. 25, in accordance with an aspect of the present disclosure.
Figure 31:
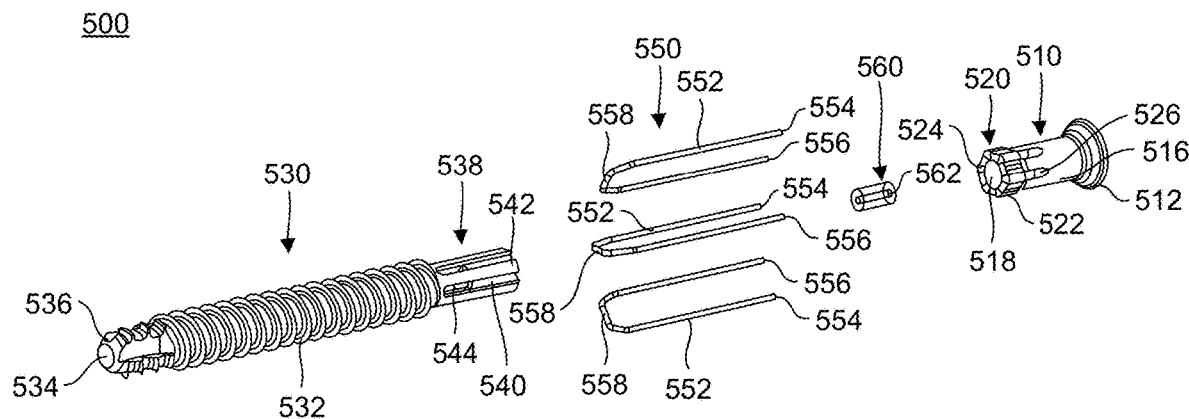
FIG. 31 is an exploded, first end perspective view of the implant of FIG. 25, in accordance with an aspect of the present disclosure.
Figure 32:
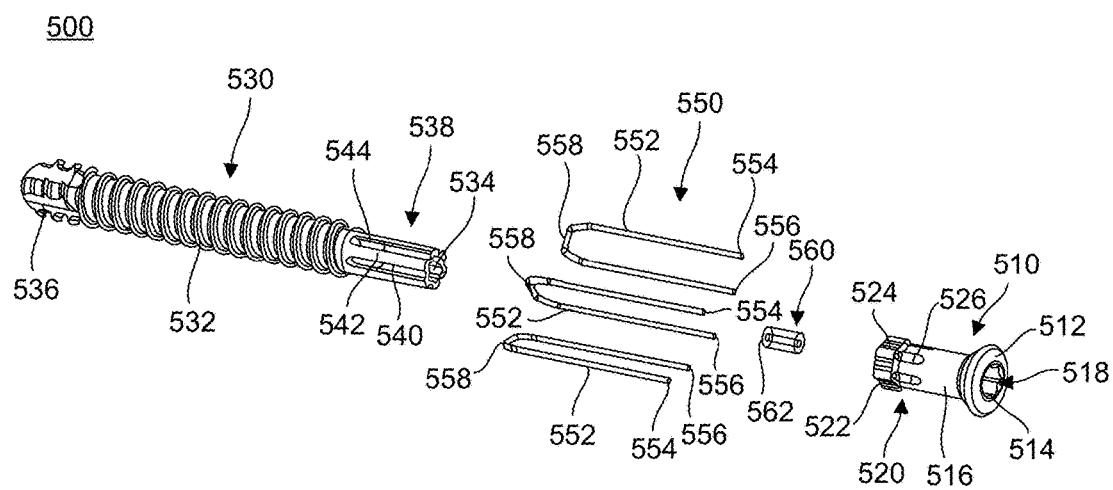
FIG. 32 is an exploded, second end perspective view of the implant of FIG. 25, in accordance with an aspect of the present disclosure.

As shown in at least FIGS. 24-32, the head member or fibula member 510 includes a head 512 and a shaft member 516 extending away from a second end of the head 512. The head 512 may also include a tool engagement opening 514 positioned on a first end opposite the shaft member 516, as shown in FIGS. 25, 30, 32. In addition, the head member 510 may include a through hole or cannulated opening 518 extending from the tool engagement opening 514 at the first end to the second end of the head member 510 along the longitudinal axis. The second end may also include an engagement end 520 for coupling to the tension member 550, as shown in FIGS. 24-28. The engagement end 520 may include a capture member or swag feature 522 positioned at the second end of the head member 510. The capture member 522 may include a plurality of suture holes or capture holes 524 positioned around the exterior surface of the head member 510, as shown in FIGS. 24-26 and 29-32. The plurality of suture holes 524 may align with recesses 526 in the shaft member 516 adjacent to the capture member 522. The plurality of suture holes 524 and recesses 526 may be positioned to receive a portion of a suture 552 of the tension member 550, as shown in FIGS. 24-26 and 28. Although any number of suture holes 524 and recesses 526 are contemplated, in one embodiment, the head member 510 may include, for example, six suture holes 524 aligned with six recesses 526. The head member 510 may be made of, for example, titanium, stainless steel or a like material as known by one of ordinary skill in the art. Although not shown, at least a portion of the shaft member 516 of the head member 510 may be, for example, threaded.

Figure 27:
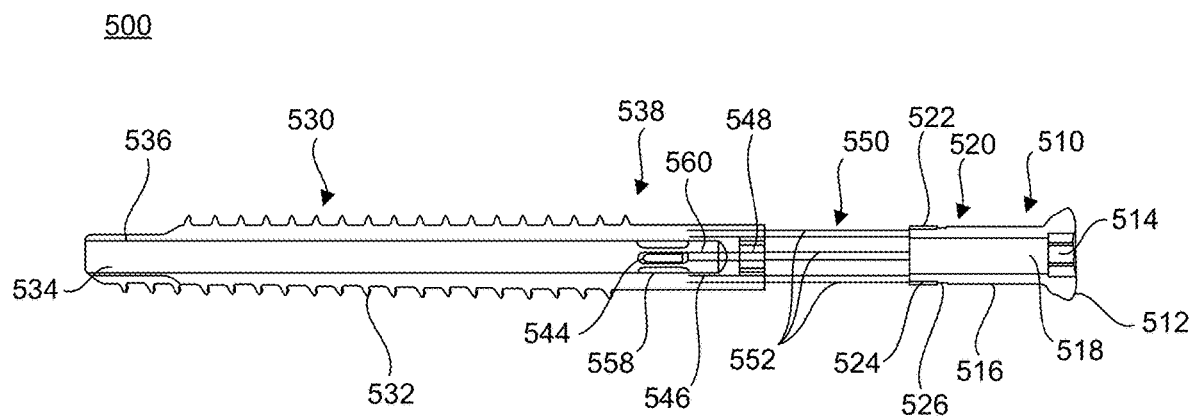
FIG. 27 is a first cross-sectional view of the implant of FIG. 25 taken along line 27-27 in FIG. 26, in accordance with an aspect of the present disclosure.
Figure 28:
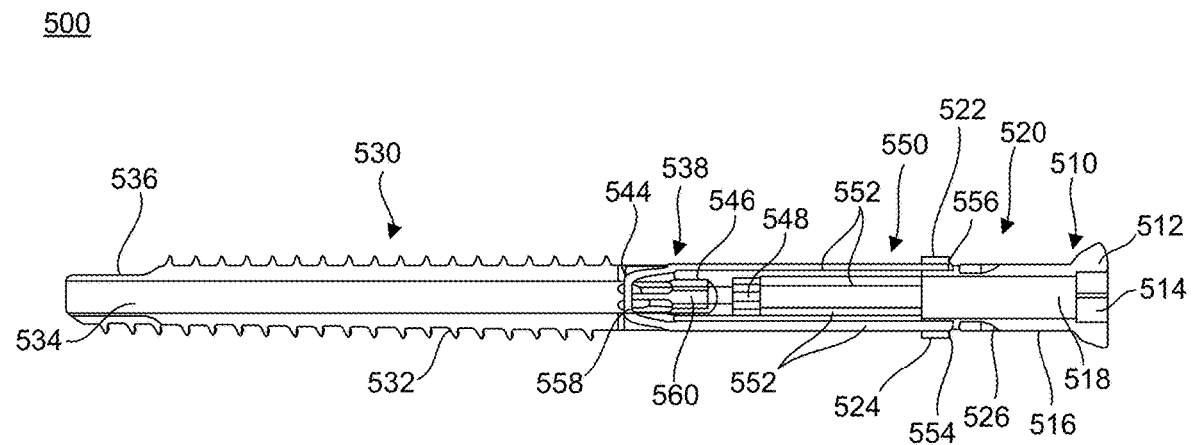
FIG. 28 is a second cross-sectional view of the implant of FIG. 25 taken along a longitudinal line perpendicular to line 27-27 in FIG. 26, in accordance with an aspect of the present disclosure.
Figure 29:
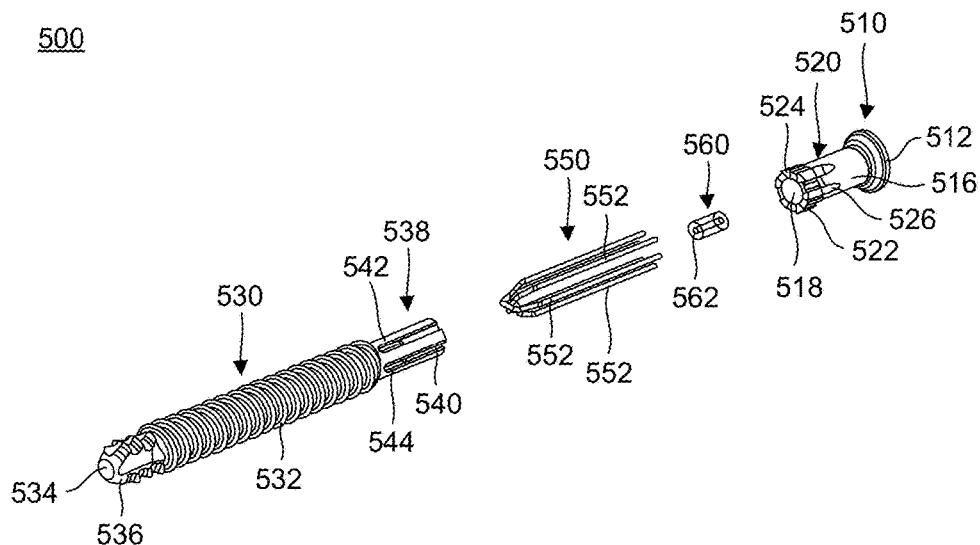
FIG. 29 is a partially exploded, first end perspective view of the implant of FIG. 25, in accordance with an aspect of the present disclosure.

With continued reference to FIGS. 24-32, the anchor member or tibia member 530 is shown. The anchor member 530 may include a threaded shaft 532 with an insertion end 536 at one end and an engagement end 538 at the other end. The anchor member 530 may also include a hole or opening 534 extending from the distal end toward the proximal end or engagement end 538, as shown in FIGS. 24 and 27-29. The engagement end 538 may include grooves or recesses 540 positioned around the exterior surface of the anchor member 530. The grooves 540 may be aligned with the suture holes 524 of the head member 510. Protrusions 542 may be formed between the grooves 540 of the anchor member 530. The grooves 540 may also include at least one opening, slot or through hole 544 extending from the grooves 540 into the opening 534. As shown in FIGS. 27 and 28, the anchor member 530 may also include a bumper opening 546 positioned in the proximal end of the opening 534. The bumper opening 546 may be sized and shaped or configured to receive the elastic member 560, as shown in FIGS. 27 and 28. Further, the anchor member 530 may include an anchor element or anchor instrument opening 548 positioned at the proximal end of the anchor member 530, as shown in FIGS. 25, 27, 28, 30 and 32. The insertion end 536 may also include at least one cutting element, for example, at least one cutting flute, as shown in FIGS. 24-32. The at least one cutting element at the insertion end 536 may be, for example, four cutting flutes. It is also contemplated that the cutting flutes at the insertion end 536 may be used as a removal feature if a medial approach is used to remove at least the anchor member 530. The anchor member 530 may be made of, for example, titanium, stainless steel, polymer, or a like material as known by one of ordinary skill in the art.

The tension member 550, as shown in FIGS. 24-32, may include at least one suture 552. The sutures 552 may be, for example, braided sutures or monofilament to provide additional flexibility in diastasis. The suture 552 may have a first end 554, a second end 556 and a middle portion 558 positioned between the first end 554 and the second end 556, as shown in FIGS. 31 and 32. The first end 554 and second end 556 of the tension member 550 may be received within the holes 524 of the head member 510, as shown in FIG. 28. For example, the first end 554 of a suture 552 may be received within a hole 524 that is positioned directly opposite the hole 524 which receives the second end 556 of the same suture 552. In addition, the middle portion 558 may be positioned within the grooves 540 of the anchor member 530 and extend through the openings 544 in the anchor member 530, as best shown in FIG. 28. The middle portion 558 may, for example, extend between two openings 544 that are positioned opposite each other. The tension member 550 may include, for example, three sutures 552 forming six suture lengths, as shown in FIGS. 29-32. The implant 500 may include, for example, one to four sutures 552 forming two to eight suture lengths, alternatively, the implant 500 may include two to eight single sutures lengths. The sutures 552 may be, for example, braided suture, size #0. The sutures 552 may be made of, for example, polyester, UHMWPE, absorbable material, and the like as known by one of ordinary skill in the art.

The elastic member, compliant bumper or bumper 560, as shown in FIGS. 27-32, may include a first end and a second end. The elastic member 560 may also include a through hole 562 extending from the first end to the second end along a longitudinal axis of the elastic member 560. The elastic member 560 may be made of, for example, an extruded thermoplastic urethane (TPU) with a durometer of, for example, 75-95 Shore A. The elastic member 560 may have an outer diameter of, for example, approximately 1.5 mm. The inner diameter of the elastic member 560 may vary based on the desired ligament stiffness. The elastic member 560 may have a length of, for example, approximately 3 mm. To obtain the desired elastic deformation the length, inner diameter and outer diameter of the elastic member 560 may be adjusted.

The implant 500 may be assembled by inserting an elastic member 560 into the bumper opening 546 in the anchor member 530. Next, the middle portion 558 of the at least one suture 552 may be inserted through the at least one opening 544 in the anchor member 530 distal to the elastic member 560, as shown in FIGS. 27 and 28. Then, the first and second ends 554, 556 of the sutures 552 may be inserted into the suture holes 524 in the head member 510 and secured to provide the desired gap between the anchor member 530 and the head member 510. To secure the sutures 552 to the head member 510, the exterior structure forming the suture holes 524 may be deformed to capture or lock the suture ends 554, 556 to the head member 510. After the sutures 552 are secured in the holes 524 of the head member 510 any excess suture material may be removed or cut to a size that fits within the suture recesses 526. Then, the implant 500 is ready for insertion into a patient. The assembled implant 500 allows for diastatic motion by the sutures 552 compressing the elastic member 560 when the head member 510 in the fibula 182 is pulled away from the tibia 180. The elastic deformation of the elastic member 560 allows for the compression and resulting motion off the implant 500. The elastic member 560 may have a stiffness that is, for example, equal to that of a physiologically intact syndesmosis, such as 50-200 N/mm.

Figure 33:
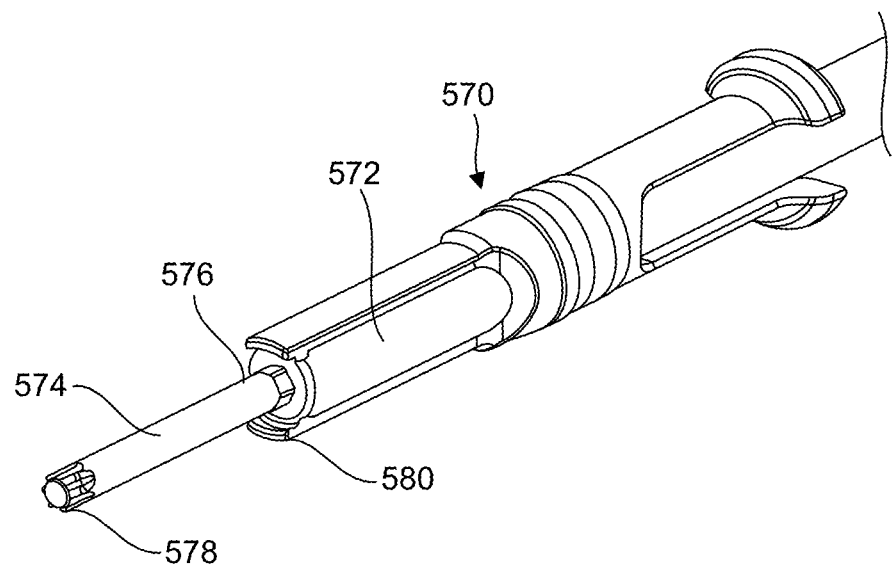
FIG. 33 is a perspective view of a portion of an insertion instrument for inserting the implant of FIG. 25, in accordance with an aspect of the present disclosure.
Figure 34:
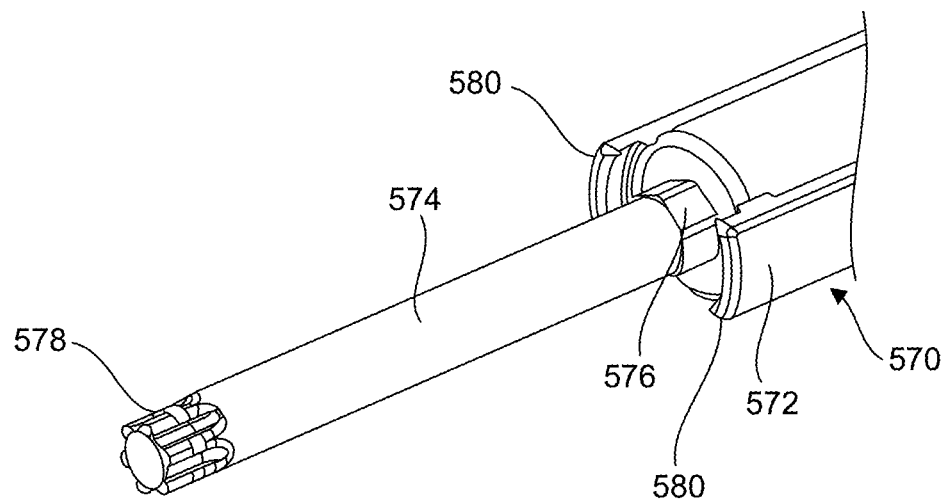
FIG. 34 is an enlarged, perspective view of an end of the insertion instrument of FIG. 33, in accordance with an aspect of the present disclosure.
Figure 35:
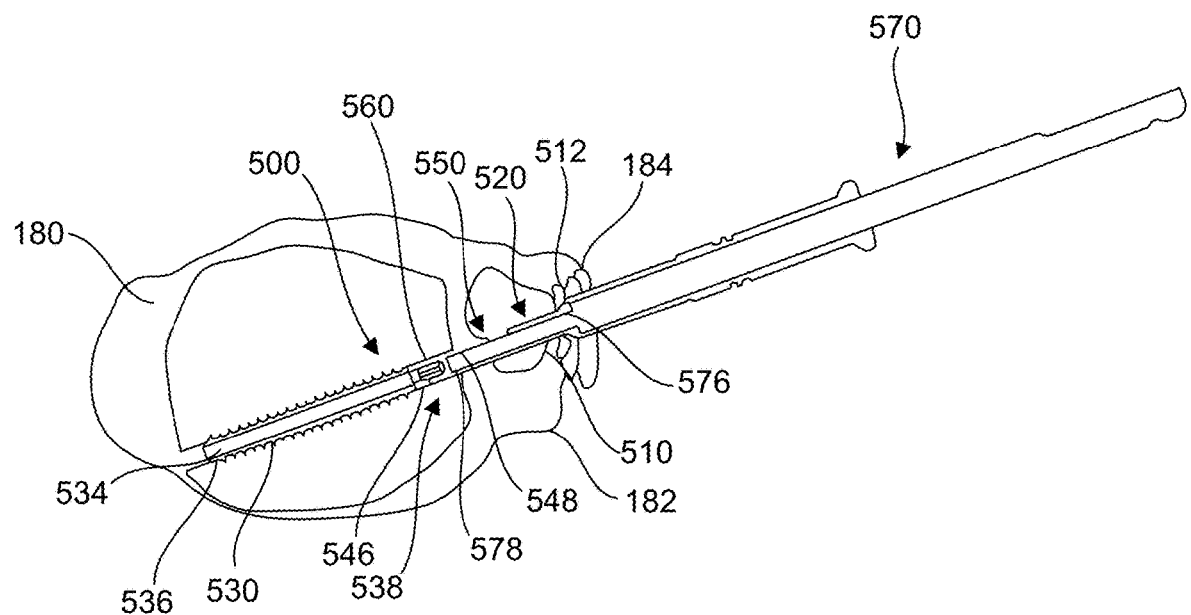
FIG. 35 is a distal, transverse planar view of the bones of FIG. 7 with the implant of FIG. 24 inserted into the drilled opening with a driver instrument, in accordance with an aspect of the present disclosure.

An insertion instrument or inserter 570 is shown in FIGS. 33-34. The insertion instrument 570 includes a first shaft member 572 coupled to a handle or driver instrument (not shown) and a second shaft member 574 extending away from the first shaft member 572. The first shaft member 572 may have a larger diameter than the second shaft member 574. The second shaft member 574 may have a first end and a second end. The first end of the second shaft member 574 is coupled to the first shaft member 572. The first end of the second shaft member 574 may include a proximal feature 576. The proximal feature 576 may be, for example, a custom hex drive feature, as shown in FIGS. 33 and 34. The proximal feature 576 may be sized and shaped or configured to engage the tool engagement opening 514 of the head member 510, as shown in FIG. 35. The second end of the second shaft member 574 may include a distal feature 578. The distal feature 578 may be, for example, a modified T7 drive feature, as shown in FIGS. 33 and 34. The distal feature 578 may be sized and shaped or configured to engage the tibia anchor element 548 of the anchor member 530, as shown in FIG. 35. The inserter 570 may also include a captivation sleeve 580 that couples to or clips on the head 512 of the head member 510. The captivation sleeve 580 maintains the axial spacing of the implant 500 during insertion. In addition, the captivation sleeve 580 self-releases from the implant 500 upon the bottoming out of captivation sleeve 580 when the head member 510 engages the fibula 182. The captivation sleeve 580 also provides support to the head 512 of the head member 510 during insertion or implantation to minimize the stress on the tension member 550 until the implant 500 is fully seated. The inserter 570 also allows for the fully assembled implant 500 to be inserted and for all of the components of the implant 500 to rotate together.

Figure 36:
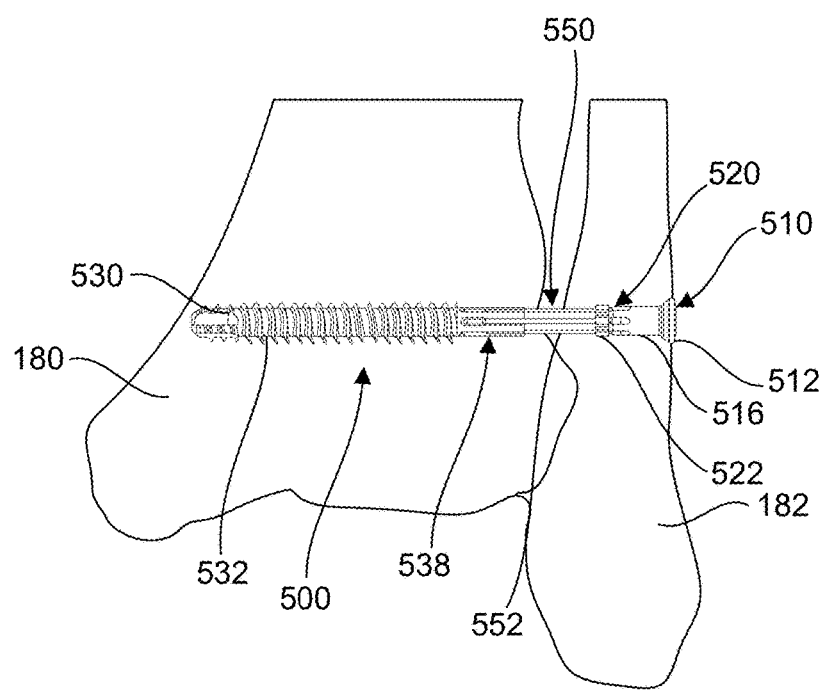
FIG. 36 is a posterior view of the bones of FIG. 35 with the implant of FIG. 24 inserted through the fibula and into the tibia, in accordance with an aspect of the present disclosure.

Referring now to FIGS. 7-9 and 35-36, a method of inserting the implant 500 is shown. The method may include forming the opening 192, as shown in FIGS. 7-9 and described in greater detail above with reference to implant 100, which will not be described again here for brevity sake. Next, as shown in FIG. 35, an insertion instrument 570 may be used to insert the implant 500 into the opening 192 in the bones 180, 182. The instrument 570 engages the anchor member 530 and head member 510 to provide uniform torsional force to the anchor member 530 and the head member 510. Once the implant 500 is fully inserted, i.e., the inserter 570 bottoms out causing detachment of the inserter 570 from the implant 500, as shown in FIG. 36. The inserter 570 can then be removed. Finally, the surgical procedure may be completed.

Another implant 600 is shown in FIGS. 37-45. The implant 600 includes a head member 510, an anchor member 610, and a tension member 640 coupling the head member 510 to the anchor member 610. The head member 510 is described above in greater detail with respect to implant 500 and will not be described again here for brevity sake.

Figure 39:
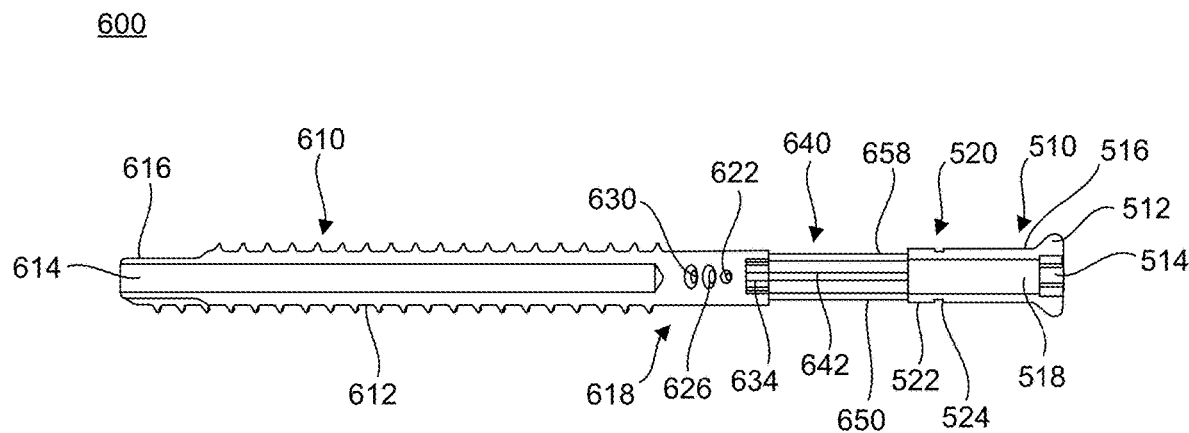
FIG. 39 is a first cross-sectional view of the implant of FIG. 37 taken along line 39-39 in FIG. 38, in accordance with an aspect of the present disclosure.
Figure 40:
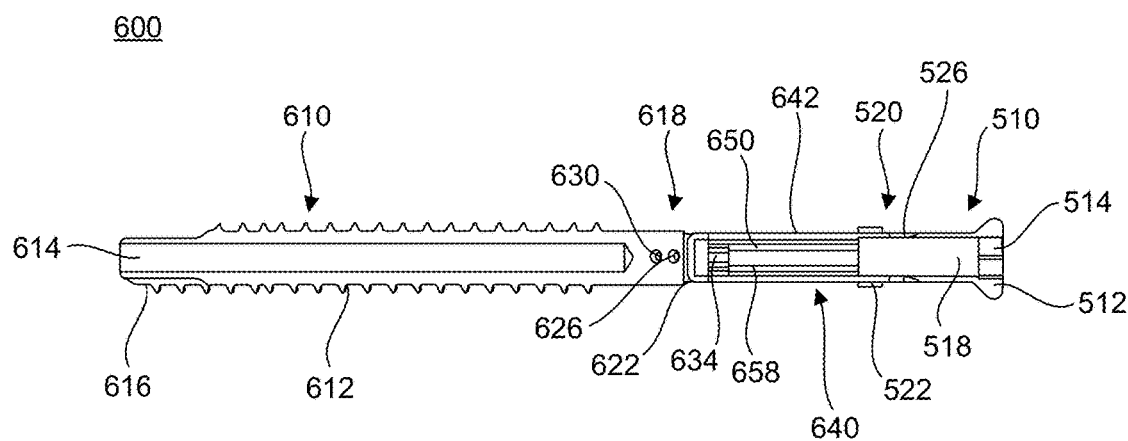
FIG. 40 is a second cross-sectional view of the implant of FIG. 37 taken along a longitudinal line perpendicular to line 39-39 in FIG. 38, in accordance with an aspect of the present disclosure.

As shown in FIGS. 37-43, the anchor member 610 includes a threaded shaft 612 with a first end and a second end. The anchor member 610 may optionally include a hole 614 extending into the threaded shaft 612 from the second end or insertion end 616, as shown in FIGS. 39 and 40. The first end of the anchor member 610 includes an engagement end 618, as shown in FIGS. 37-43. The engagement end 618 includes grooves or recesses 620, 624, 628 separate by protrusions 632. The distal end of each groove 620, 624, 628 may include an opening or through hole 622, 626, 630. The grooves 620, 624, 628 may have different lengths. For example, the first groove 620 may have a first length, the second groove 624 may have a second length and the third groove 628 may have a third length. The first length may be shorter than the second and third lengths and the third length may be longer than the first and second lengths. Each opening 622, 626, 630 may, for example, connect two corresponding grooves 620, 624, 628 positioned opposite of each other around the circumference of the engagement end 618. The grooves 620, 624, 628 and openings 622, 626, 630 may be sized and shaped or configured to receive a suture 642, 650, 658, as shown in FIGS. 37-40 and described in greater detail below. The engagement end 618 of the anchor member 610 may also include an element or tibia anchor element 634 inset into the end of the anchor member 610, as shown in FIGS. 37, 39-41 and 43. The element 634 may be sized and shaped or configured to receive an insertion instrument, such as instrument 570, as described in greater detail above with reference to implant 500, which will not be described again here for brevity sake. The insertion end 616 may include at least one cutting element, for example, at least one cutting flute, as shown in FIGS. 37-43. The at least one cutting element at the insertion end 616 may be, for example, four cutting flutes. It is also contemplated that the cutting flutes at the insertion end 616 may be used as a removal feature if a medial approach is used to remove the anchor member 610. The anchor member 610 may be made of, for example, titanium, stainless steel, polymer, or a like material as known by one of ordinary skill in the art.

Figure 41:
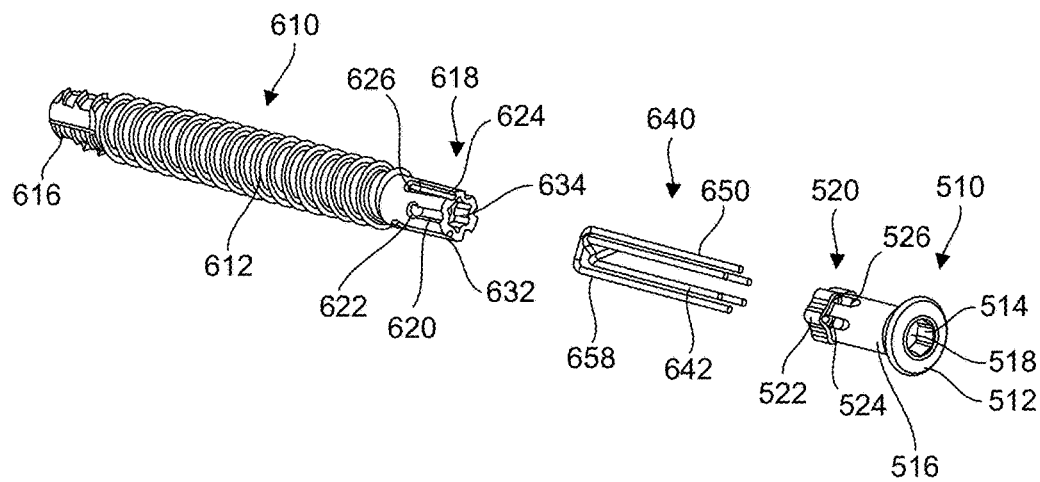
FIG. 41 is a partially exploded, first end perspective view of the implant of FIG. 37, in accordance with an aspect of the present disclosure.
Figure 42:
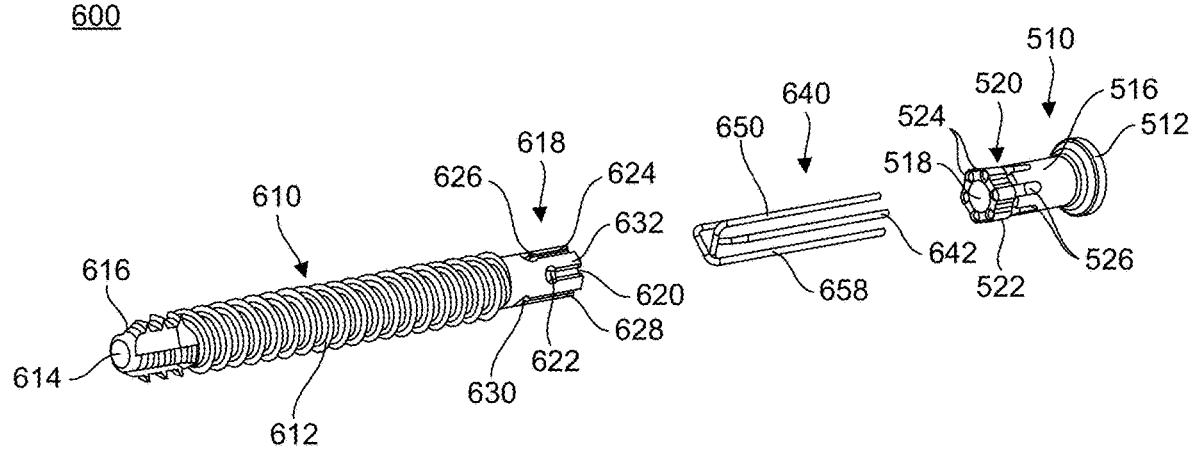
FIG. 42 is a partially exploded, second end perspective view of the implant of FIG. 37, in accordance with an aspect of the present disclosure.
Figure 43:
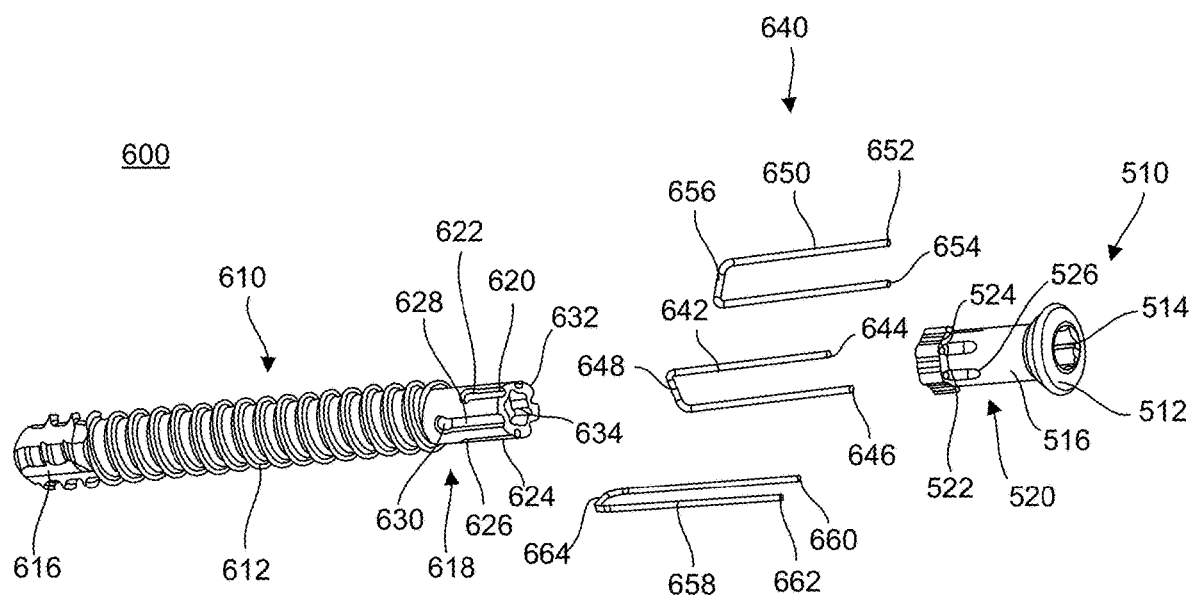
FIG. 43 is an exploded, first end perspective view of the implant of FIG. 37, in accordance with an aspect of the present disclosure.

With continued reference to FIGS. 37-45, the tension member 640 may include at least one suture 642, 650, 658. The sutures 642, 650, 658 may be, for example, braided or monofilament sutures to provide additional flexibility in diastasis. The suture 642, 650, 658 may have a first end 644, 652, 660, a second end 646, 654, 662 and a middle portion 648, 656, 664 positioned between the first end 644, 652, 660 and the second end 646, 654, 662, as shown in FIG. 43. The first end 644, 652, 660 and second end 646, 654, 662 of the tension member 640 may be received within the holes 524 of the head member 510, as shown in FIGS. 37-40. For example, the first end 644, 652, 660 of a suture 642, 650, 658 may be received within a hole 524 that is positioned directly opposite the hole 524 which receives the second end 646, 654, 662 of the same suture 642, 650, 658. In addition, the middle portion 648, 656, 664 may be positioned within the grooves 620, 624, 628 of the anchor member 610 and extend through the openings 622, 626, 630 in the anchor member 610, as best shown in FIG. 40. The middle portion 648, 656, 664 may, for example, extend through the opening 622, 626, 630. The tension member 640 may include, for example, three sutures 642, 650, 658 forming six suture lengths, as shown in FIGS. 41-43. The implant 600 may include, for example, one to four sutures 642, 650, 658 forming two to eight suture lengths, alternatively, the implant 600 may include two to eight single sutures lengths. The sutures 642, 650, 658 may be, for example, braided suture, size #0. The sutures 642, 650, 658 may be made of, for example, polyester, UHMWPE, resorbable material, and the like as known by one of ordinary skill in the art.

Figure 37:
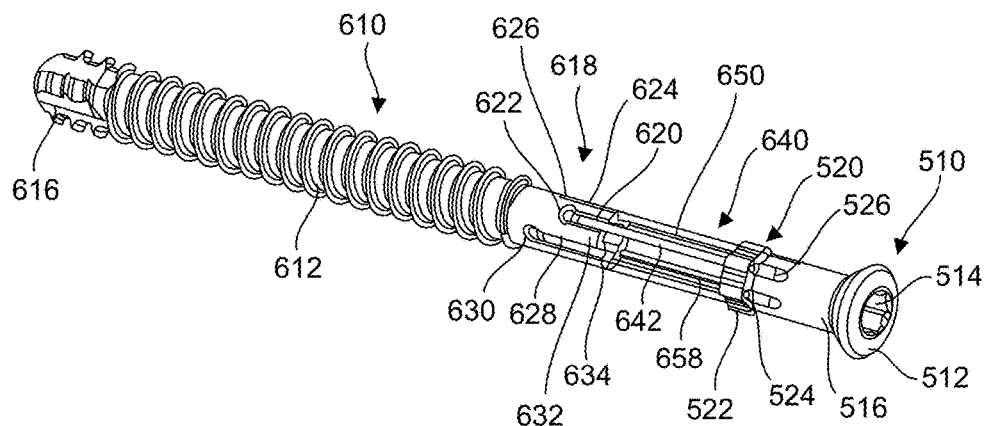
FIG. 37 is a perspective view of yet another implant, in accordance with an aspect of the present disclosure.
Figure 38:
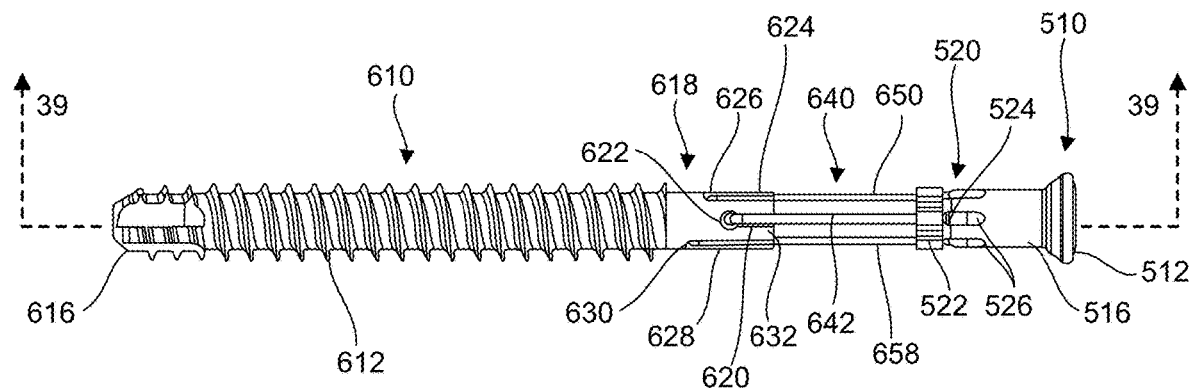
FIG. 38 is a side view of the implant of FIG. 37, in accordance with an aspect of the present disclosure.

The implant 600 may be assembled by inserting the sutures 642, 650, 658 through the openings 622, 626, 630 in the anchor member 610, as shown in FIGS. 37 and 40. Specifically, the first suture 642 may be inserted, for example, through the opening 622 in the anchor member 610 and the middle portion 648 may extend through the opening 622, as shown in FIG. 40. Similarly, the second suture 650 may be inserted, for example, through the opening 626 in the anchor member 610 and the middle portion 656 may extend through the opening 626. In addition, the third suture 658 may be inserted, for example, through the opening 630 in the anchor member 610 and the middle portion 664 may extend through the opening 630. Further, the first suture 642 may be aligned with the grooves 620 in the anchor member 610 and the first and second ends 644, 646 may be inserted into the suture holes 524 in the head member 510. The first and second ends 644, 646 may also be secured in the suture holes 524 to provide the desired gap or space between the anchor member 610 and the head member 510. Similarly, the second suture 650 may be aligned with the grooves 624 in the anchor member 610 and the first and second ends 652, 654 inserted into the suture holes 524 in the head member 510. The first and second ends 652, 654 may also be secured in the suture holes 524 to provide the desired gap or space between the anchor member 610 and the head member 510. In addition, the third suture 658 may be aligned with the grooves 628 and the first and second ends 660, 662 may be inserted into the suture holes 524 in the head member 510. The first and second ends 660, 662 may also be secured in the suture holes 524 to provide the desired gap or space between the anchor member 610 and the head member 510. The first and second ends 644, 646, 652, 654, 660, 662 of each suture 642, 650, 658 may be inserted into suture holes 524 positioned opposite each other. To secure the sutures 642, 650, 658 to the head member 510, the exterior structure forming the suture holes 524 may be deformed to capture or lock the suture ends 644, 646, 652, 654, 660, 662 to the head member 510. After the sutures 642, 650, 658 are secured in the holes 524 of the head member 510 any excess suture material may be removed or cut to a size that fits within the suture recesses 526. The implant 600 may then be inserted into a patient.

Figure 44:
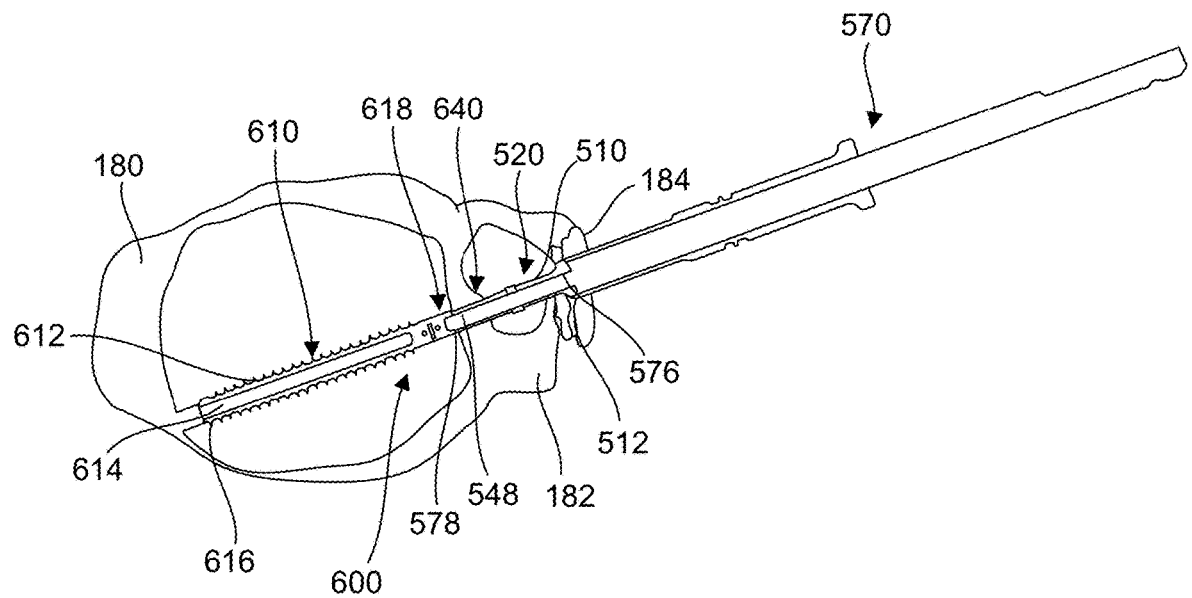
FIG. 44 is a distal, transverse planar view of the bones of FIG. 7 with the implant of FIG. 37 inserted into the drilled opening with a driver instrument, in accordance with an aspect of the present disclosure.
Figure 45:
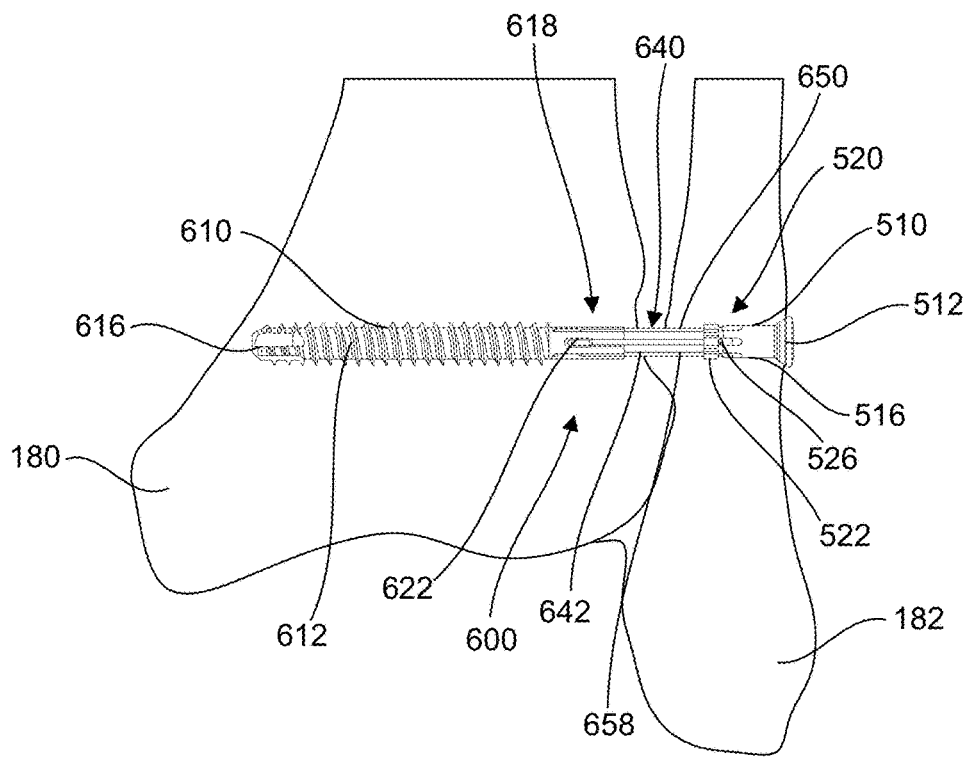
FIG. 45 is a posterior view of the bones of FIG. 44 with the implant of FIG. 37 inserted through the fibula and into the tibia, in accordance with an aspect of the present disclosure.

Referring now to FIGS. 7-9 and 44-45, a method of inserting the implant 600 is shown. The method may include forming the opening 192, as shown in FIGS. 7-9 and described in greater detail above with reference to implant 100, which will not be described again here for brevity sake. Next, as shown in FIG. 44, an insertion instrument 570 may be used to insert the implant 600 into the opening 192 in the bones 180, 182. The instrument 570 engages the anchor member 610 and head member 510 to provide uniform torsional force to the anchor member 610 and head member 510 during insertion. Once the implant 600 is fully inserted, i.e., the inserter 570 may bottom out detaching the inserter 570 from the implant 600. The inserter may then be removed, as shown in FIG. 45. Finally, the surgical procedure may be completed.

Referring now to FIGS. 46-52, another implant 700 is shown. The implant 700 includes a head member 510, an anchor member 610, a tension member 640 and a resorbable spacer 710. The head member 510, anchor member 610, and tension member 640 are described above in greater detail with respect to implants 500 and 660 and will not be described again here for brevity sake. The spacer 710 is positioned between the head member 510 and the anchor member 610 and constrained by the tension members 640. The implant 700 acts as a solid or one piece construct or screw constraining motion until the spacer 710 is resorbed. Once the spacer 710 is resorbed, the implant 700 will have semi-constrained motion as allowed by the tension member 640 positioned between the head member 510 and anchor member 610. The semi-constrained motion approximates the physiological motion of an intact syndesmosis. Therefore, the spacer 710 provides a more constrained joint initially to protect the ligaments during early healing, and once the spacer 710 resorbs, a more natural range of motion is allowed to promote faster healing of the injury. For example, the spacer 710 may take 6-8 weeks to be resorbed and this time may be adjusted based on the type and thickness of the resorbable material used.

Figure 46:
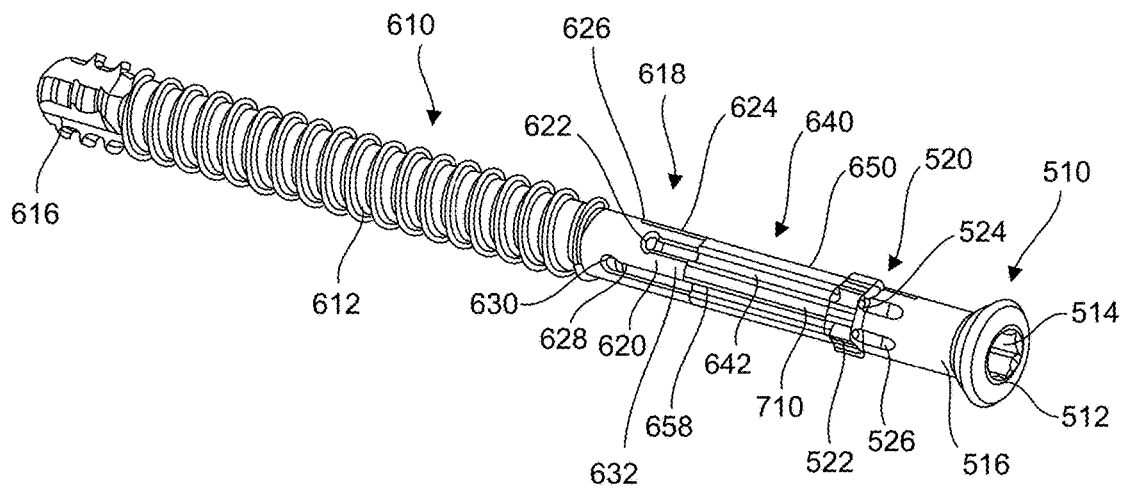
FIG. 46 is a perspective view of another implant, in accordance with an aspect of the present disclosure.
Figure 47:
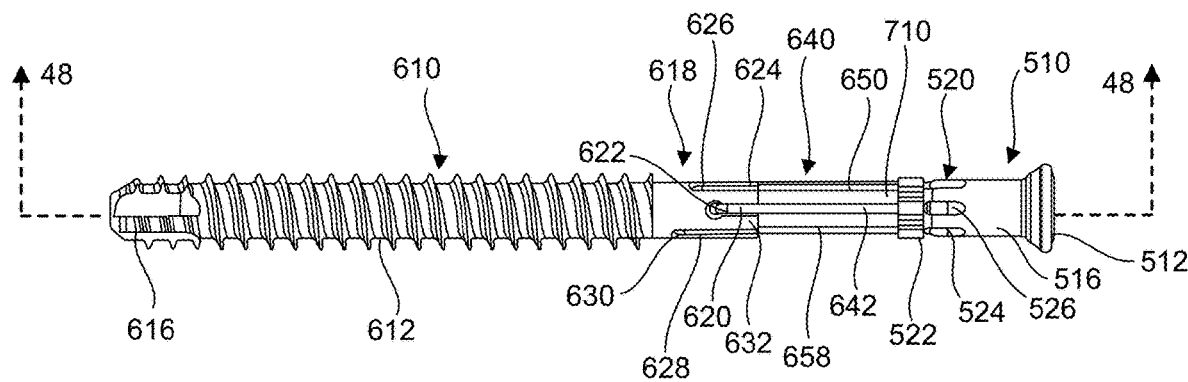
FIG. 47 is a side view of the implant of FIG. 46, in accordance with an aspect of the present disclosure.
Figure 48:
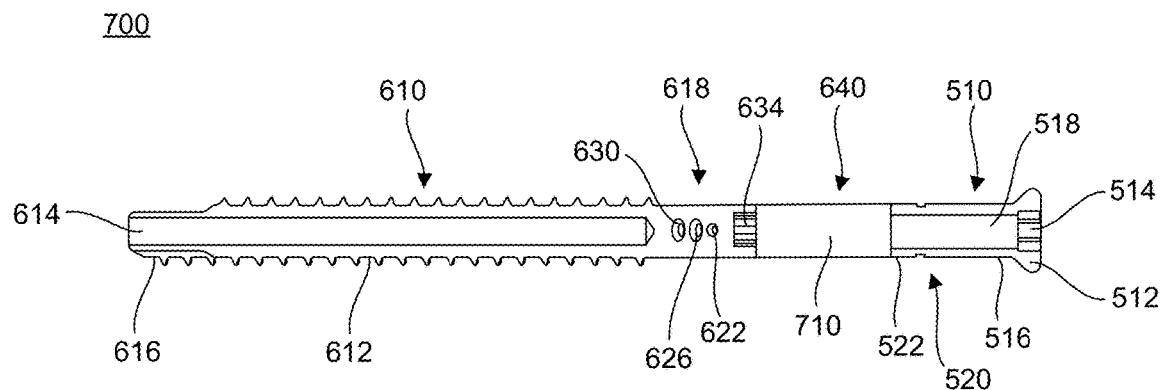
FIG. 48 is a first cross-sectional view of the implant of FIG. 46 taken along line 48-48 in FIG. 47, in accordance with an aspect of the present disclosure.

As shown in FIGS. 48-52, the resorbable spacer 710 may include a first end 712, a second end 714 opposite the first end 712, and a plurality of grooves or channels 716 extending between the first end 712 and the second end 714. The channels 716 may be positioned to align with the grooves 620, 624, 628 of the anchor member 610 and the suture holes 524 and recesses 526 of the head member 510. The channels 716 may also be, for example, sized and shaped or configured to receive the sutures 642, 650, 658 as they extend between the head member 510 and the anchor member 610, as shown in FIGS. 46 and 47. The resorbable spacer 710 may also include a protrusion or extension (not shown) extending away from the second end 714 of the spacer 710 to engage the element 634 of the anchor member 610. In addition, the spacer 710 may have, for example, a solid or cannulated cross-section. The spacer 710 may be made of, for example, PLLA, PGA, PLDA, PL-DLA, copolymers of each, resorbable calcium composites, or any like material as known by one of ordinary skill in the art.

Figure 49:
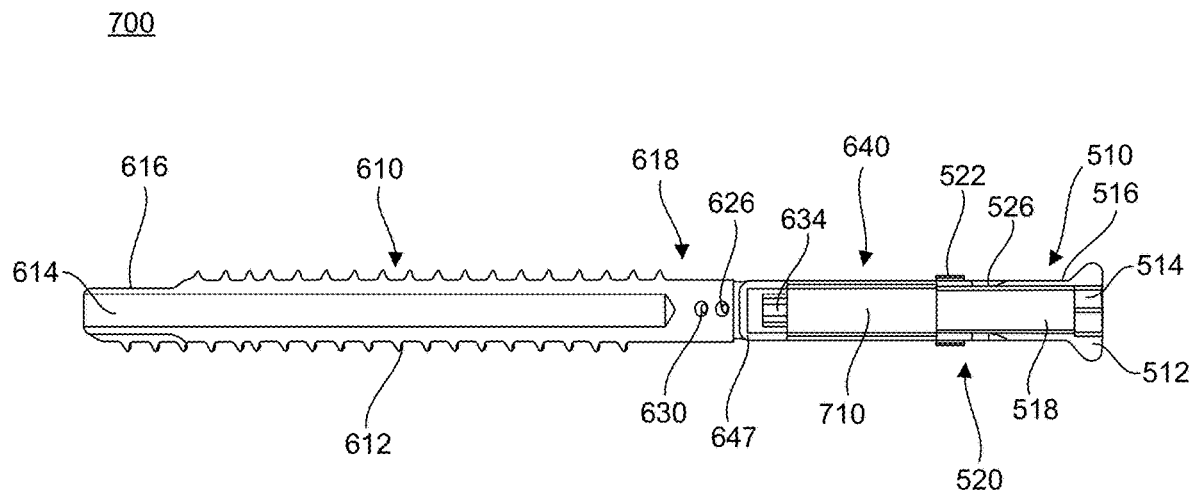
FIG. 49 is a second cross-sectional view of the implant of FIG. 46 taken along a longitudinal line perpendicular to line 48-48 in FIG. 47, in accordance with an aspect of the present disclosure.
Figure 50:
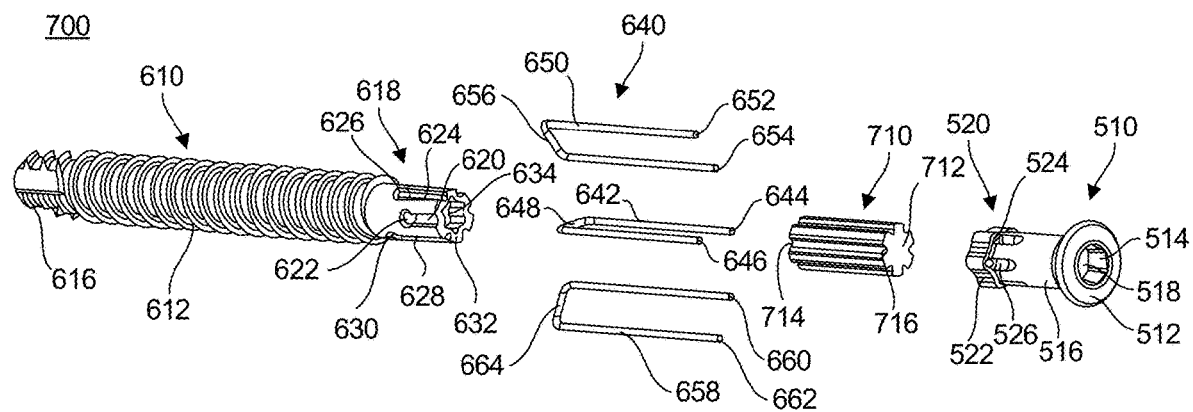
FIG. 50 is an exploded, first end perspective view of the implant of FIG. 46, in accordance with an aspect of the present disclosure.
Figure 51:
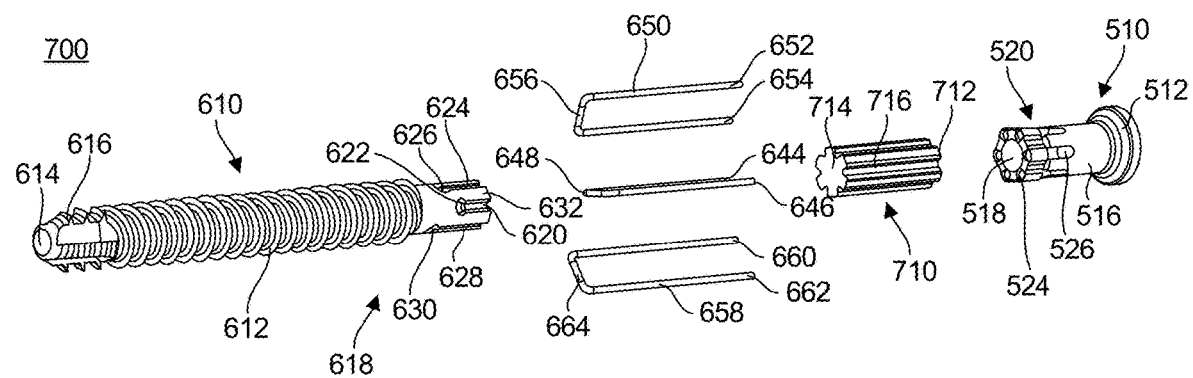
FIG. 51 is an exploded, second end perspective view of the implant of FIG. 46, in accordance with an aspect of the present disclosure.

The implant 700 may be assembled by inserting the sutures 642, 650, 658 through the openings 622, 626, 630 in the anchor member 610, as shown in FIGS. 46-49. Specifically, the first suture 642 may be inserted, for example, through the opening 622 in the anchor member 610 and the middle portion 648 may extend through the opening 622, as shown in FIG. 49. Similarly, the second suture 650 may be inserted, for example, through the opening 626 in the anchor member 610 and the middle portion 656 may extend through the opening 626. In addition, the third suture 658 may be inserted, for example, through the opening 630 in the anchor member 610 and the middle portion 664 may extend through the opening 630. The spacer 710 may be positioned between the anchor member 610 and the head member 510, aligning the channels 716 with the grooves 620, 624, 628 of the anchor member 610 and the suture holes 524 and recesses 526 of the head member 510. The first suture 642 may be aligned with the grooves 620 in the anchor member 610 and the first and second ends 644, 646 may be inserted into the suture holes 524 in the head member 510. The first and second ends 644, 646 may also be secured in the suture holes 524 so that the anchor member 610 and the head member 510 contact the spacer 710. Similarly, the second suture 650 may be aligned with the grooves 624 in the anchor member 610 and the first and second ends 652, 654 inserted into the suture holes 524 in the head member 510. The first and second ends 652, 654 may also be secured in the suture holes 524 so that the anchor member 610 and the head member 510 contact the spacer 710. In addition, the third suture 658 may be aligned with the grooves 628 and the first and second ends 660, 662 may be inserted into the suture holes 524 in the head member 510. The first and second ends 660, 662 may also be secured in the suture holes 524 so that the anchor member 610 and the head member 510 contact the spacer 710. The first and second ends 644, 646, 652, 654, 660, 662 of each suture 642, 650, 658 may be inserted into suture holes 524 positioned opposite each other. To secure the sutures 642, 650, 658 to the head member 510, the exterior structure forming the suture holes 524 may be deformed to capture or lock the suture ends 644, 646, 652, 654, 660, 662 to the head member 510. After the sutures 642, 650, 658 are secured in the holes 524 of the head member 510 any excess suture material may be removed or cut to a size that fits within the suture recesses 526. The implant 700 may then be inserted into a patient.

Figure 52:
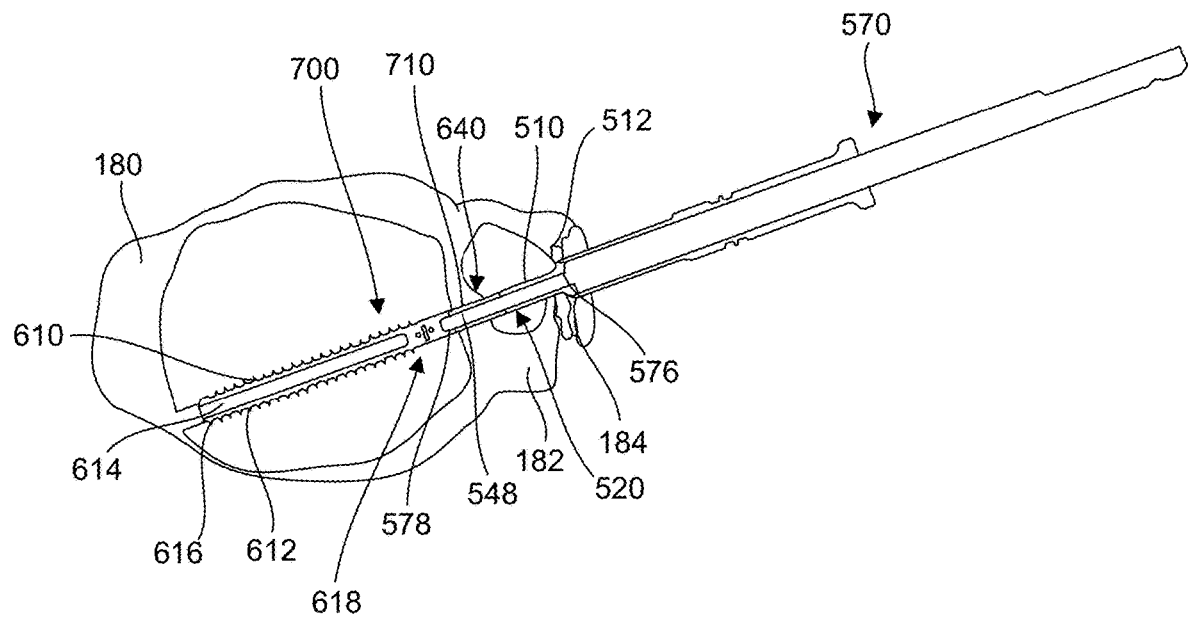
FIG. 52 is a distal, transverse planar view of the bones of FIG. 7 with the implant of FIG. 46 inserted into the drilled opening with a driver instrument, in accordance with an aspect of the present disclosure.

Referring now to FIGS. 7-9 and 52, a method of inserting the implant 700 is shown. The method may include forming the opening 192, as shown in FIGS. 7-9 and described in greater detail above with reference to implant 100, which will not be described again here for brevity sake. Next, as shown in FIG. 52, an insertion instrument 570 may be used to insert the implant 700 into the opening 192 in the bones 180, 182. The instrument 570 engages the head member 510 and passes through the spacer 710 to engage the anchor member 610 to provide uniform torsional force to the entire implant 700 during insertion. Alternatively, if the head member 510 and/or spacer 710 are not cannulated, the instrument 570 may engage the tool engagement opening 514 of the head member 510 and the spacer 710 may engage the instrument opening 548 of the anchor member 610 to provide the torsional force to the anchor member 610. Once the implant 700 is fully inserted, i.e., the inserter 570 bottoms out causing the inserter 570 to detach from the implant 700. The implant 700 may then be removed. Finally, the surgical procedure may be completed.

Figure 53:
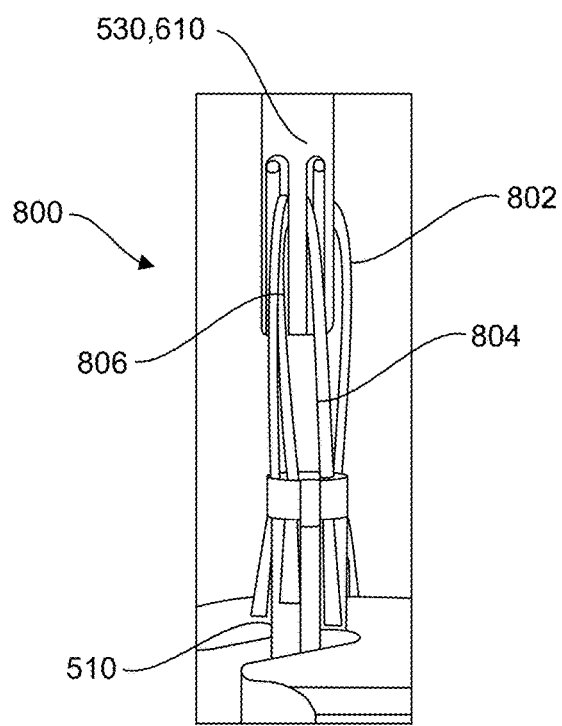
FIG. 53 is a side view of an alternative middle portion of the implants of FIGS. 24, 37, and 46, in accordance with an aspect of the present disclosure.

Referring now to FIG. 53, another tension member 800 is shown. The tension member 800 may be used with, for example, implants 500, 600, 700. The tension member 800 may include at least one suture 802, 804, 806. For example, the tension member 800 may include a first suture 802, a second suture 804 and a third suture 806. The lengths of the sutures 802, 804, 806 may vary initially. The shortest suture 802, 804, 806 will define the gap or space between the head member 510 and anchor member 530, 610 and the other two sutures 802, 804, 806 will each have a predefined laxity. Once an implant 500, 600, 700 having the tension member 800 is implanted into a patient, the shortest suture 802, 804, 806 will define the amount of motion that is possible between the tibia 180 and fibula 182. Over time, the shortest suture 802, 804, 806 will break and the next shortest suture 802, 804, 806 will then define the amount of motion permitted between the tibia 180 and fibula 182. The sutures 802, 804, 806 will continue to break over time allowing for the relative distance between the head member 510 and anchor member 530, 610 to incrementally increase. As the relative distance between the head member 510 and anchor member 530, 610 incrementally increases, the amount of physiologic motion between the bones 180, 182 also increases over time. The number and strength of the sutures 802, 804, 806 may be selected, such that once all of the sutures 802, 804, 806 have broken, the syndesmosis should be theoretically healed.

Figure 54:
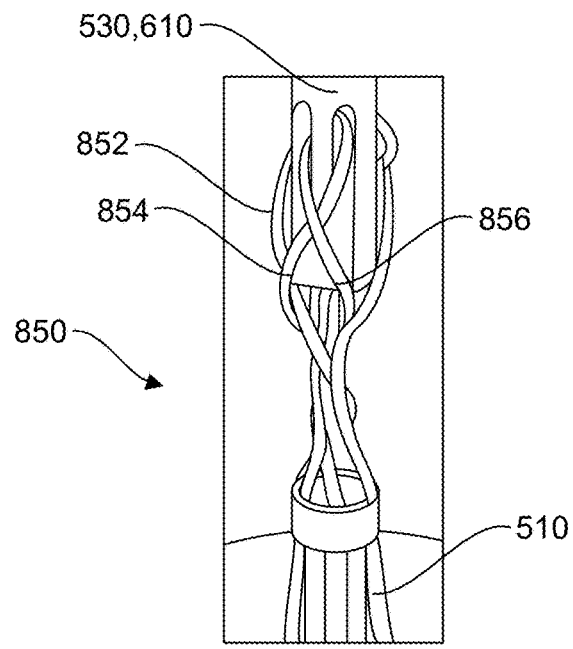
FIG. 54 is a side view of another alternative middle portion of the implants of FIGS. 24 and 37 in a contracted position, in accordance with an aspect of the present disclosure.
Figure 55:
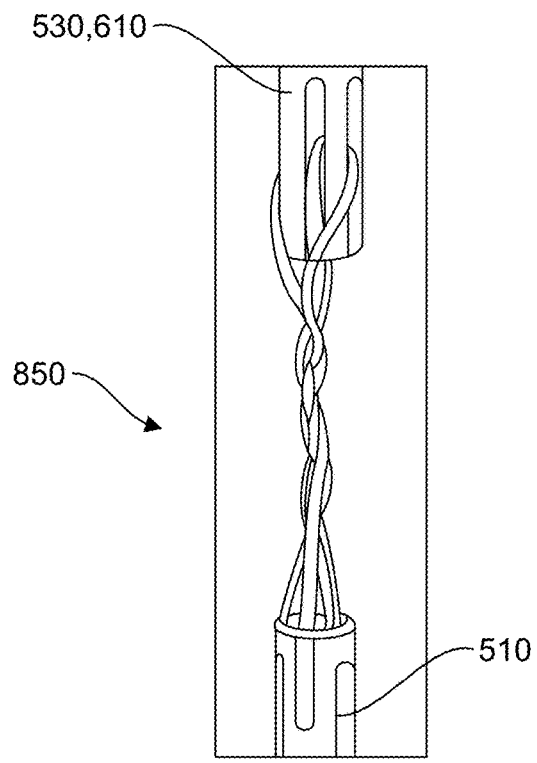
FIG. 55 is a side view of the middle portion of FIG. 54 in an extended position, in accordance with an aspect of the present disclosure.
Figure 56:
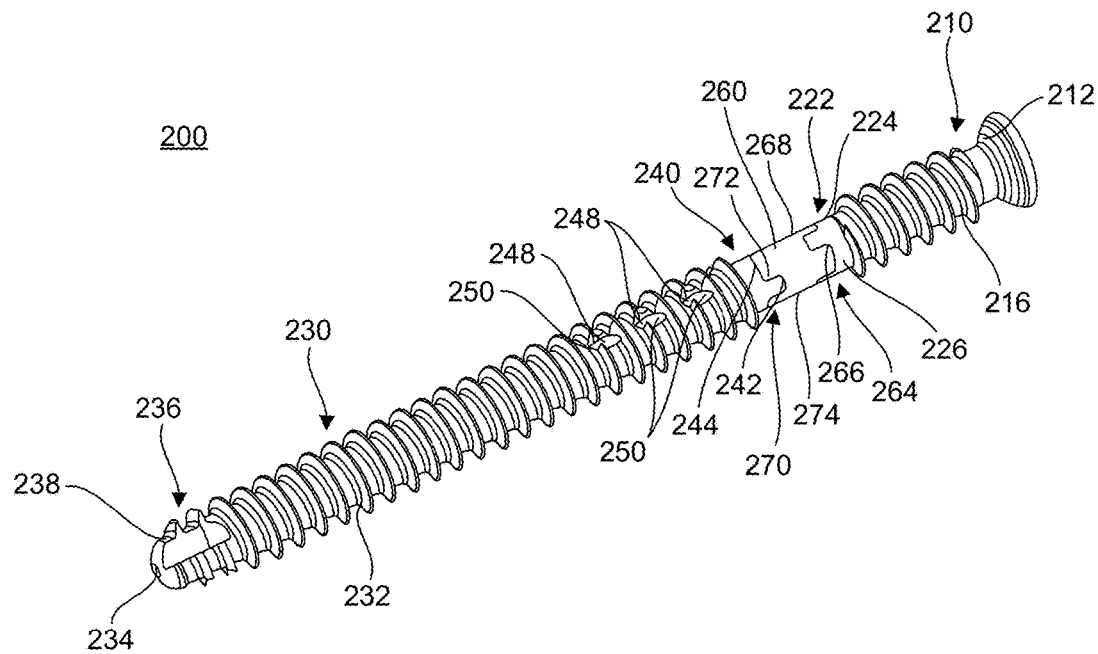
FIG. 56 is a perspective view of another implant, in accordance with an aspect of the present disclosure.
Figure 57:
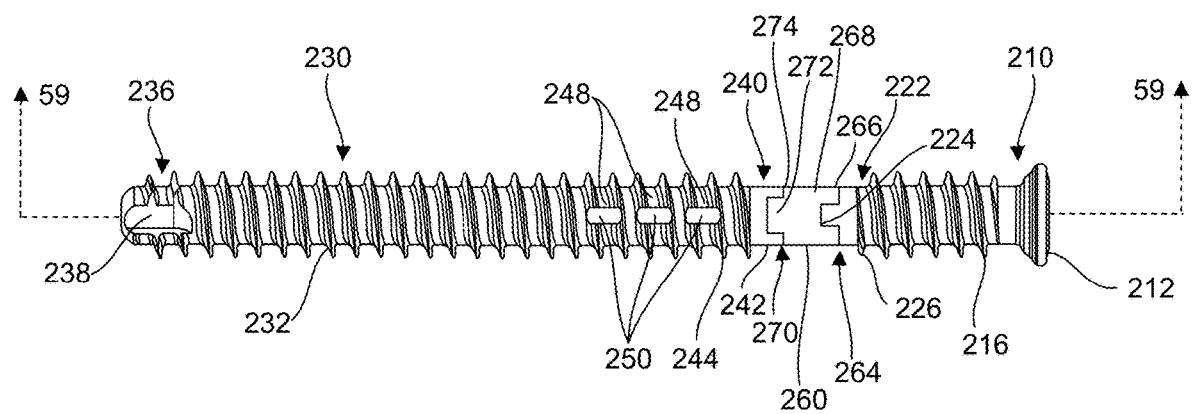
FIG. 57 is a first side view of the implant of FIG. 56, in accordance with an aspect of the present disclosure.
Figure 58:
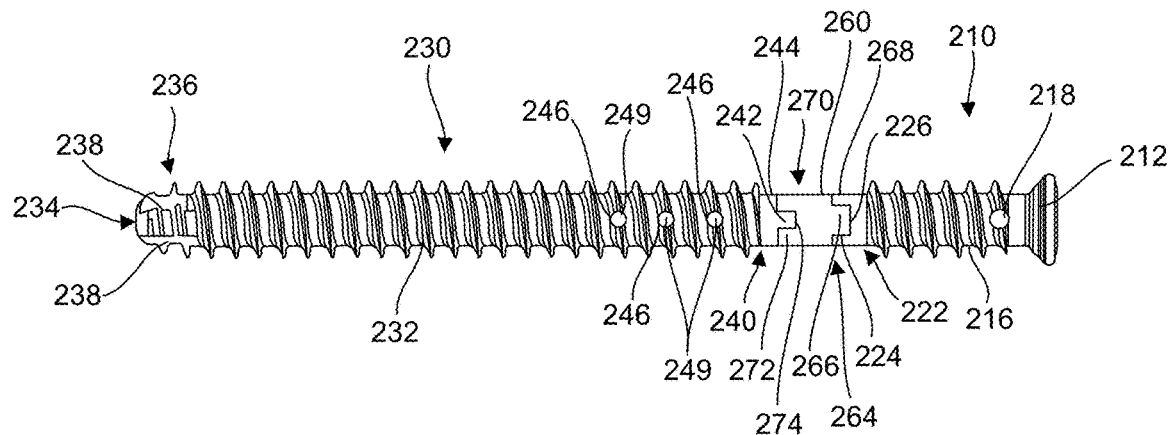
FIG. 58 is a second side view of the implant of FIG. 56, in accordance with an aspect of the present disclosure.

Referring now to FIGS. 54 and 55, another alternative tension member 850 is shown. The tension member 850 may be used with, for example, implants 500, 600. The tension member 850 may include at least one suture 852, 854, 856. For example, the tension member 850 includes a first suture 852, a second suture 854 and a third suture 856. The sutures 802, 804, 806 may be woven such that tension pulls them towards the axis of the implant 500, 600 and allows for diastatic motion between the tibia 180 and fibula 182.

Figure 62:
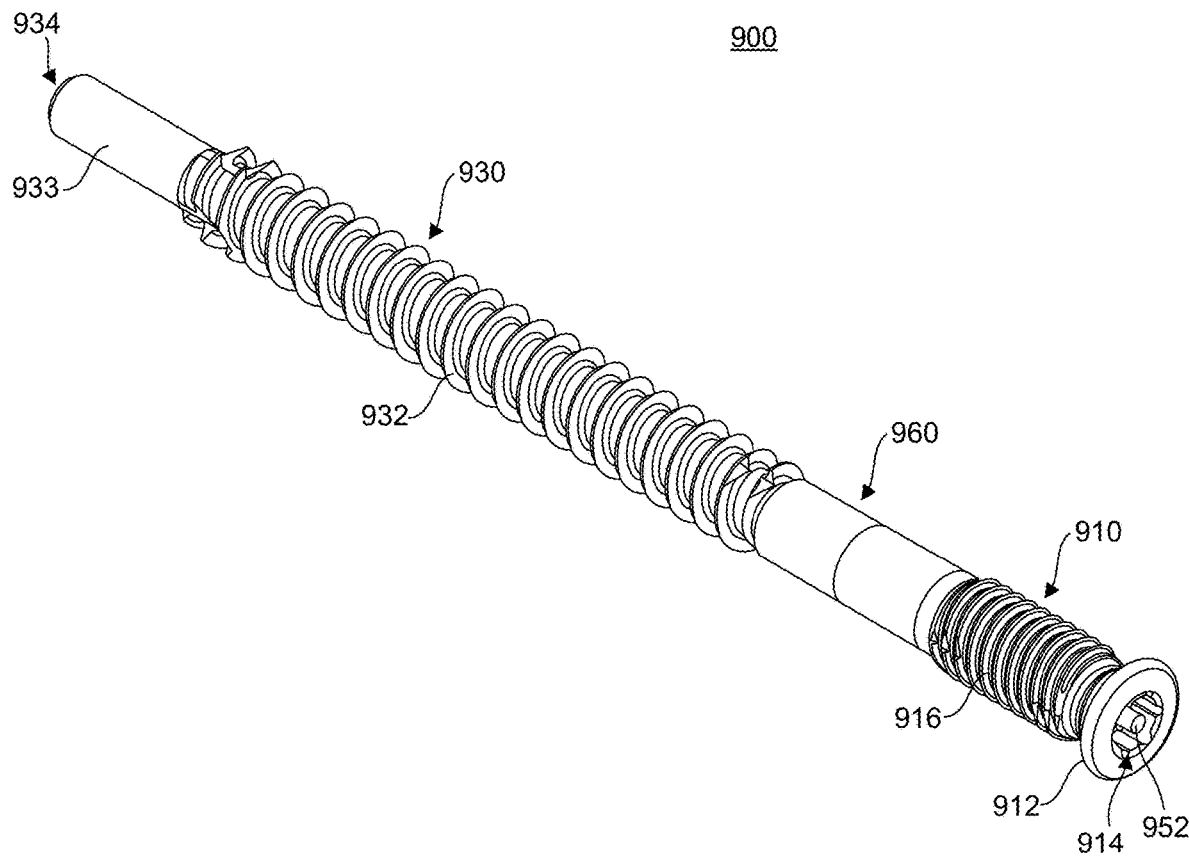
FIG. 62 is a perspective side view of another implant, in accordance with an aspect of the present disclosure.
Figure 63:
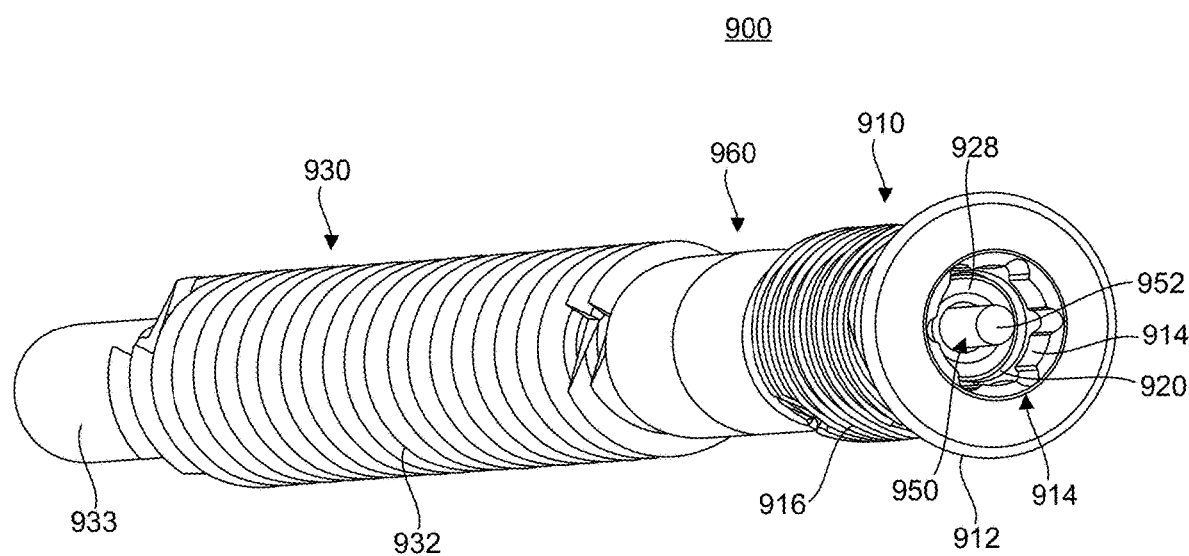
FIG. 63 is another perspective side view of the implant of FIG. 62, in accordance with an aspect of the present disclosure.
Figure 64:
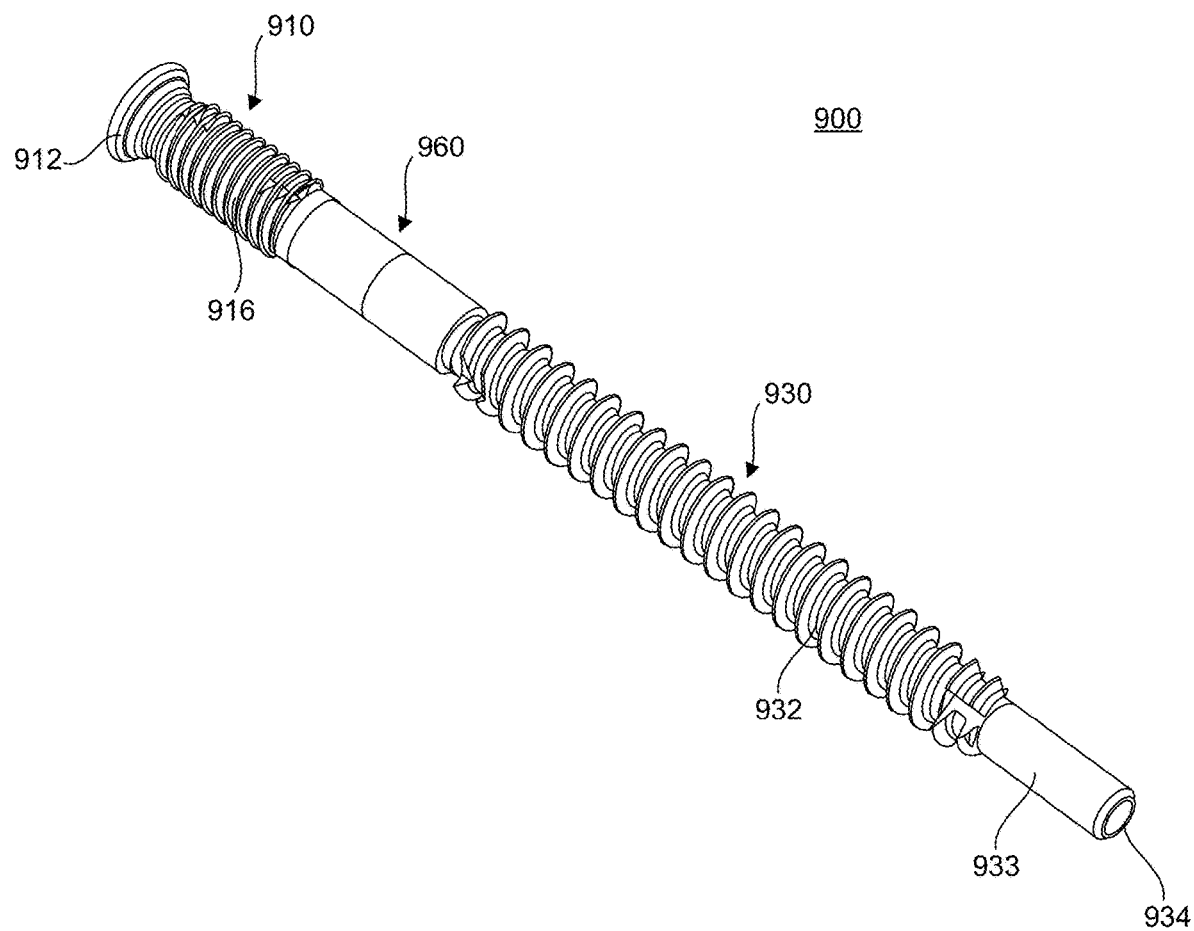
FIG. 64 is another perspective side view of the implant of FIG. 62, in accordance with an aspect of the present disclosure.
Figure 65:
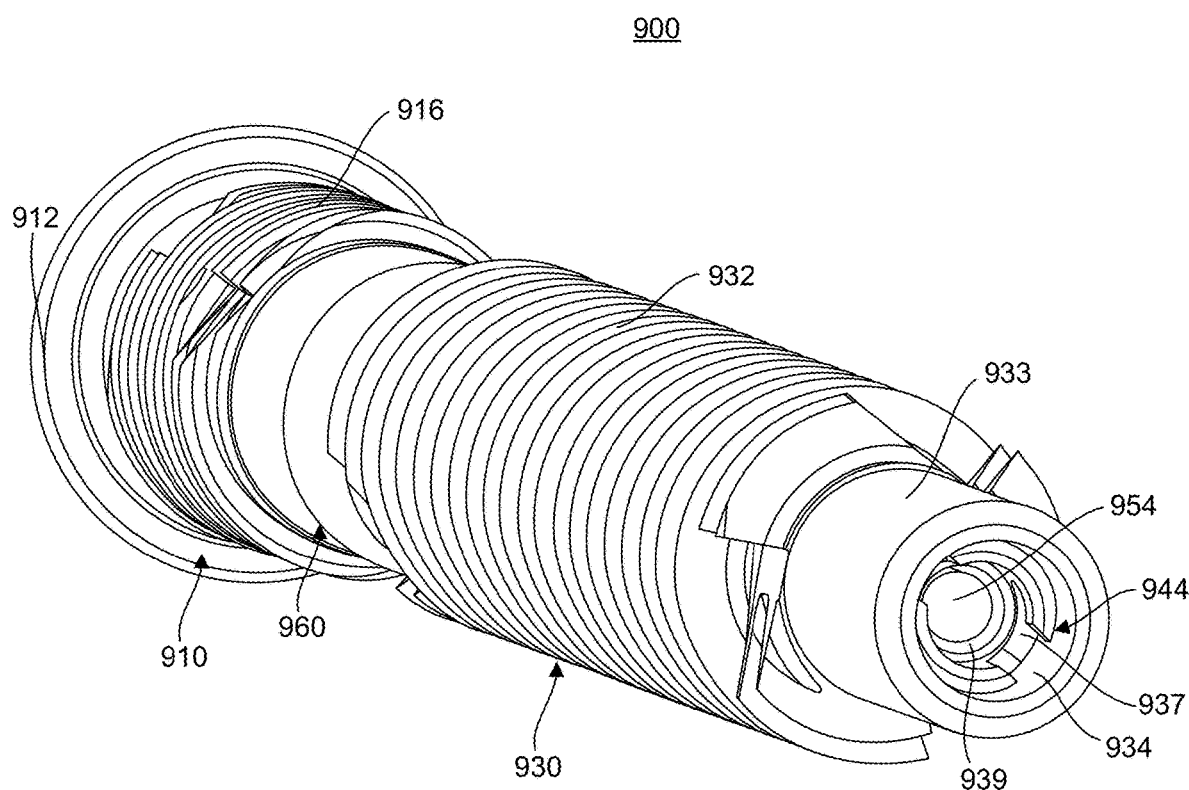
FIG. 65 is another perspective side view of the implant of FIG. 62, in accordance with an aspect of the present disclosure.
Figure 66:
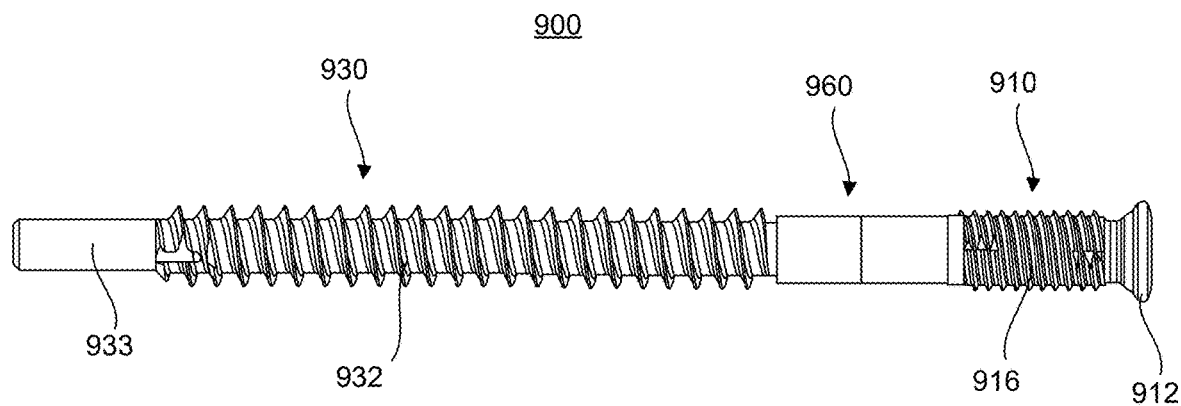
FIG. 66 is a side view of the implant of FIG. 62, in accordance with an aspect of the present disclosure.
Figure 67:
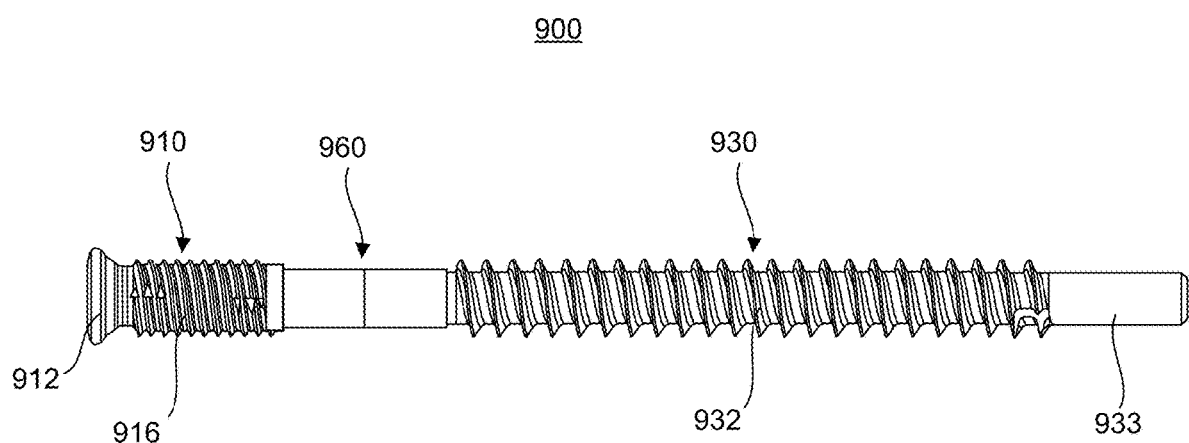
FIG. 67 is another side view of the implant of FIG. 62, in accordance with an aspect of the present disclosure.
Figure 68:
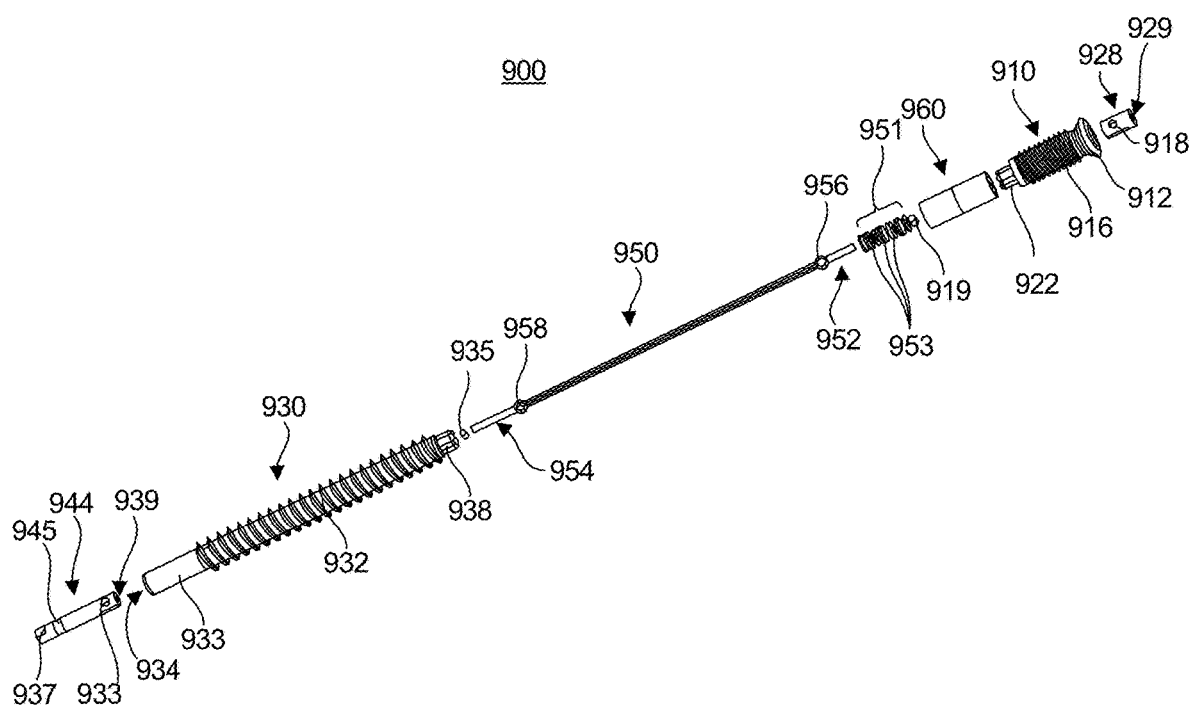
FIG. 68 is an exploded perspective side view of the implant of FIG. 62, in accordance with an aspect of the present disclosure.
Figure 69:
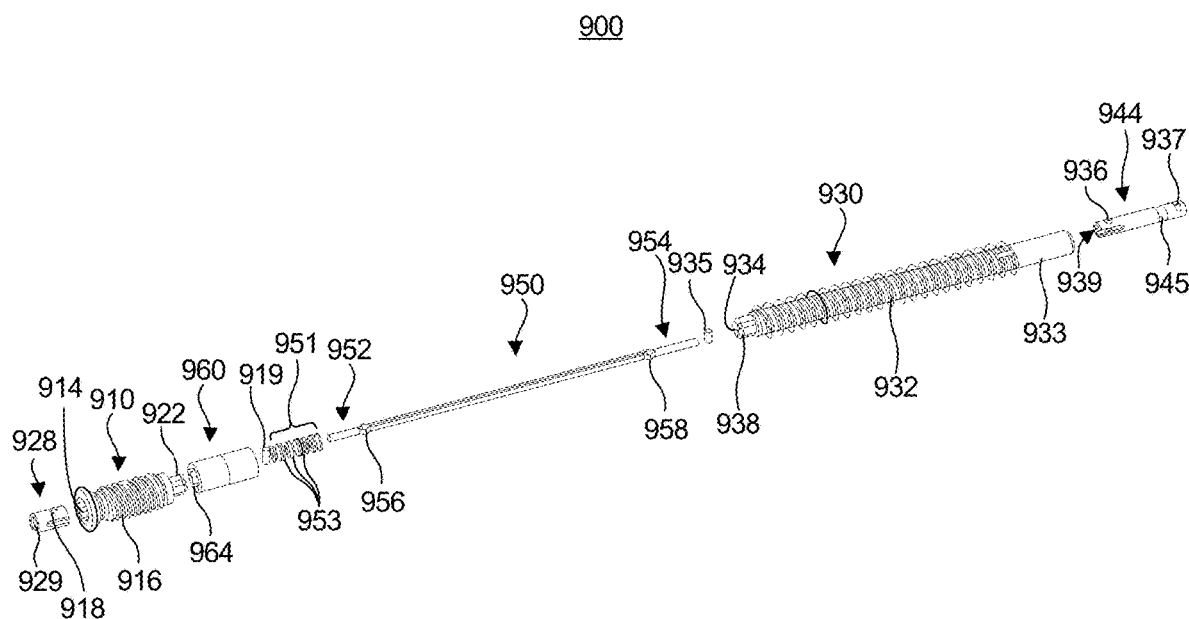
FIG. 69 is another exploded perspective side view of the implant of FIG. 62, in accordance with an aspect of the present disclosure.
Figure 70:
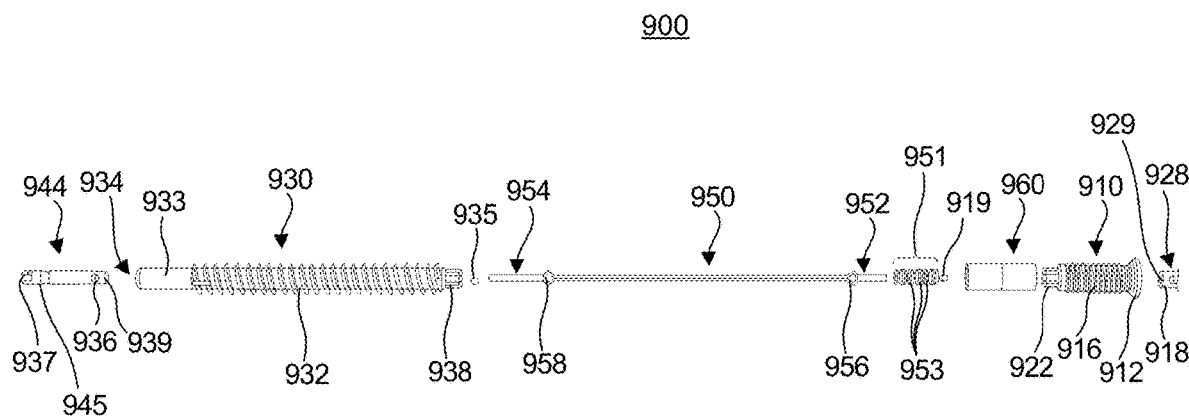
FIG. 70 is an exploded side view of the implant of FIG. 62, in accordance with an aspect of the present disclosure.
Figure 71:
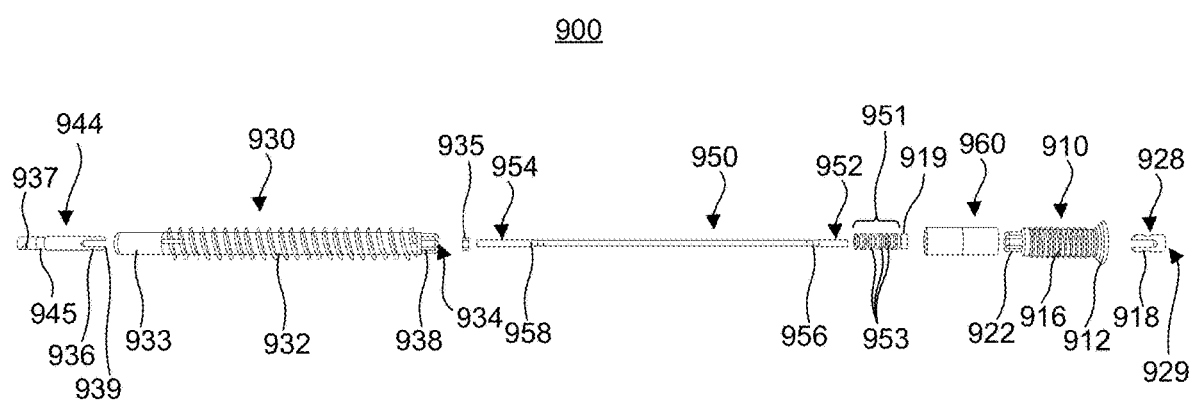
FIG. 71 is another exploded side view of the implant of FIG. 62, in accordance with an aspect of the present disclosure.
Figure 72:
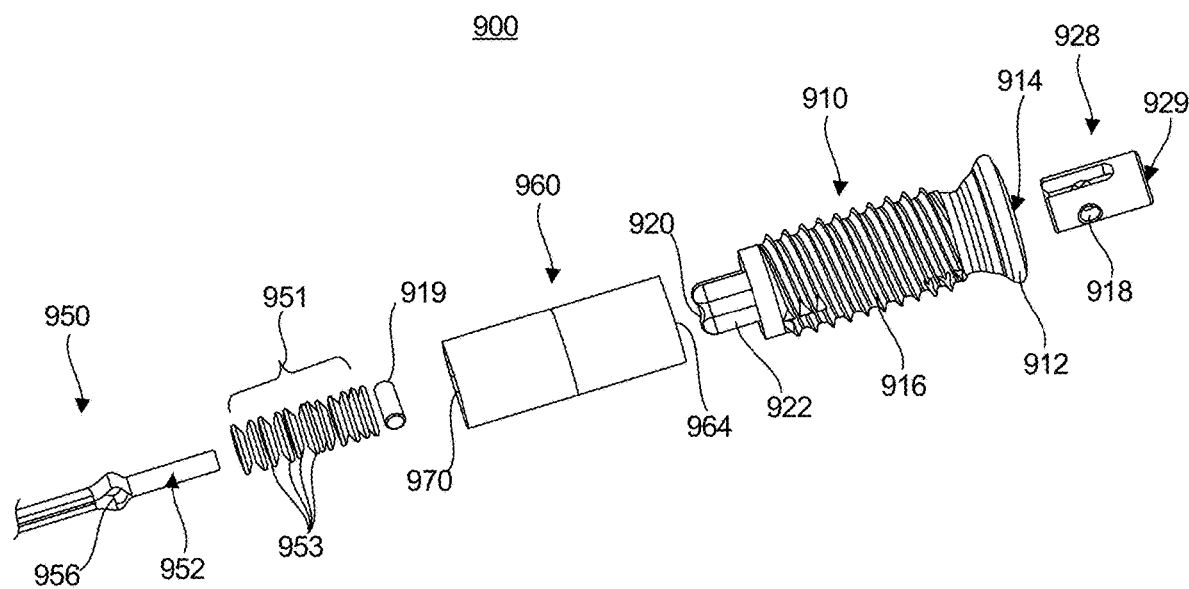
FIG. 72 is an exploded perspective side view of the implant of FIG. 62 illustrating a tension member, resilient member, head pin, coupling, head member and head post of the implant, in accordance with an aspect of the present disclosure.
Figure 73:
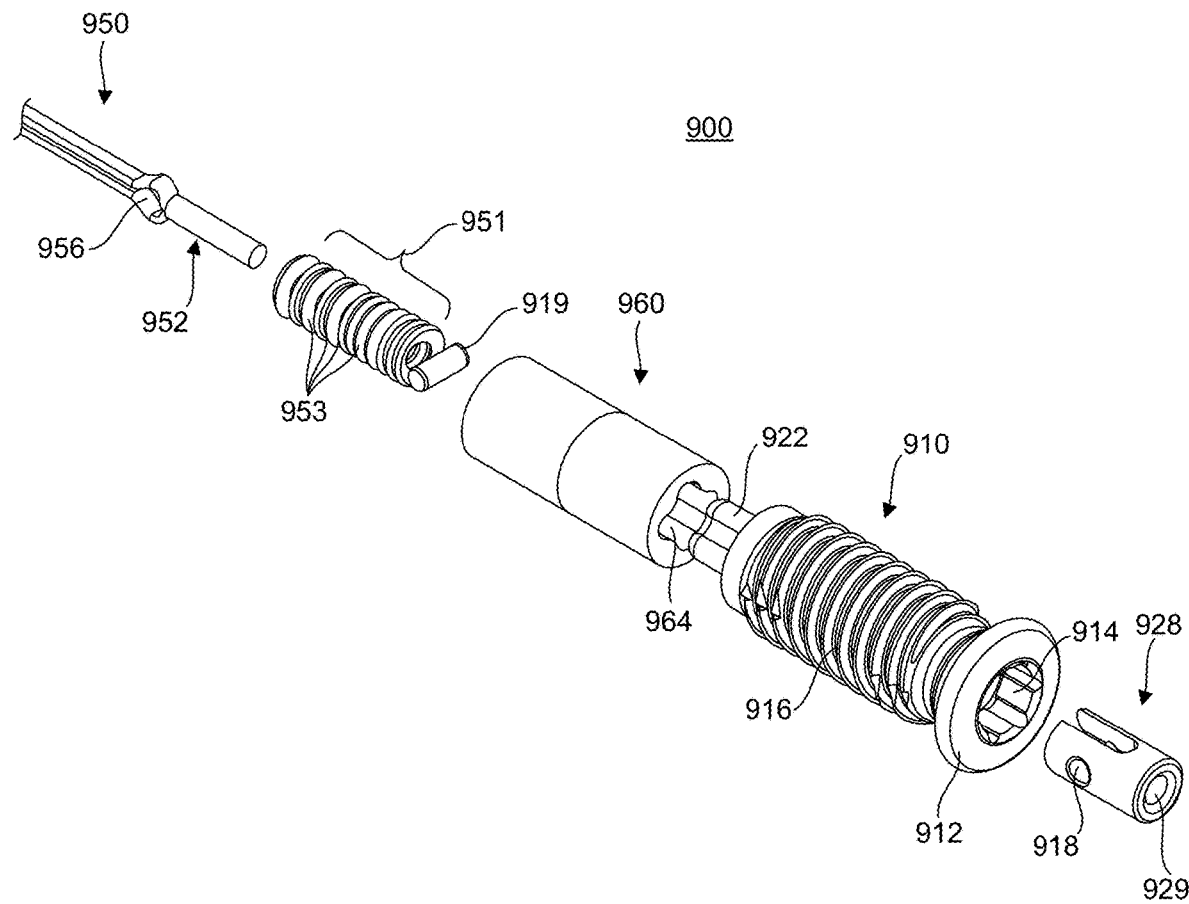
FIG. 73 is another exploded perspective side view of the implant of FIG. 62 illustrating the tension member, resilient member, head pin, coupling, head member and head post of the implant, in accordance with an aspect of the present disclosure.
Figure 74:
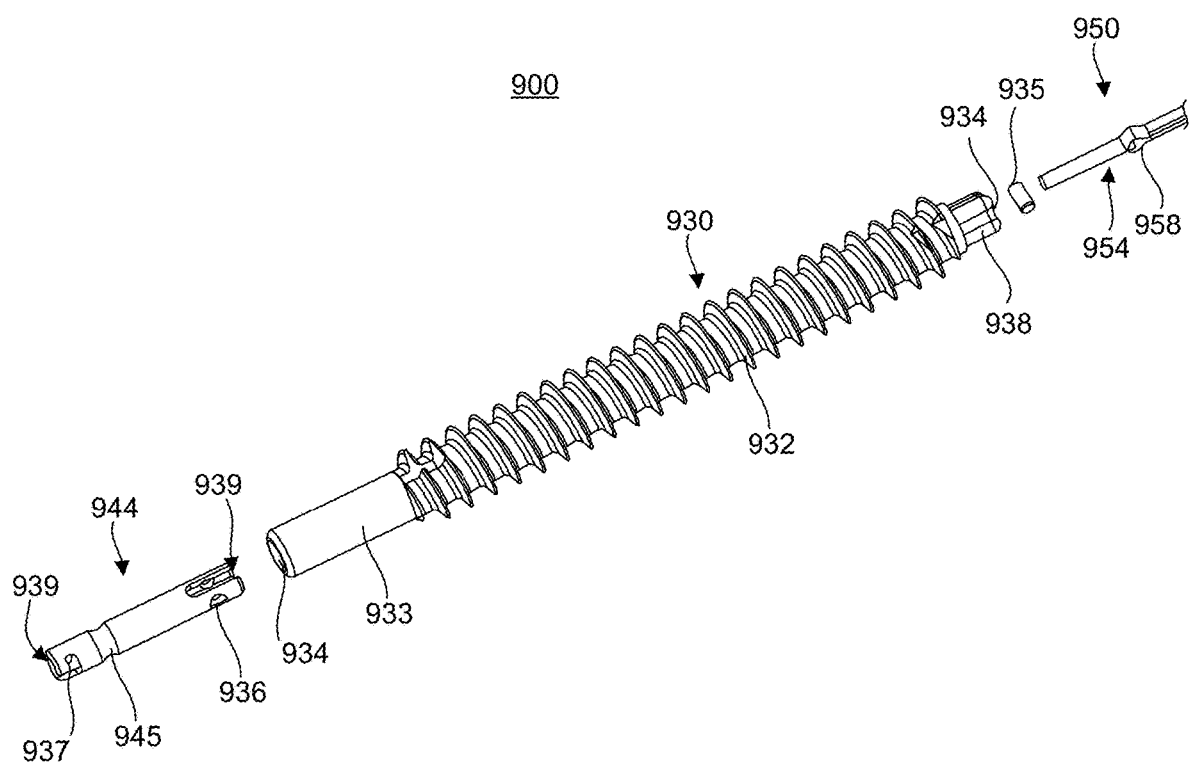
FIG. 74 is an exploded perspective side view of the implant of FIG. 62 illustrating a tension member, tip pin, anchor member and tip post of the implant, in accordance with an aspect of the present disclosure.
Figure 75:
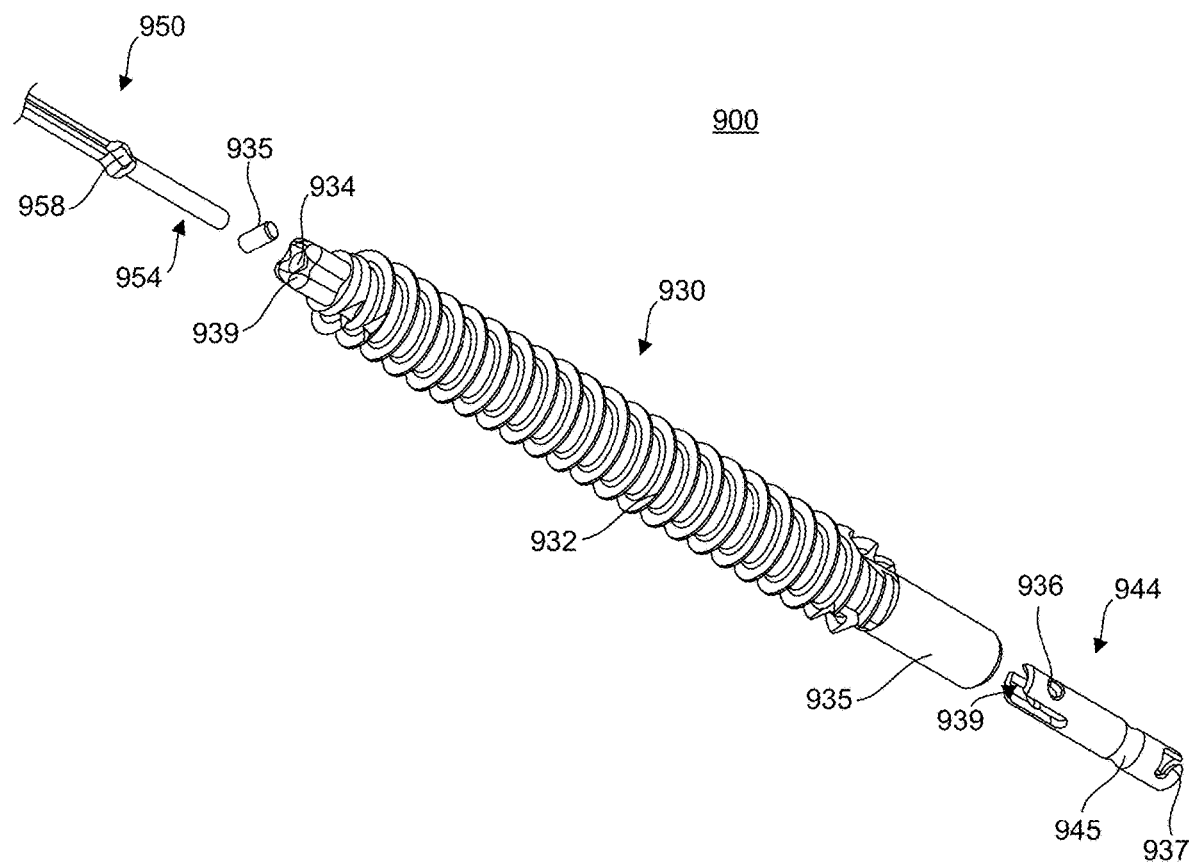
FIG. 75 is another exploded perspective side view of the implant of FIG. 62 illustrating the tension member, tip pin, anchor member and tip post of the implant, in accordance with an aspect of the present disclosure.
Figure 76:
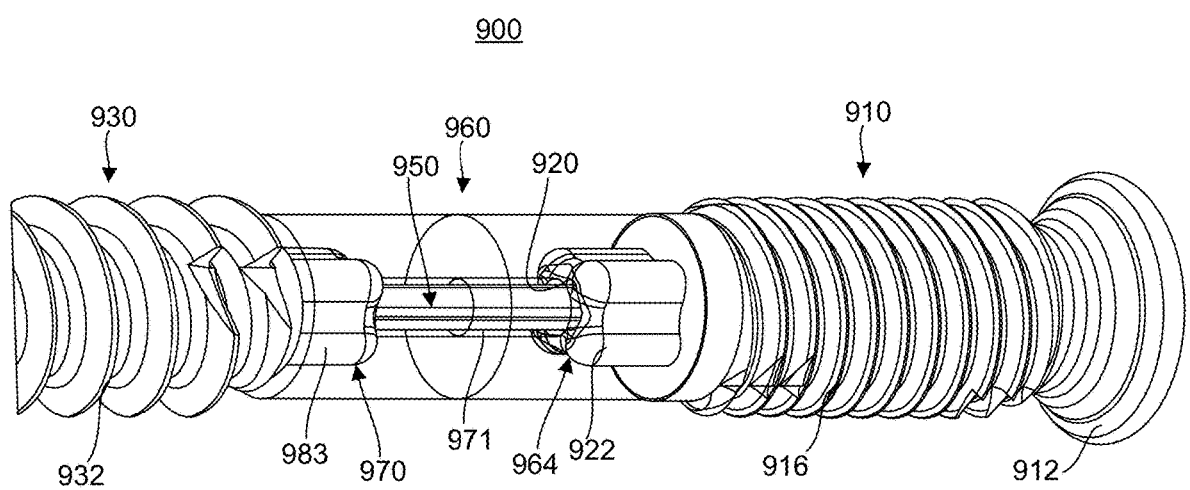
FIG. 76 is a side perspective view of the implant of FIG. 62 illustrating the engagement of the tension member, anchor member and head member of the implant, in accordance with an aspect of the present disclosure.
Figure 77:
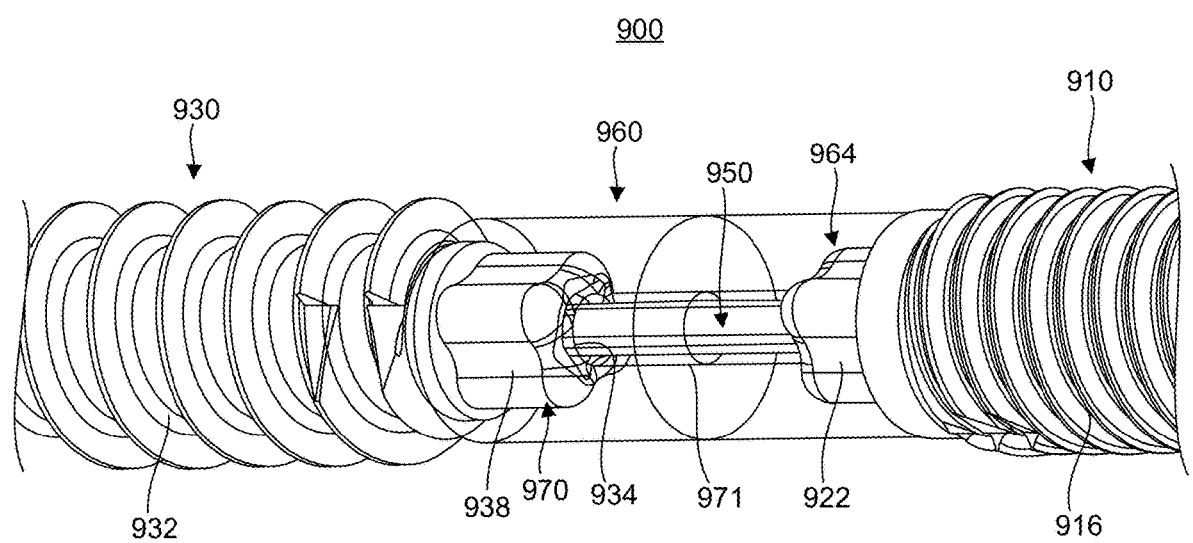
FIG. 77 is another side perspective view of the implant of FIG. 62 illustrating the engagement of the tension member, anchor member and head member of the implant, in accordance with an aspect of the present disclosure.

An exemplary embodiment of another implant according to the present disclosures is shown in FIGS. 62-87 and generally indicated with the reference numeral 900. Some aspects, elements and/or functions of exemplary implant 900 are the same or similar in structure and/or function, at least in part, to the exemplary implants 100, 200, 300, 400, 500, 600 and/or 700 described above and shown in FIGS. 1-62, and therefore like reference numerals preceded by the numeral "9" are used to indicate like components, aspects, configurations, functions or processes, and the description above directed thereto (and the alternative embodiments thereof) equally applies to the implant 900.

As shown in FIGS. 62-87, the implant 900 includes a head member or fibula member 910, a head post 928, an anchor member or tibia member 930, a tip post 944, a tension member 950, a biocompatible coupling 960 and at least one resilient and/or elastic tensioning member 951. The coupling 960 is positioned between the head member 910 and the anchor member 930 and allows for the anchor member 930 to be secured into the bones 980, 982 when the head member 910 is torqued or rotated. The tension member 950 may extend at least partially through a cannulated opening, through hole or passageway extending through the implant 900 along the longitudinal axis thereof, such as at least partially through the head post 928 (which is positioned within an opening of the head member 910, the tip post 944 (which is positioned within an opening of the anchor member 930) and the coupling 960.

In one embodiment, the axial lengths of the head member 910 and the coupling 960 may remain constant, while the length of the anchor member 930 may be variable to correspond to the varying size of a patient's bones. Alternatively, in another embodiment, the head member 910 may, for example, be available in multiple lengths to correspond to the varying sizes of patient bones and the lengths of the anchor member 930 and the coupling 960 may remain constant. In yet another embodiment, both the head member 910 and the anchor member 930 may be available in multiple lengths to allow for selection based on the size of the patient's bones and the coupling 960 may remain constant.

As shown in at least FIGS. 62-73, 76, 77, 82 and 86, the head member 910 may comprise a shaft portion 916 with a head portion 912 at a first end and an engagement end or projection 922 at a second end. The shaft portion 916 may be, for example, threaded along a portion of the shaft, such as a portion extending from or proximate to the head portion 912. The head member 910 also includes an axially/longitudinally extending through hole, cannulated opening or passageway 920 that extends between the first and second ends, as shown in FIGS. 62-73, 76, 77, 82 and 86. The head portion 912 includes a tool engagement opening 914 having an irregular or non-circular cross-sectional shape so that a correspondingly shaped tool can mate therewith and apply a torque to the implant 900 to rotate the implant 900 about its axis. The engagement opening 914 may include or be a portion of the through hole 920.

As shown in at least FIGS. 68-73, 76 and 77, the engagement end 922 of the head member 910 may be irregular or non-circular in cross-section, and a first end of the coupling 960 may include a corresponding or mating aperture 964, so that the head member 910 is able to transfer torque to the coupling 960 when the engagement end 922 is seated or positioned within the aperture 964. In some embodiments, the engagement end 922 of the head member 910 may include at least one protrusion or lobe 924 and at least one groove or recess 926, as shown in FIGS. 68-73, 76 and 77. For example, in the depicted embodiment, the engagement end 922 includes four lobes 924 alternating with four recesses 926.

The anchor member 930 may comprise a shaft portion 932 with an engagement end or protrusion 938 at a first end and a crimp portion 933 at a second end, as shown in FIGS. 62-71 74, 75, 78, 83 and 84. The threaded shaft 932 may be, for example, threaded along a portion of the shaft, such as a portion extending from or proximate to the engagement end 938. An end portion of the threads of the anchor member 930 proximate to the second end may include at least one cutting element, for example, at least one flute (such as a cutting flute). The crimp portion 933 may be a non-threaded portion of the anchor member 930 that extends from the threaded portion to the second end of the anchor member 930. The anchor member 930 also includes an axially/longitudinally extending through hole, cannulated opening or passageway 934 that extends between the first and second ends, as shown in FIGS. 62-71 74, 75, 78, 83 and 84.

As shown in at least FIGS. 68-70 and 74-77, the engagement end 938 of the anchor member 930 may be irregular or non-circular in cross-section, and a second end of the coupling 960 may include a corresponding or mating aperture 970, so that the coupling 960 is able to transfer torque to the anchor member 930 when the engagement end 938 is seated or positioned within the aperture 970. In some embodiments, the engagement end 938 of the anchor member 930 may include at least one protrusion or lobe 924 and at least one groove or recess 926, as shown in FIGS. 68-70 and 74-77. For example, in the depicted embodiment, the engagement end 938 includes four lobes 924 alternating with four recesses 926.

The aperture 964 at the first end of the coupling 960 and the aperture 970 at the second end of the coupling 960 may be in communication via an axially/longitudinally extending through hole, cannulated opening or passageway 971 that extends through the coupling 960 between the first and second ends thereof. The apertures 964, 970 at the first and second ends of the coupling 960 may thereby include or be a portion of the through hole 920.

The coupling 960 may couple the head member 910 and the anchor member 930 together such that the implant 900, as a whole, can be inserted or implanted (via rotation or torque applied by a tool via the engagement opening 914 of the head portion 912) into first and second bones like a screw. The implant 900 may be implanted such that the coupling 960 is positioned, at least partially, between the joint or space between the first and second bones. The coupling 960 may be made of a bioresorbable material so that after implantation, the implant 900 provides a first period of substantially rigid fixation of the first and second bones, and then after the coupling 960 is absorbed/resorbed, a second phase of semi-constrained and/or dynamic motion between the first and second bones (provided by the tension member 950, as described later). For example, the implant 900 may be inserted into a tibia and fibula after a syndesmotic reduction to only temporarily fix the tibia and fibula. In some such embodiments, the implant 900 may be inserted into a tibia and fibula following a repair of an ankle fracture, such as a fibula fracture. The coupling 960 may be formed of any bioresorbable material, such as for example one or more bioabsorbable polymers (PGA, PLA, PLLA, PLDA, PL-DLA, PLGA (e.g., PLGA 91:15), PDS and copolymers thereof), one or more bioabsorbable metal (e.g., a magnesium alloy), ultra-high-molecular-weight polyethylene (UHMWPE), or a combination thereof (or any other like bioresorbable material as known by one of ordinary skill in the art).

As shown in FIGS. 68-78 and 80-87, the tension member 950 may be an elongated structure or member that extends from or proximate to (and is affixed to) the second end of the anchor member 930 and at least proximate to (and is affixed to) the head portion 912 of the head member 910. The tension member 950 may be of any configuration or structure. The tension member 950 may be, for example, a stranded cerclage cable or similar construct. The tension member 950 may also be made of, for example, titanium, stainless steel, polymers, polyester, polypropylene or UHMWPE suture, co-braids thereof, or a like material, as known by one of ordinary skill in the art. The tension member 950 may be, for example, a suture (e.g., a braided suture), such as a single cross-section strand of suture or multiple loops of suture. For example, the tension member 950 may be a UHMWPE and polypropylene co-braid suture. The tension member 950 may or may not be elastically axially/longitudinally stretchable or deformable.

In the exemplary illustrated embodiment of the implant 900, the tension member 950 comprises a bifurcated suture loop. As shown in FIGS. 68-78 and 80-87, the tension member 950 may include a medial bifurcated portion extending between the first and second end portions 952, 954. The first and second end portions 952, 954 include non-bifurcated, closed or solid portions that define ends of the medial bifurcated portion. As shown in FIGS. 68-78 and 80-87, the medial bifurcated portion of the tension member 950 may include first and second openings or portions 956, 958 adjacent to the non-bifurcated or solid portions of the first and second closed end portions 952, 954. As explained further below, the first and second openings 956, 958 of the tension member 950 are configured to accommodate or accept pins extending therethrough so that the tension member 950 can be pulled into tension (or apply tensile forces that act to pull the head member 910 and the anchor member 930 together along the longitudinal axis).

The first end portion 952 of the tension member 950 may be coupled to the head member 910 within the cannulated opening 920 thereof via the head post 928, as shown in FIGS. 62, 63, 82 and 85-87. The head post 928 may be contained or positioned within the cannulated opening 920 of the head member 910. Specifically, the cannulated opening 952 of the head member 910 is configured to allow the head post 928 to axially slide or translate therein. As shown in FIGS. 62, 63, 82 and 85-87, the cannulated opening 952 of the head member 910 includes an enlarged portion positioned proximate to the first end/head portion 912 that is sized and shaped to contain the head post 928 and allow the head post 928 to axially travel therein. The cannulated opening 952 of the head member 910 also includes a reduced or narrow portion positioned proximate to the second end/engagement end 922 of the head member 910 that is sized and shaped to allow the tension member 950 to pass therethrough, but that prevents the head post 928 from passing therethrough.

As shown in FIGS. 68-73, 82 and 85-87, the head post 928 includes an axially/longitudinally extending through hole, cannulated opening or passageway 929 extending therethrough that is configured to allow the first end portion 952 of the tension member 950 to pass therethrough. The head post 928 also includes at least one laterally/radially extending pin aperture or hole 918 that extends from the exterior of the head post 928 to the cannulated opening 929. The first end portion 952 of the tension member 910 can be inserted or passed through the cannulated opening 929 of the head post 928 such that the first opening 956 is aligned with the pin aperture 918. With the first opening 956 being aligned with the pin aperture 918, a head pin 919 can be pressed into/through the pin aperture 918 and into/through the first opening 956 to fix the first end portion 952 of the tension member 910 to the head post 928, as shown in FIGS. 68-73, 82 and 85-87. In some embodiments, the head pin 919 may initially be partially disposed or pre-assembled within a portion of the pin aperture 918 prior to passing the tension member 950 through the cannulated opening 929.

Figure 78:
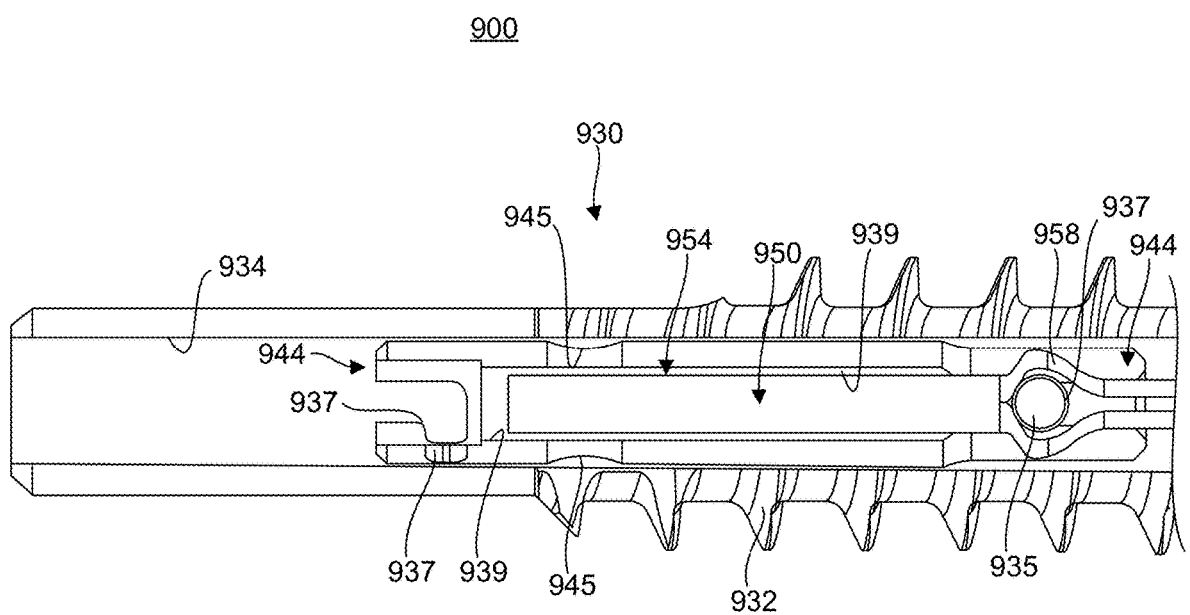
FIG. 78 is a side cross-sectional view of a portion of the implant of FIG. 62 illustrating the engagement of the tip post and the tension member in the cannulation of the anchor member, in accordance with an aspect of the present disclosure.
Figure 79:
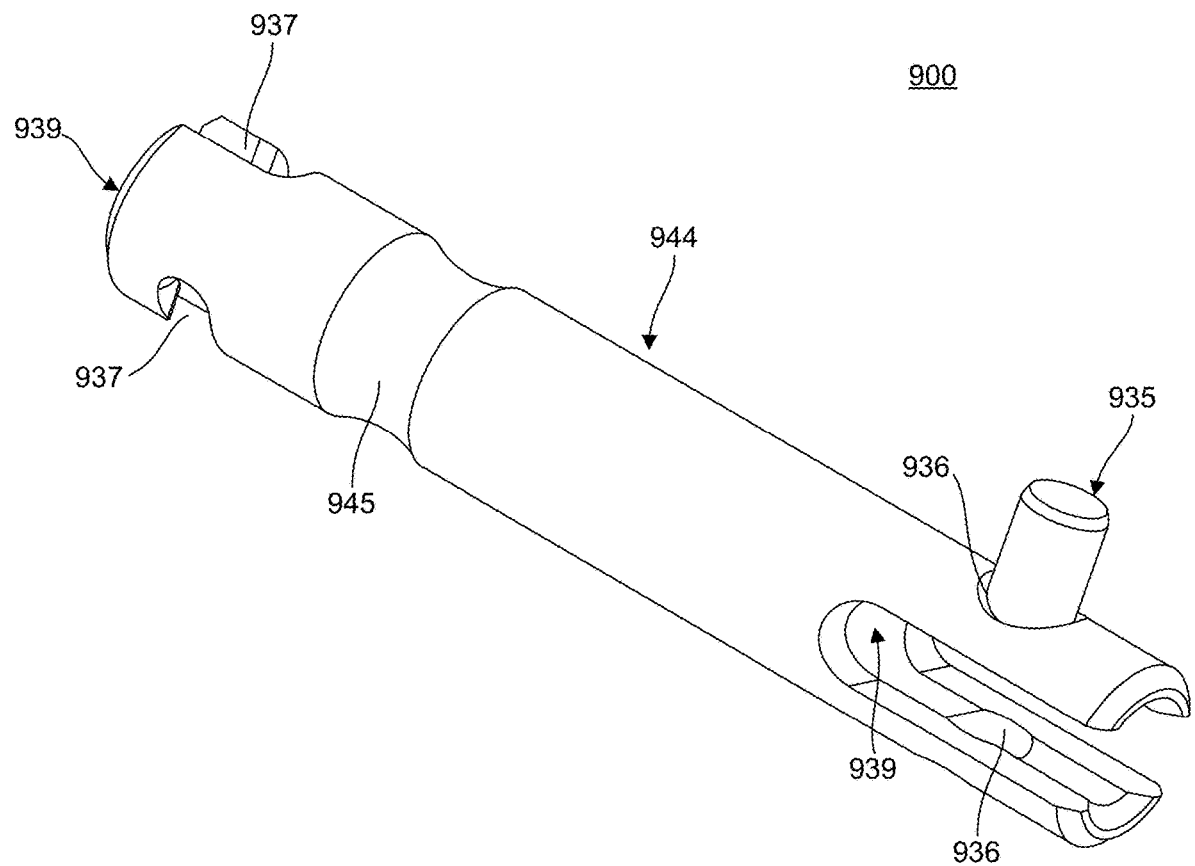
FIG. 79 is another side perspective view of the tip post and the tip pin of the implant of FIG. 62 illustrating a partially-assembled configuration, in accordance with an aspect of the present disclosure.
Figure 83:
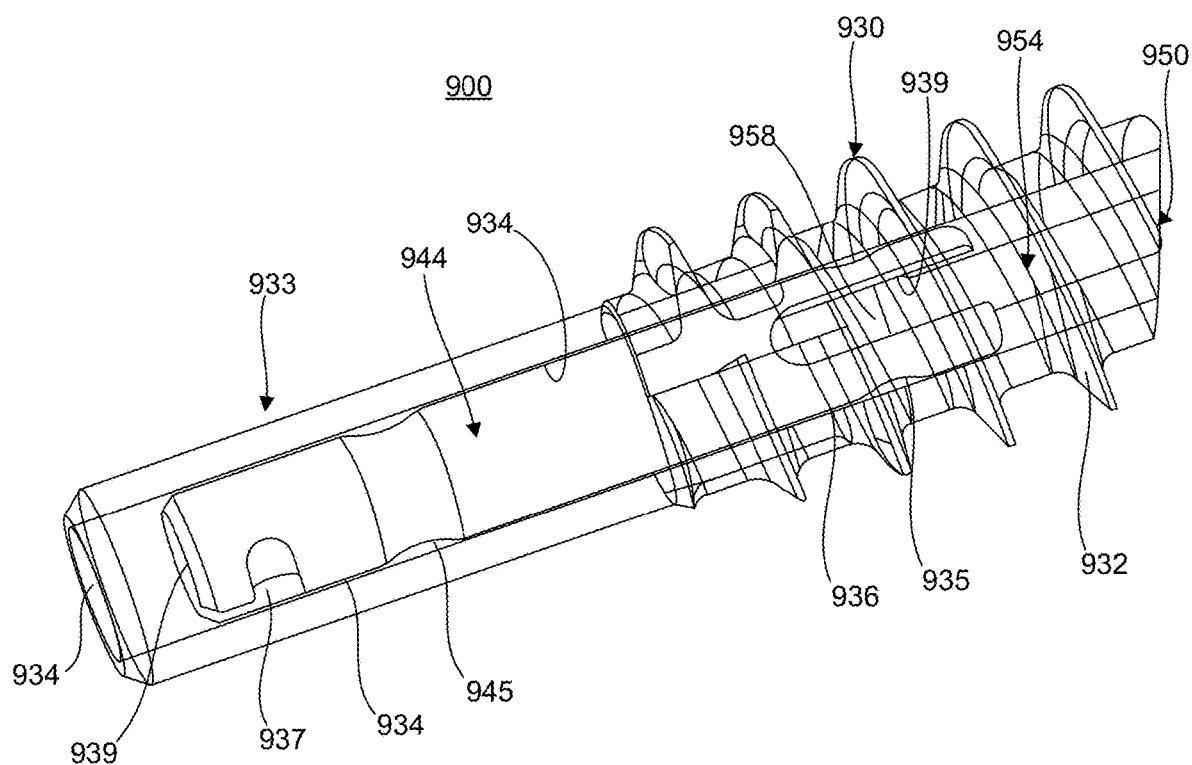
FIG. 83 is a perspective side view of the implant of FIG. 62, illustrating the anchor member in an assembled configuration, in accordance with an aspect of the present disclosure.
Figure 84:
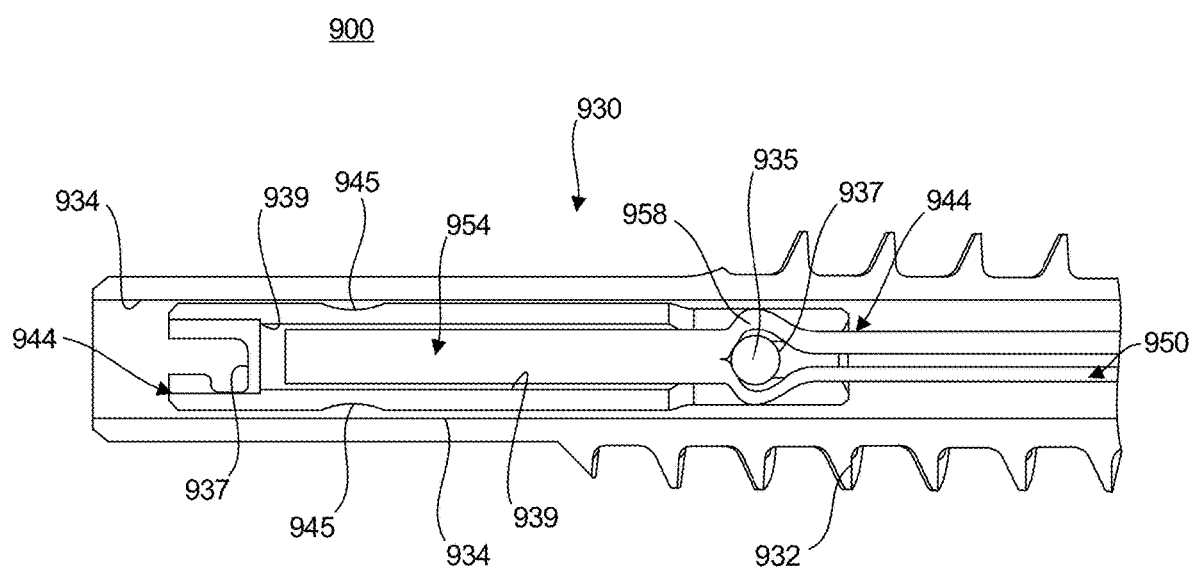
FIG. 84 is another side cross-sectional view of a portion of the implant of FIG. 62 illustrating the engagement of the tip post and the tension member in the cannulation of the anchor member, in accordance with an aspect of the present disclosure.
Figure 85:
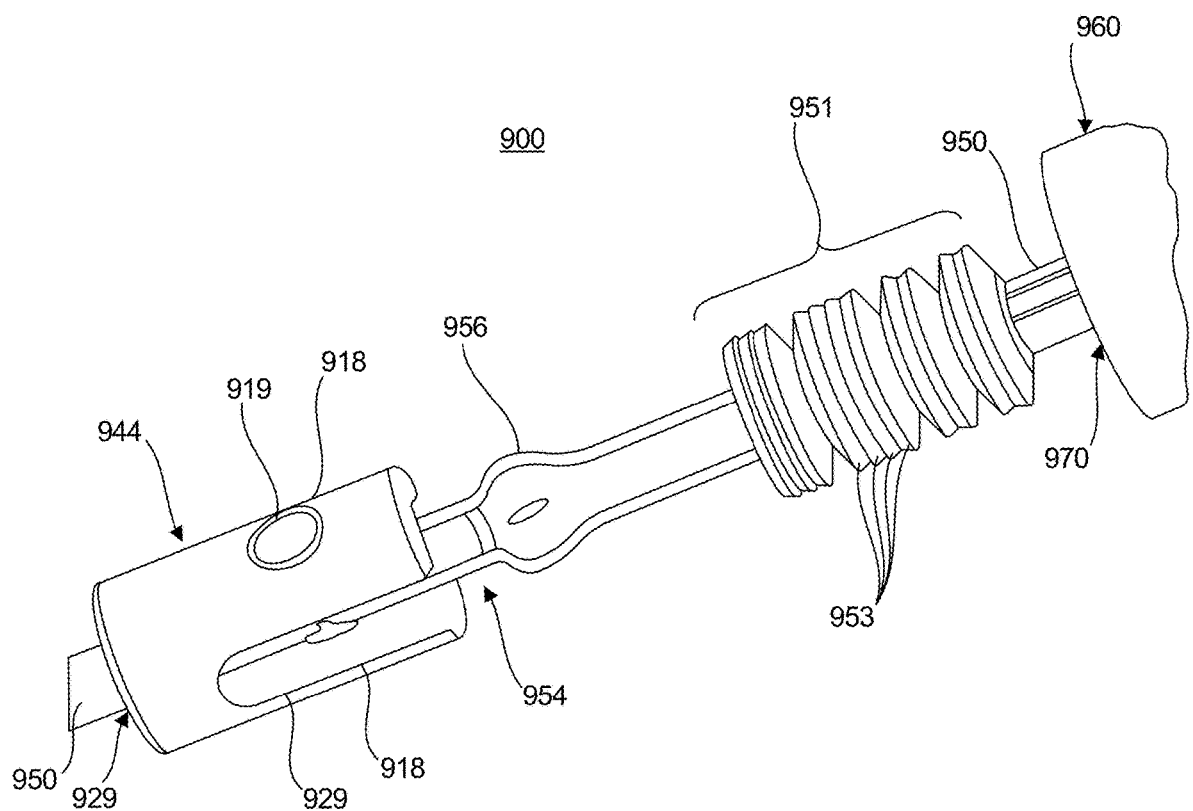
FIG. 85 is an exploded perspective side view of the implant of FIG. 62, illustrating the head post, tension member, resilient member and coupling in a partially-assembled configuration, in accordance with an aspect of the present disclosure.
Figure 86:
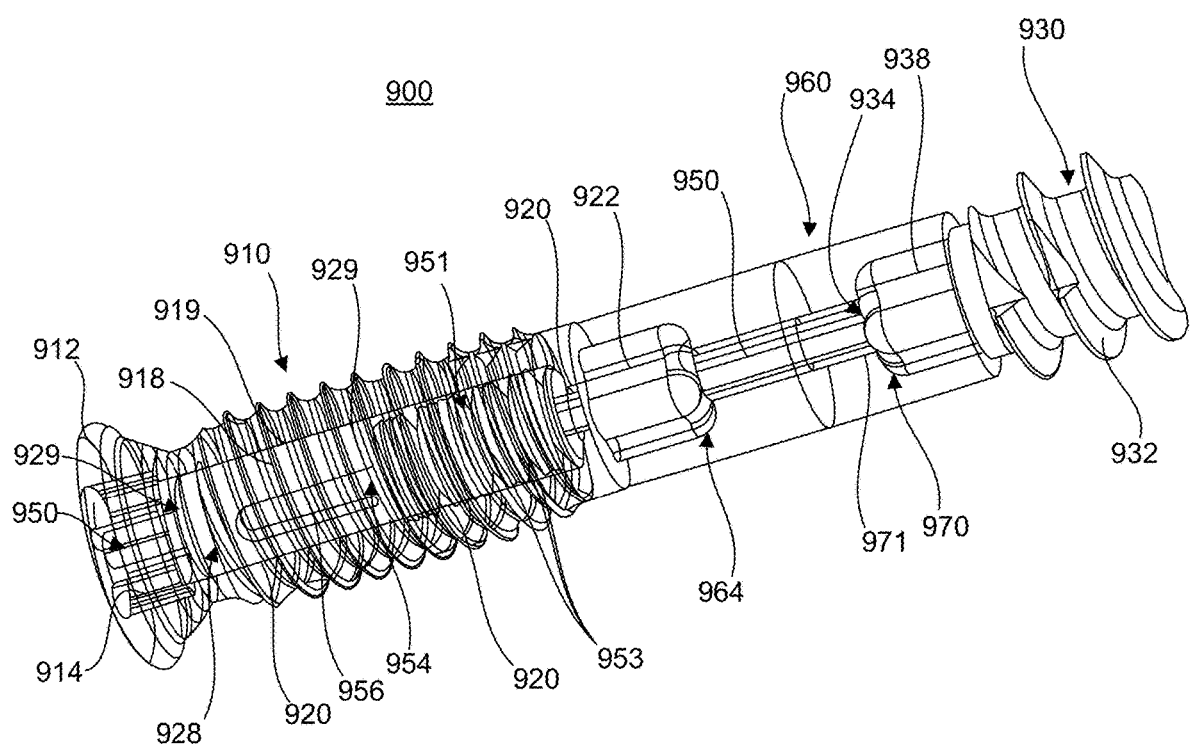
FIG. 86 is another perspective side view of the implant of FIG. 62, illustrating the head member in an assembled configuration, in accordance with an aspect of the present disclosure.

The second end portion 952 of the tension member 950 may be coupled to the anchor member 930 within the cannulated opening 934 thereof via the tip post 944, as shown in FIGS. 78, 80, 81 and 83-855. The tip post 944 may be contained or positioned within the cannulated opening 934 of the anchor member 930 (e.g., the cannulated opening 934 of the crimp portion 933 and the threaded shaft portion 932). Specifically, the cannulated opening 934 of the anchor member 934 (e.g., the cannulated opening 934 of the crimp portion 933 and the threaded shaft portion 932) is configured to allow the tip post 944 to axially slide or translate therein in a neutral, natural or undeformed or un-crimped state, as shown in FIGS. 78, 83 and 84. As explained further below, the crimp portion 933 of the anchor member 930 may be inwardly deformed or crimped such that the cannulated opening 934 thereof is narrowed or partially collapsed to fixed or trap the tip post 944 within a particular or selected axial positioned or location within the cannulated opening 934 along the anchor member 930.

As shown in FIGS. 65, 68-71, 74, 75, 78-81, 83 and 84, the tip post 944 includes an axially/longitudinally extending through hole, cannulated opening or passageway 939 extending therethrough that is configured to allow the second end portion 954 of the tension member 950 to pass therethrough. The tip post 944 also includes at least one laterally/radially extending pin aperture or hole 936 positioned proximate to a second end of the tip post 944. The pin aperture 936 extends from the exterior of the tip post 944 to the cannulated opening 939. The first end portion 952 of the tension member 910 can be inserted or passed through the cannulated opening 939 of the tip post 944 such that the second opening 958 is aligned with the pin aperture 936. With the second opening 958 being aligned with the pin aperture 936, a tip pin 935 can be pressed into/through the pin aperture 936 and into/through the second opening 958 to fix the second end portion 954 of the tension member 910 to the tip post 944, as shown in FIGS. 78, 80, 81, 83 and 84. In some embodiments, the tip pin 935 may initially be partially disposed or pre-assembled within a portion of the pin aperture 936 prior to passing the tension member 950 through the cannulated opening 939.

The tip post 944 also includes a hook slot 937 (e.g., a "J", "L" or "T" shaped slot) extending from a second end thereof. The hook slot 937 may define a slot or passageway that is open to the second end of the tip post 944. The hook slot 937 is configured to allow a member (e.g., a suture, tool or other member or device) (not shown) to extend therein/therethrough to engage the tip post 944 and apply an axial tensioning force to the tip post 944, as shown in FIGS. 65, 68-71, 74, 75, 78-81, 83 and 84. When the tip post 944 is positioned within the cannulated opening 934 of the anchor member 930, the member (not shown), may extend through the cannulated opening 934 and engage the hook slot 937. The tensioning force applied to the tip post 944 via the hook slot 937 may act in a direction extending from the head portion 912 to the free end or tip of the anchor member 930.

As shown in FIGS. 65, 68-71, 74 75 78-81, 83 and 84, the tip post 944 includes a crimp recess or groove 945 extending into the outer surface of the tip post 944. The crimp recess 945 may extend circumferentially about the tip post 944. The crimp recess 945 may be positioned between the hook slot 937 and the pin aperture 936. The crimp recess 945 is configured such that when the tip post 944 is positioned within the cannulated opening 934 of the anchor member 912, a space or gap is formed between the crimp recess 945 and the inner surface of the anchor member 912 forming the cannulated opening 934, as shown in FIGS. 78, 83 and 84. In this way, as described above, the crimp portion 933 of the anchor member 912 may be crimped (i.e., deformed inwardly) such that the side wall of the crimp portion 933 extends into the cannulated opening 934 and the crimp recess 945 (i.e., the cannulated opening 934 is narrowed or partially collapsed into the crimp recess 945) to fix or trap the tip post 944 within a particular or selected axial/longitudinal position or location within the cannulated opening 934 along the anchor member 930.

As shown in FIGS. 68-83, 82 and 85-87, the at least one resilient and/or elastic tensioning member 951 may also be positioned within the enlarged portion of the cannulated opening 929 of the head member 910. The at least one resilient member 951 may be positioned axially/longitudinally between the head post 928 and the narrow portion of the cannulated opening 929. The at least one resilient member 951 may also extend about the tension member 950. For example, the at least one resilient member 951 may extend circumferentially about the bifurcated portion of the tension member 950. The at least one resilient member 951 may thereby include a through hole that accepts the tension member 950.

Figure 82:
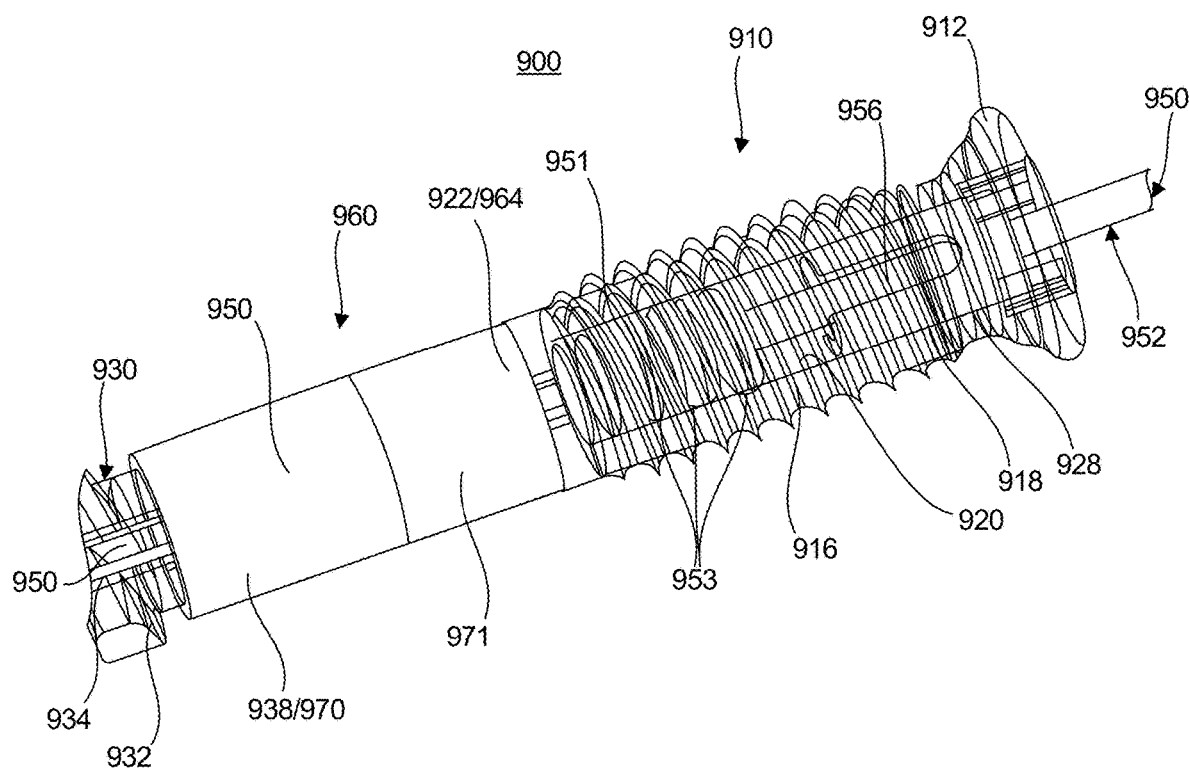
FIG. 82 is a perspective side view of the implant of FIG. 62, illustrating the head member in an assembled configuration, in accordance with an aspect of the present disclosure.

The at least one resilient member 951, the narrow portion of the cannulated opening 929 and/or the head post 928 can be configured (e.g., sized and shaped) such that the at least one resilient member 951 is trapped or contained between the head post 928 and the narrow portion of the cannulated opening 929, as shown in FIG. 82. In this way, when the tension member 950 is tensioned via the tip post 944, the at least one resilient member 951 may be elastically compressed between the end of the enlarged portion of the cannulated opening 929 of the head member 910. The at least one resilient member 951 may thereby apply a compressive force that pulls the anchor member 930 and the head member 910 together after the coupling 960 is resorbed, and/or allows a limited degree of relative axial translation or movement between the anchor member 930 and the head member 910. In some alternative embodiments, the at least one resilient member 951 may not be positioned within the cannulated opening 929 of the head member 910. In some embodiments, the at least one resilient member 951 may be contained or embedded within a bioresorbable material. In some embodiments, the at least one resilient member 951 may be formed of a bioresorbable material.

The at least one resilient member 951 may be formed of any elastically deformable member or material. For example, the at least one resilient member 951 may be one or more springs (e.g., disc or coil spring) or elastically compressible disc or tube, or a combination thereof. For example, the at least one resilient member 951 may comprise an elastically compressible disc (e.g., elastomeric, polymer, polyurethane or polyethylene disc), tube (e.g., a polyurethane tube) or coil spring. In some embodiments, the at least one resilient member 951 comprises a plurality of disc springs, and may include at least one elastomeric (e.g., polyurethane), polymer (e.g., polyethylene) and/or resorbable disc between at least one pair of adjacent disc springs. However, the at least one resilient member 951 may be of any other configuration such that the at least one resilient member 951 is elastically deformable to tension the tension member 950 so that it applies a preloaded compressive force (via elastic deformation of the at least one resilient member 951) that pulls the anchor member 930 and the head member 910 together (before and/or after the coupling 960 is resorbed), and/or allows a limited degree of relative axial translation or movement between the anchor member 930 and the head member 910 (before and/or after the coupling 960 is resorbed).

As shown in FIGS. 68-83, 82 and 85-87, in the exemplary illustrative embodiment the at least one resilient member 951 is comprises of a plurality of disc springs 953 (also known as coned-disc springs, conical spring washers, cupped spring washers, Belleville springs and Belleville washers) which can be axially/longitudinally loaded either statically or dynamically. The disc springs 953 include a central through hole that allows the tension members 950 to extend therethrough. The disc springs 953 include or define a frusto-conical shape that provides a spring or elastic deformation characteristic thereof.

The frusto-conical shape of the disc springs 953 also allows for a bimodal configuration of the at least one resilient member 951 such that the at least one resilient member 951 includes relatively stiffer and relatively less stiff sections or portions. Specifically, the frusto-conical shape of the disc springs 951 allows some disc springs 951 to be stacked or arranged next to each other in the same axial/longitudinal direction or orientation and some other disc springs 951 to be stacked or arranged next to each other in the opposing axial/longitudinal directions or orientations. The disc springs 951 that are stacked or arranged next to each other in the same axial/longitudinal direction or orientation provide a relatively stiffer portion or configuration of the at least one resilient member 951 as compared to that formed by the disc springs 951 that are arranged in an opposing or oppositely orientated arrangement. By including at least some disc springs 951 arranged in the same direction and at least some disc springs 951 arranged in an opposing direction, the at least one resilient member 951 can provide both an assembly tension that maintains the components of the implant 900 together during/after implantation and prior to absorption of the coupling 960 (via the oppositely orientated disc springs 951) and an in-situ tension (via the aligned disc springs 951) after implantation (before and/or after absorption of the coupling 960) to resist anatomical forces, such as syndesmotic forces. For example, if the implant is implanted into a fibula and a tibia with the coupling 960 at least partially positioned within the lateral gutter thereof, the in-situ tension provided at least partially by the aligned disc springs 951 allows or provides for a recoverable diastatic motion of the fibula relative to the tibia, acting to release, absorb and/or dissipate pressure spikes in the lateral gutter, for example. In some embodiments, the oppositely orientated disc springs 951 may be elastically deformed such that the assembly tension maintains the components of the implant 900 mated together, and the oppositely orientated disc springs 951 may not be elastically deformed (or only partially elastically deformed) so as to provide the in-situ tension in response to the recoverable diastatic motion and pressure spikes.

Figure 80:
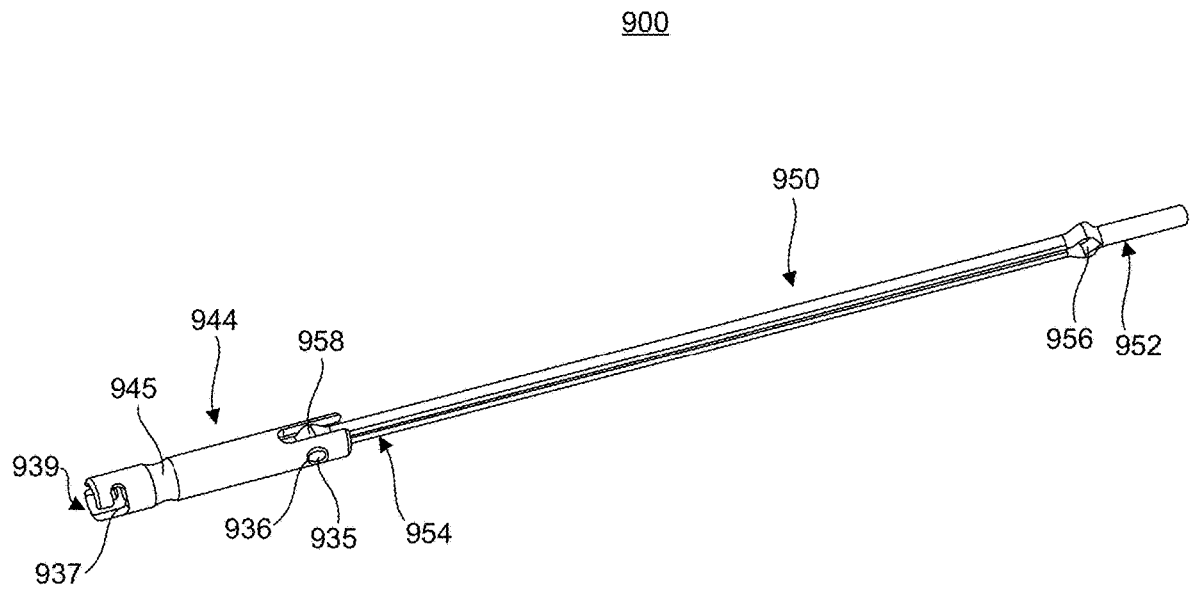
FIG. 80 is a side perspective view of the tip post, tip pin and tension member of the implant of FIG. 62 illustrating an assembled configuration thereof, in accordance with an aspect of the present disclosure.
Figure 81:
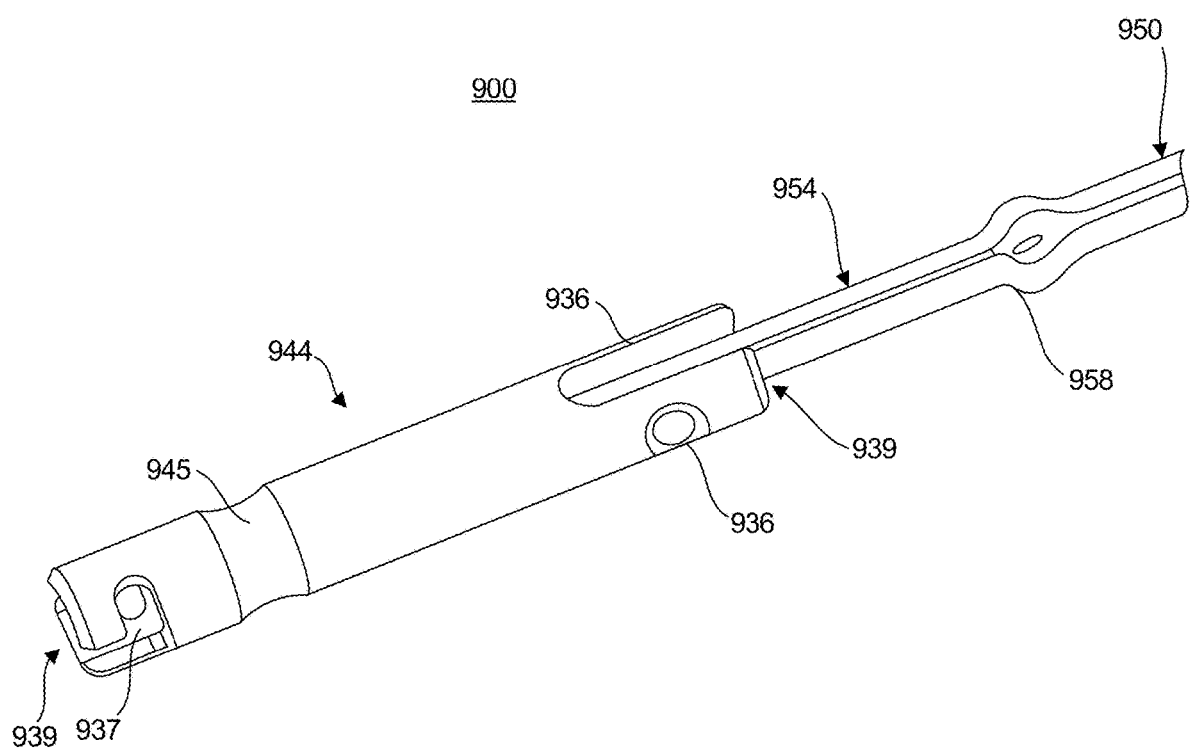
FIG. 81 is an enlarged perspective side view of the tip post, tip pin and tension member of the implant of FIG. 62 illustrating the assembled configuration thereof, in accordance with an aspect of the present disclosure.

The implant 900 may be assembled (i.e., the anchor member 930 and the head member 910 dynamically linked by the tension member 950, at least one resilient member 951 and the coupling 960) by positioning the second end portion 954 of the tension member 950 within the cannulated opening 936 of the tip post 944 such that the bifurcated portion of the tension member 950 is aligned with the pin aperture 936 of the tip post 944 (and potentially the tip pin 935 if pre-assembled with the tip post 944). The second opening 958 of the tension member 950 may be aligned with the pin aperture 936 of the tip post 944 and the tip pin 935 may be pressed or otherwise translated through the pin aperture 936 such that the tip pin 935 extends through the second opening 958 to couple the tension member 950 and the tip post 944 (i.e., to capture the tension member 950 in the tip post 944), as shown in FIGS. 80 and 81.

The pre-assembled tension member 950 and tip post 944 may be assembled with the anchor member 930, the coupling 960, the head member 910, the at least one resilient member 951 and the head post 928. For example, the first end portion 952 of the tension member 950 may be inserted into and through the cannulated opening 934 of the anchor member 930 via the opening at the end of the crimp portion 933, into and through the cannulated opening 971 of the coupling 960, into and through the cannulated opening 920 of the head member 910, into and through the through hole of the at least one resilient member 951 (if the through hole is provided), and into and through the cannulated opening 929 of the head post 928. The tension member 950 may be positioned within the cannulated openings of the implant 900 such that the tip post 944 is also positioned or translated into the cannulated opening 934 of the anchor member 930.

The first end portion 952 of the tension member 950 may be positioned within the cannulated opening 929 of the head post 928 such that the bifurcated portion of the tension member 950 is aligned with the pin aperture 918 of the head post 928 (and potentially the head pin 919 if pre-assembled with the head post 928). The first opening 956 of the tension member 950 may be aligned with the pin aperture 918 of the head post 928 and the head pin 919 may be pressed or otherwise translated through the pin aperture 918 such that the head pin 919 extends through the first opening 956 to couple the tension member 950 and the head post 928 (i.e., to capture the tension member 950 in the head post 928), as shown in FIG. 82.

With the tension member 950 and the head post 928 couple, the tension member 950 may be tensioned via the hook slot 937 of the tip post 944 to axially seat, engage or assemble the components of the implant 900 and apply the assembly tension. For example, a member or tool (e.g., a suture) (not shown) may be inserted into the cannulated opening 934 of the anchor member 930 and engaged with the hook slot 937 of the tip post 944. The tip post 944 and tension member 950 may initially be positioned distal to the free end or tip of the anchor member 930 (formed by the crimp portion 933) within the cannulated opening 934, as shown in FIG. 78. The member or tool may be tensioned to "pull" the tip post 944 via the hook slot 937 axially/longitudinally through the cannulated opening 934 of the anchor member 930 proximate to the free end or tip of the anchor member 930 within the cannulated opening 934, as shown in FIG. 84. The tension member 950 may thereby also be axially/longitudinally translated through the cannulated opening 934 of the anchor member 930, which causes the head post 928 to seat within the cannulated opening 920 of the head member 910 and act against the at least one elastic member 951 to trap the at least one elastic member 951 between the narrow portion of the cannulated opening 920 and the head post 928. Axial/longitudinal translation of the tension member 950 through the cannulated opening 934 of the anchor member 930 may also cause head member 910 to act against the at least one elastic member 951 and fully seat the engagement projection 922 of the head member 910 within the engagement aperture 964 of the coupling 960 and the engagement projection 938 of the anchor member 930 within the engagement aperture 970 of the coupling 960 (if not already fully seated therein), as shown in FIGS. 62-67, 77, 82 and 86.

Further axial/longitudinal transition of the tip post 944 and the second end 954 of the tension member 950 through the cannulated opening 934 of the anchor member 930 toward the free end or tip of the anchor member 930 (via "pulling" or tensioning via the hook slot 937) causes the head post 928 to compress the at least one resilient member 951 (between the head post 928 and the end of the enlarged portion of the cannulated opening 920 of the head member 910) to elastically deform the at least one resilient member 951. The at least one resilient member 951 may thereby apply the assembly tension force to the anchor member 930 and the head member 910 via the tension member 950 acting to pull (or push) the anchor member 930 and the head member 910 together. As described above, the at least one resilient member 951 may have portions of differing stiffnesses, and the at least one resilient member 951 may only be partially elastically compressed or deformed so that a relatively less stiff portion is deformed to provide the assembly tension force but a relatively stiffer portion is not deformed (or only partially deformed) so that in situ forces can be dissipated or absorbed by deformation of the stiffer portion. To fix or maintain the assembly tension force, the position of the tip post 944 proximate to the free end or tip of the anchor member 930 within the cannulated opening 934 may be fixed or maintained via crimping or inwardly deforming the crimp portion 933 of the anchor member 930 into the crimp recess 945 of the tip post 944 (not shown).

As described above with respect to implant 100-700, after implanting or inserting the implant 900 into first and second bones with the coupling 960 at least partially positioned in a joint or space therebetween, the coupling 960 will eventually fail leaving the head member 910 coupled to the anchor member 930 by only the tension member 950. The coupling 960 may fail, for example, after at least a portion of the coupling 960 is resorbed into the patient. Failure of the coupling 960 will allow for semi-constrained motion between the first and second bones via the tension member 950 and the at least one resilient member 951. The flexibility of the at least one resilient member 951 (and potentially the tension member 950) may allow for diastatic motion of the implant 900. Thus, the implant 900 allows for the patient's physiologic motion to be restored, as well as allowing for diastatic motion and/or pressure spikes, for example.

An exemplary embodiment of another implant according to the present disclosures is shown in FIGS. 88-91 and generally indicated with the reference numeral 1000. Some aspects, elements and/or functions of exemplary implant 1000 are the same or similar in structure and/or function, at least in part, to the exemplary implants 100, 200, 300, 400, 500, 600, 700 and/or 900 described above and shown in FIGS. 1-87, and therefore like reference numerals preceded by the numeral "10" are used to indicate like components, aspects, configurations, functions or processes, and the description above directed thereto (and the alternative embodiments thereof) equally applies to the implant 1000.

As shown in FIGS. 88-91, the implant 1000 is substantially similar to implant 900. As shown in FIGS. 88-91, the implant 1000 is differs from the implant 900 with respect to the configuration of the at least one resilient member 1051. The at least one resilient member 1051 comprises a bumper positioned within the cannulation 1020 of the head member 1010, as shown in FIGS. 88-91. Specifically, as shown in FIGS. 88-91, the bumper 1051 is positioned within the enlarged portion of the cannulation 1020 of the head member 1010 between the head post 1028 and the narrow portion of the of the cannulation 1020 of the head member 1010. As shown in FIGS. 88-91, the bumper 1051 may be formed as a tube with a through-aperture or cannulation 1073 extending therethrough. The tension member 1050 (e.g., the first end portion 1052 thereof) may thereby pass through the cannulation 1073 of the bumper 1051.

The elastic bumper 1051 may be formed of any resilient and/or elastic material. In some embodiments, the bumper 1051 may be formed of one or more urethanes, such as one or more thermoplastic urethanes. For example, the bumper 1051 may be elastic and/or formed of thermoplastic urethane (TPU), polycarbonate urethane (PCU) or a combination thereof.

Figure 92:
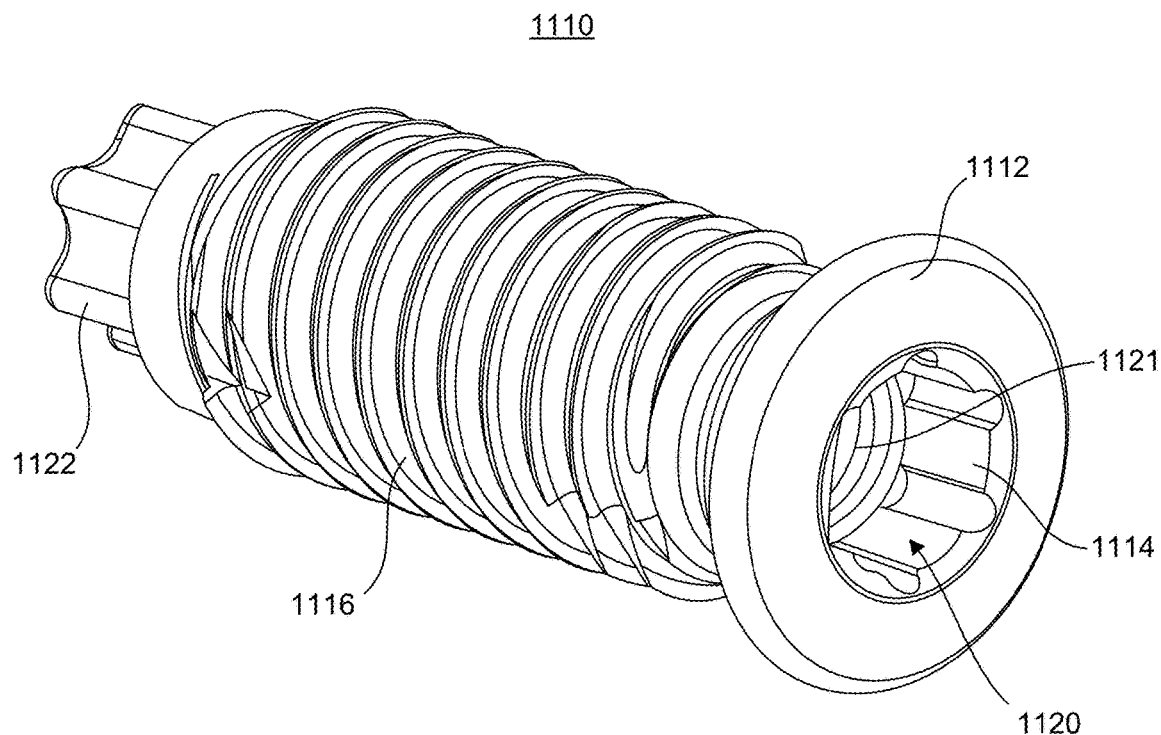
FIG. 92 is a perspective side view of another head member for an implant, in accordance with an aspect of the present disclosure.
Figure 93:
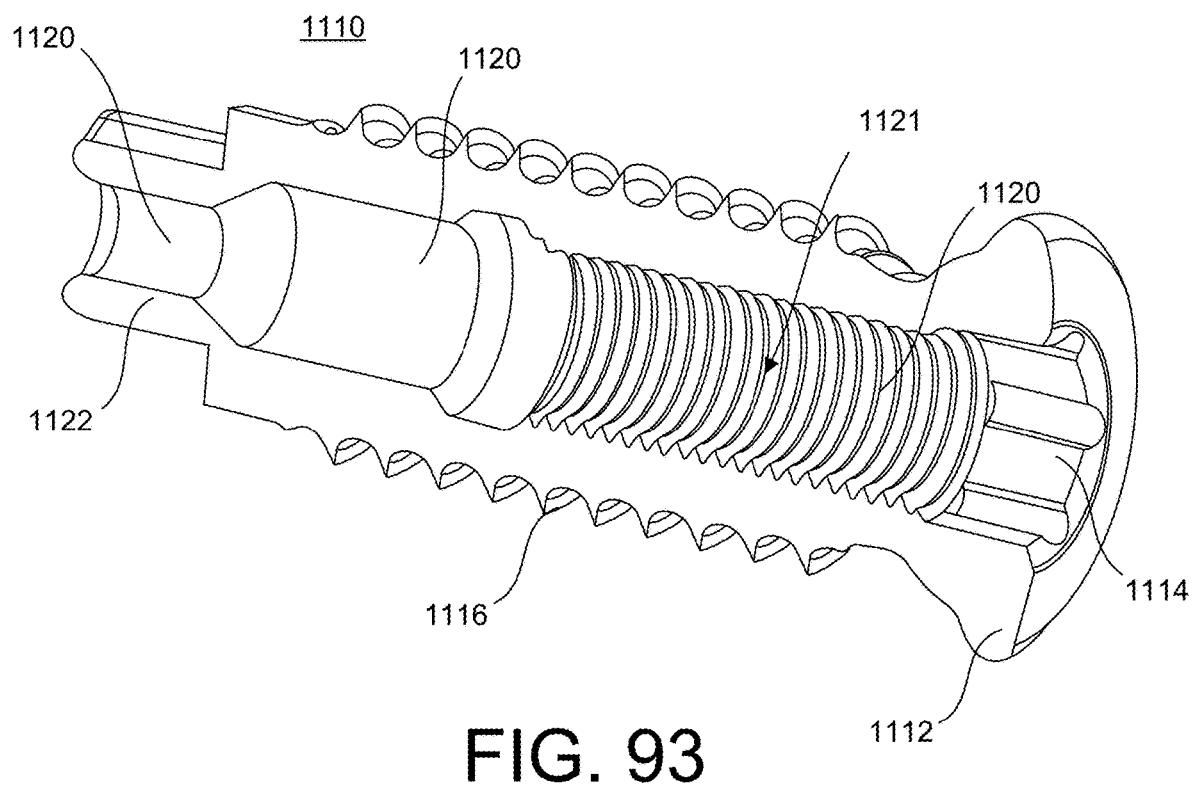
FIG. 93 is a side cross-sectional perspective view of the head member of FIG. 92, in accordance with an aspect of the present disclosure.

An exemplary embodiment of another head member of/for an implant according to the present disclosures is shown in FIGS. 92 and 93 and generally indicated with the reference numeral 1110. Some aspects, elements and/or functions of exemplary head member 1110 are the same or similar in structure and/or function, at least in part, to the exemplary head members 110, 210, 310, 410, 510, 610, 710, 910 and/or 1010 described above and shown in FIGS. 1-87, and therefore like reference numerals preceded by the numeral "11" are used to indicate like components, aspects, configurations, functions or processes, and the description above directed thereto (and the alternative embodiments thereof) equally applies to the implant 1000. Similarly, the head member 1110 may be utilized as the head member of any of exemplary implants 100, 200, 300, 400, 500, 600, 700 and/or 900 described above and shown in FIGS. 1-87.

As shown in FIGS. 92 and 93, a portion of the through hole, cannulated opening or passageway 1120 of the head member 1110 may include an internally-threaded portion 1121. For example, the internally-threaded portion 1121 may be proximate to and/or extend from the engagement opening 1114. The internally-threaded portion 1121 may be threadably engaged with a head post or member (not shown) that is coupled to a first end portion of a tension member (not shown). For example, the head post 928 of FIGS. 62-87 or the head post 1028 of FIGS. 88-91 may be externally threaded and threadably engaged with the internally-threaded portion 1121.

A head post or member threadably engaged with the internally-threaded portion 1121 of the cannulation 1120 of the head member 1110 may include a non-circular engagement opening or aperture having an irregular or non-circular cross-sectional shape so that a correspondingly shaped tool can mate therewith and apply a torque to the head post or member to rotate the head post or member. The head post or member may thereby be longitudinally/axially translated within the head post or member along the internally-threaded portion 1121 of the cannulation 1120 of the head member 1110. In this way, the head post or member and the internally-threaded portion 1121 of the cannulation 1120 of the head member 1110 may be utilized to tension the tension member when a second end portion of the tension member is fixed or coupled to another portion of the implant. It is noted that the tension member that is coupled or affixed to the tension member may be twisted or untwisted as the head post or member is rotated within the internally-threaded portion 1121 of the cannulation 1120 of the head member 1110.

As may be recognized by those of ordinary skill in the art based on the teachings herein, numerous changes and modifications may be made to the above-described and other embodiments of the present disclosure without departing from the scope of the disclosure. The head member, anchor member, tension member, coupling, and other components of the implant and/or system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants and systems may include more or fewer components or features than the embodiments as described and illustrated herein. For example, the components and features of FIGS. 1-11, FIGS. 12-16, FIGS. 17-23, FIGS. 24-32, 35 and 36, FIGS. 37-45, FIGS. 46-52, FIG. 53, FIG. 54, FIG. 55, FIGS. 56-61 and FIGS. 62-87 may all be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:
1. An implant, comprising:
a head member;
an anchor member;
a coupling member positioned between and coupling the head member and the anchor member; wherein the coupling member is made of bioresorbable material and may translate along the tension member; and at least one pin, wherein the at least one pin is sized to be inserted into at least one transverse opening and at least one slot, wherein at least one pin pressingly engages a tension member into the at least one slot to secure the tension member to the anchor member.

2. The implant of claim 1, wherein the head member comprises:

a first engagement protrusion;

wherein the anchor member comprises:

a second engagement protrusion; and wherein the coupling member comprises:

a first engagement aperture that receives the first engagement protrusion of the head member; and a second engagement aperture that receives the second engagement protrusion of the anchor member.

3. The implant of claim 2, wherein the first engagement protrusion, the second engagement protrusion, the first engagement aperture, and the first engagement aperture define a non-circular cross-section.

4. The implant of claim 3, wherein the first engagement protrusion, the second engagement protrusion, the first engagement aperture, and the first engagement aperture define a non-circular cross-section that includes a plurality of lobes with a recess extending between adjacent lobes.

5. The implant of claim 4, wherein a cannulation of the head member extends through the first engagement protrusion, a cannulation of the anchor member extends through the second engagement protrusion, and the cannulation of the head member is in communication with the first engagement aperture and the second engagement aperture.

6. The implant of claim 5, wherein the head member comprises:

a head portion; and a shaft portion extending from the head portion, wherein the head portion defines a free end of the implant.

7. The implant of claim 1, wherein at least a portion of the head member is threaded.

8. The implant of claim 1, further comprising:

a head post positioned within a cannulated opening of the head member; and a tip post positioned within a cannulated opening in the anchor member.

9. The implant of claim 8, wherein the head post couples to a portion of the tension member.

10. The implant of claim 9, wherein the head post axially slides within the cannulated opening of the head member.

11. The implant of claim 8, wherein the tip post couples to a portion of the tension member.

12. The implant of claim 11, wherein the tip post axially slides within the cannulated opening of the anchor member.

13. The implant of claim 8, further comprising:

at least one resilient member.

14. The implant of claim 13, wherein the at least one resilient member may extend circumferentially about the tension member.

15. The implant of claim 14, wherein the at least one resilient member is positioned axially between the head post and a narrow portion of the cannulated opening.

16. The implant of claim 13, wherein the at least one resilient member is formed of an elastically deformable material.

17. The implant of claim 13, wherein the at least one resilient member comprises:

a plurality of disc springs.

\* \* \* \* \*